United States Patent
Guo et al.

(10) Patent No.: US 11,136,625 B2
(45) Date of Patent: Oct. 5, 2021

(54) GENE EXPRESSION SIGNATURES PREDICTIVE OF SUBJECT RESPONSE TO A MULTI-KINASE INHIBITOR AND METHODS OF USING THE SAME

(71) Applicant: Crown Bioscience, Inc. (Taicang), Jiangsu Province (CN)

(72) Inventors: Sheng Guo, Jiangsu (CN); Daiwei Chen, Beijing (CN); Juan Zhang, Jiangsu (CN); Jie Cai, Quebec (CA); Henry Qixiang Li, Carlsbad (CA)

(73) Assignee: CROWN BIOSCIENCE, INC. (TAICANG), Jiangsu Province (CN)

( * ) Notice: Subject to any disclaimer, the term of this patent is extended or adjusted under 35 U.S.C. 154(b) by 0 days.

(21) Appl. No.: 14/915,121

(22) PCT Filed: Aug. 28, 2014

(86) PCT No.: PCT/US2014/053142
§ 371 (c)(1),
(2) Date: Feb. 26, 2016

(87) PCT Pub. No.: WO2015/031604
PCT Pub. Date: Mar. 5, 2015

(65) Prior Publication Data
US 2016/0208328 A1 Jul. 21, 2016

(30) Foreign Application Priority Data
Aug. 28, 2013 (WO) ................ PCT/CN2013/082487

(51) Int. Cl.
*C12Q 1/6883* (2018.01)
*C12Q 1/6886* (2018.01)

(52) U.S. Cl.
CPC ........ *C12Q 1/6883* (2013.01); *C12Q 1/6886* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 2006/0019256 A1* | 1/2006 | Clarke ................. | C12N 5/0695 435/6.14 |
| 2007/0105133 A1* | 5/2007 | Clarke ................. | C12N 5/0693 435/6.12 |
| 2010/0130527 A1* | 5/2010 | Lehrer ................... | G16B 25/00 514/291 |
| 2011/0245473 A1 | 10/2011 | Igawa et al. | |
| 2012/0214830 A1* | 8/2012 | Buck ................ | G01N 33/57438 514/266.4 |
| 2012/0245051 A1 | 9/2012 | Rimm et al. | |
| 2013/0122524 A1 | 5/2013 | Fantl et al. | |
| 2014/0087362 A1* | 3/2014 | Szalay ................... | C07K 14/00 435/5 |
| 2014/0322166 A1* | 10/2014 | Willman .............. | C12Q 1/6886 424/85.7 |

FOREIGN PATENT DOCUMENTS

| | | |
|---|---|---|
| CN | 102283836 A | 12/2011 |
| JP | 2006-500074 A | 1/2006 |
| JP | 2008-546387 A | 12/2008 |
| JP | 2010-504530 A | 2/2010 |
| JP | 2012-506560 A | 3/2012 |
| WO | WO 2004/029287 A2 | 4/2004 |
| WO | WO 2006/138275 A2 | 12/2006 |
| WO | WO 2007/047955 A2 | 4/2007 |
| WO | WO 2008/082730 A2 | 7/2008 |
| WO | WO 2009/015368 A2 | 1/2009 |
| WO | WO 2010/048304 A2 | 4/2010 |
| WO | WO 2013/022995 A2 | 2/2013 |
| WO | WO 2013/090419 A1 | 6/2013 |
| WO | WO 2015/031604 A1 | 3/2015 |

OTHER PUBLICATIONS

Enard et al. (Science 2002 vol. 296 p. 340) (Year: 2002).*
Cobb et al. (Crit Care Med 2002 vol. 30 p. 2711) (Year: 2002).*
Zhu et al. "Biomarkers for hepatocellular carcinoma: progression in early diagnosis, prognosis, and personalized therapy", *Biomarker Research*, Feb. 5, 2013, 1(10):1-8.
Harding et al., "Predicting responsiveness to sorafenib: can the determination of FGF3/FGF4 amplifications enrich for clinical benefit?" *Hepatobiliary Surgery and Nutrition*, Aug. 1, 2014, 3(4): 168-171.
International Search Report based on International Patent Application Serial No. PCT/US2014/053142, dated Dec. 17, 2014.
Written Opinion based on International Patent Application Serial No. PCT/US2014/053142, dated Dec. 17, 2014.
Affymetrix, Inc. "AffymetrixGeneChip Human Genome U133 Array Set HG-U133a," NCBI Geo Accession Display, Platform GPL96, pp. 1-254 (Mar. 11, 2002).
Affymetrix, Inc. "Affymetrix GeneChip Human Genome U133 Array Set HG-U133a," NCBI Geo Accession Display, Platform GPL96, pp. 255-511 (Mar. 11, 2002).
Supplementary Euopean Search Report, EP appl. No. 14840944.4, 8 pages (dated Feb. 23, 2017).
International Preliminary Report on Patentability in International Patent Application Serial No. PCT/US2014/053142, dated Mar. 1, 2016, 8 pages.

* cited by examiner

Primary Examiner — Katherine D Salmon
(74) Attorney, Agent, or Firm — Cooley LLP

(57) ABSTRACT

Gene expression signature predictive of cancer patient response to multi-kinase inhibitor is disclosed. Also disclosed are methods predicting the efficacy of the multi-kinase inhibitor for treating cancer in a patient. Also disclosed are methods for distinguishing responders from non-responders to a multi-kinase inhibitor in treating cancer. Also disclosed are methods for treating a cancer patient with a multi-kinase inhibitor.

6 Claims, 6 Drawing Sheets

Specification includes a Sequence Listing.

SEQUENCE LISTING

<160> NUMBER OF SEQ ID NOS: 32

<210> SEQ ID NO 1
<211> LENGTH: 4304
<212> TYPE: DNA
<213> ORGANISM: Homo sapiens

<400> SEQUENCE: 1

```
gctccctact ccgcctctcg ggatccttta agaggcgggg cttggctgcc agctccgcgg      60
cccgggcaaa aggctgggac tttactccgg gtggcggcga ggacgagtct gtgctccatc     120
agctgccgca cccgccgcct cccgccccca aaccccatcc ccgcggttga gccacgatga     180
gcggcagagt cggcgatctg agcccaggc agaaggaggc attggccaag tttcgggaga     240
atgtccagga tgtgctgccg gccctgccga atccagatga ctattttctc ctgcgttggc     300
tccgagccag aagcttcgac ctgcagaagt cggaggccat gctccggaag catgtggagt     360
tccgaaagca aaaggacatt gacaacatca ttagctggca gcctccagag gtgatccaac     420
agtatctgtc aggggggtatg tgtggctatg acctggatgg ctgcccagtc tggtacgaca     480
taattggacc tctggatgcc aagggtctgc tgttctcagc ctccaaacag gacctgctga     540
ggaccaagat gcgggagtgt gagctgcttc tgcaagagtg tgcccaccag accacaaagt     600
tggggaggaa ggtggagacc atcaccataa tttatgactg cgaggggctt ggcctcaagc     660
atctctggaa gcctgctgtg gaggcctatg agagtttct ctgcatgttt gaggaaaatt     720 atccccgaaac actgaagcgt ctttttgttg ttaaagcccc caaactgttt cctgtggcct     780
ataacctcat caaacccttc ctgagtgagg acactcgtaa gaagatcatg gtcctgggag     840
caaattggaa ggaggtttta ctgaaacata tcagccctga ccaggtgcct gtggagtatg     900
ggggcaccat gactgaccct gatggaaacc ccaagtgcaa atccaagatc aactacgggg     960
gtgacatccc caggaagtat tatgtgcgag accaggtgaa acagcagtat gaacacagcg    1020
tgcagatttc ccgtggctcc tcccaccaag tggagtatga gatcctcttc cctggctgtg    1080
tcctcaggtg gcagtttatg tcagatggag cggatgttgg ttttgggatt ttcctgaaga    1140
ccaagatggg agagaggcag cgggcagggg agatgacaga ggtgctgccc aaccagaggt    1200
acaactccca cctggtccct gaagatggga ccctcacctg cagtgatcct ggcatctatg    1260
tcctgcggtt tgacaacacc tacagcttca ttcatgccaa gaaggtcaat ttcactgtgg    1320
aggtcctgct tccagacaaa gcctcagaag agaagatgaa acagctgggg gcaggcaccc    1380
cgaaataaca ccttctccta tagcaggcct ggccccctca gtgtctccct gtcaatttct    1440 acccttgta gcagtcattt tcgcacaacc ctgaagccca aagaaactgg gctggaggac    1500
agacctcagg agctttcatt tcagttaggc agaggaagag cgactgcagt gggtctccgt    1560
```

-continued

```
gtctatcaaa tacctaagga gtccccagga gctggctggc catcgtgata ggatctgtct    1620
gtcctgtaaa ctgtgccaac ttcacctgtc cagggacagc gaagctgggg gtggcggggg    1680
gcatgtacca cagggtggca gcagggaaaa aaattagaaa agggtgaaag attgggactt    1740
aacacttcag ggaagtcagc tgccggggag aaacttgctc ctaaatgaac acataagttt    1800
agatcgcaat gaggagtagc agggtagctg gttgctagag ttacggtggg gatcagaaac    1860
tcttccaaac attttagcac tgaggctggg gtagcttttg cttttccca ggtctcagga     1920
ggtggcctga gtcagcacac atcttcccac tcggtagaca ggctggcctc tccctcactt    1980
tgagactttg caactcctg ggccacacgg cctgcctctt tgattactaa tgattgtcag     2040
tgactcagag cttcctggga cttcgggtac ccacccgctg ttctccatgc aaacaaagcg    2100
ccagggaaat gacccacagg gatcgcagct gcagggaggg ccaggaggt tgggggtggg     2160
agtgaatgct aaaagcagat cgtccagtgc ccttttcagt gctaccggcc tctcaccaag    2220
cagtcctcca tgtgagcaac cccgagacaa aaatgctaag tgggatcaag agagcagcac    2280
tcggagaggg tgtttgccag tctgagtgtc ccgcggtgcc cgccaacccg cttcctgact    2340
gacctgagca aggtcttact aagcagtccc atctctgtgg gaggcatgca acgcgtgcag    2400
ggagttcagg tgccggtcgg cgtagccagg cctggaggcc ccccaggcag gaggccgccc    2460
aaaggcgggg ccggcgtctc gcagactagg ggctgggggc ggccacagac ggcctcgaaa    2520
ccacagccct taccccaatc ccacgagccc cgccaacgaa ccacaggtgc tgggctttag    2580
agaacatggg aaggcggccc cagacctggc gggaacgcct ttccctcaga gccaggcccc    2640
ggccccgtct gggaagctca tcttgcgaag ctgagggagc tcaggcaaa ggccaggcta    2700
gcgcggaccg gaaggggccg aggctgcacg ggcctctgcc agaacgctca ggacatcccg    2760
gcctgggttt acaacgctgt taggaaaatt aaccaatgaa taaagcaacg ttcagtgcgc    2820
agggagtgaa attcaatgcc caccgctagg ctcctcgctg cctctcactc aagaggccca    2880
aactcagacg cgtcaggga cccggaccca gcagccgttt cacgccaata datagggcgc     2940
atgcgcagaa atcctcctcg gctctctagc gtgagctttc caaggggcc acgcccagct     3000
tgccttctga ttggtccagc tggtgggttg tcttccgcca tctttgatca gggcactaag    3060
gatgctcccc acggccttca cagtgacggc ggagaccctg ccccgccagc tgctcagtac    3120
gtgccgcgta gcccgtgcga gccaagtgtg agtccgggcg agcgcctgcg gagctagcac    3180
tgggcccaga atgagaggga ggcggaggag cagcgatcac gtggttttag ggactgtcta    3240
ataattccac gccagcattg ccggtgtttc aggggggtggg aaccgctgcg ttccccatca   3300
acttttctcc cacccaccac cctccccaac ctacaagccc agctcagctt gaggtaactg    3360
ctgaccggac tgtcctatac agccctacaa gacagaggcg cctagggctg aaagcggggg    3420
cctccgtagg gagccagcgg gggcctcaat agttactcat tttctctacc tttgatgaaa    3480
ataagagcta attcttaata aggcctaccg ggtatcacgc aaaaaccctg tgcttactat    3540
tacactttgg gttgttgcaa agattaaagg aaataagccg tgcaaagcgc ttaagagctt    3600
ggtataagta agtgctcgtc aatgttggct actctcattt ttttgcaga cgtgggaact     3660
ggggctcagg gaggctaaca gccagtaggc ggcacagcta ggatttgaac ccaggattgt    3720
ctccaacgcc gctcaattat acccgccaag gagtcacaga gacttagtga agtgcacaca    3780
ttgctcacct gggtgaactg aggtccagcg ggggaaggct tcctcctgtt gtaatcacta    3840
accccaactc tgtctccctt gcccgattca ttcattcgtt aattaattca tccaacatcc    3900
tgtccccaag aagctcagtc tggggacata ctgatccagt taaatgcgag tgcttcctag    3960
```

-continued

```
ttatacatgg cgactgctga agggactc cagagtccag gcacctacct cccaggggct    4020
caccgttcac tcctctagcc tcatttagag ctcgcattaa gagcacggga tctggatcca    4080
cactgtttgg attcaaatca caacttcacc acttagcagc tgtgtgttct gggaaaatga    4140
cccaccttct ctgtgcctcc attttctcac ctgtaaaacg ggctcccagg ctggtgggag    4200
ggtttcaggt gtaagacatg gagagtcctt tagcgaacat gtagactggc aataaactca    4260
ataaatggtg actgttataa ttaaaaaaaa aaaaaaaaa aaaa                      4304
```

<210> SEQ ID NO 2
<211> LENGTH: 403
<212> TYPE: PRT
<213> ORGANISM: Homo sapiens

<400> SEQUENCE: 2

```
Met Ser Gly Arg Val Gly Asp Leu Ser Pro Arg Gln Lys Glu Ala Leu
1               5                   10                  15

Ala Lys Phe Arg Glu Asn Val Gln Asp Val Leu Pro Ala Leu Pro Asn
            20                  25                  30

Pro Asp Tyr Phe Leu Leu Arg Trp Leu Arg Ala Arg Ser Phe Asp
        35                  40                  45

Leu Gln Lys Ser Glu Ala Met Leu Arg Lys His Val Glu Phe Arg Lys
    50                  55                  60

Gln Lys Asp Ile Asp Asn Ile Ile Ser Trp Gln Pro Glu Val Ile
65                  70                  75                  80

Gln Gln Tyr Leu Ser Gly Gly Met Cys Gly Tyr Asp Leu Asp Gly Cys
                85                  90                  95

Pro Val Trp Tyr Asp Ile Ile Gly Pro Leu Asp Ala Lys Gly Leu Leu
            100                 105                 110

Phe Ser Ala Ser Lys Gln Asp Leu Leu Arg Thr Lys Met Arg Glu Cys
        115                 120                 125

Glu Leu Leu Leu Gln Glu Cys Ala His Gln Thr Thr Lys Leu Gly Arg
    130                 135                 140

Lys Val Glu Thr Ile Thr Ile Ile Tyr Asp Cys Glu Gly Leu Gly Leu
145                 150                 155                 160

Lys His Leu Trp Lys Pro Ala Val Glu Ala Tyr Gly Glu Phe Leu Cys
                165                 170                 175

Met Phe Glu Glu Asn Tyr Pro Glu Thr Leu Lys Arg Leu Phe Val Val
            180                 185                 190

Lys Ala Pro Lys Leu Phe Pro Val Ala Tyr Asn Leu Ile Lys Pro Phe
        195                 200                 205

Leu Ser Glu Asp Thr Arg Lys Lys Ile Met Val Leu Gly Ala Asn Trp
    210                 215                 220

Lys Glu Val Leu Leu Lys His Ile Ser Pro Asp Gln Val Pro Val Glu
225                 230                 235                 240

Tyr Gly Gly Thr Met Thr Asp Pro Asp Gly Asn Pro Lys Cys Lys Ser
                245                 250                 255

Lys Ile Asn Tyr Gly Gly Asp Ile Pro Arg Lys Tyr Tyr Val Arg Asp
            260                 265                 270

Gln Val Lys Gln Gln Tyr Glu His Ser Val Gln Ile Ser Arg Gly Ser
        275                 280                 285

Ser His Gln Val Glu Tyr Glu Ile Leu Phe Pro Gly Cys Val Leu Arg
    290                 295                 300

Trp Gln Phe Met Ser Asp Gly Ala Asp Val Gly Phe Gly Ile Phe Leu
305                 310                 315                 320
```

```
Lys Thr Lys Met Gly Glu Arg Gln Arg Ala Gly Glu Met Thr Glu Val
            325                 330                 335

Leu Pro Asn Gln Arg Tyr Asn Ser His Leu Val Pro Glu Asp Gly Thr
        340                 345                 350

Leu Thr Cys Ser Asp Pro Gly Ile Tyr Val Leu Arg Phe Asp Asn Thr
    355                 360                 365

Tyr Ser Phe Ile His Ala Lys Lys Val Asn Phe Thr Val Glu Val Leu
370                 375                 380

Leu Pro Asp Lys Ala Ser Glu Glu Lys Met Lys Gln Leu Gly Ala Gly
385                 390                 395                 400

Thr Pro Lys

<210> SEQ ID NO 3
<211> LENGTH: 1845
<212> TYPE: DNA
<213> ORGANISM: Homo sapiens

<400> SEQUENCE: 3
gctccctact ccgcctctcg ggatccttta agaggcgggg cttggctgcc agctccgcgg      60
cccgggcaaa aggctgggac tttactccgg gtggcggcga ggacgagtct gtgctccatc    120
agctgccgca cccgccgcct cccgccccca accccatcc ccgcggttga ccacgatga     180 gcggcagagt cggcgatctg agccccaggc agaaggaggc attggccaag tttcggaga    240 atgtccagga tgtgctgccg ccctgccga tccagatga ctatttctc ctgcgttggc     300 tccgagccag aagcttcgac ctgcagaagt cggaggccat gctccggaag catgtggagt    360
tccgaaagca aaaggacatt gacaacatca ttagctggca gcctccagag gtgatccaac    420
agtatctgtc aggggtatg tgtggctatg acctggatgg ctgcccagtc tggtacgaca    480
taattggacc tctggatgcc aagggtctgc tgttctcagc tccaaacag gacctgctga    540 ggaccaagat gcgggagtgt gagctgcttc tgcaagagtg tgcccaccag accacaaagt    600
tggggaggaa ggtggagacc atcaccataa tttatgactg cgagggggcctt ggcctcaagc    660 atctctggaa gcctgctgtg gaggcctatg agagtttct ctgcatgttt gaggaaaatt     720
atcccgaaac actgaagcgt cttttttgttg ttaaagcccc caaactgttt cctgtggcct     780
ataacctcat caaacccttc ctgagtgagg acactcgtaa gaagatcatg gtcctgggag    840
caaattggaa ggaggtttta ctgaaacata tcagccctga ccaggtgcct gtggagtatg    900
ggggcaccat gactgacccct gatggaaacc ccaagtgcaa atccaagatc aactacgggg    960
gtgacatccc caggaagtat tatgtgcgag accaggtgaa acagcagtat gaacacagcg    1020
tgcagatttc ccgtggctcc tcccaccaag tggagtatga atcctcttcc ctggctgtg    1080 tcctcaggtg gcagtttatg tcagatggag cggatgttgg ttttgggatt ttcctgaaga    1140
ccaagatggg agagaggcag cgggcagggg agatgactaga ggtgctgccc aaccagaggt    1200
acaactccca cctggtccct gaagatggga ccctcacctg cagtgatcct ggcatctgta    1260
agtatctctg ccttggcaat gccttgaagc ccatgtcca gctttctgcc tgtgaggttc    1320
ctcttcctcc atggattttt ggctctgagt gttagaacta gaagtggaat gccatcagtt    1380
caatcctctc cttgtataga tgaagaaatc tagccttgga gacttgttta tggtgaccca    1440
actggttaac agcagggtgg gactttgatc tcatactcct aggtatgggt gagtcacagt    1500
cctaggcgat cacaggggtt caacacgtct gctttctggt ccaggtctaa ctgggtctgt    1560
gactggacag atatttcttg gggatgctcc ttcccagagg tcacagagac agaactggct    1620
```

```
gggtgggcat gggatcacaa ggtaagcaga tgctcaaaag tgcagccttc acccctgagt    1680
ttcactcatc tcccagctga ccaaagaatg gacacagact atgagcaggc agtttacaca    1740
agaatataag aatgggaaac agacatttga aaaggtgctt aatctctctt aactttgtaa    1800
taccattaaa attccccttg actcagcaaa aaaaaaaaaa aaaaa                    1845
```

<210> SEQ ID NO 4
<211> LENGTH: 392
<212> TYPE: PRT
<213> ORGANISM: Homo sapiens

<400> SEQUENCE: 4

```
Met Ser Gly Arg Val Gly Asp Leu Ser Pro Arg Gln Lys Glu Ala Leu
1               5                   10                  15

Ala Lys Phe Arg Glu Asn Val Gln Asp Val Leu Pro Ala Leu Pro Asn
            20                  25                  30

Pro Asp Asp Tyr Phe Leu Leu Arg Trp Leu Arg Ala Arg Ser Phe Asp
        35                  40                  45

Leu Gln Lys Ser Glu Ala Met Leu Arg Lys His Val Glu Phe Arg Lys
    50                  55                  60

Gln Lys Asp Ile Asp Asn Ile Ile Ser Trp Gln Pro Pro Glu Val Ile
65                  70                  75                  80

Gln Gln Tyr Leu Ser Gly Gly Met Cys Gly Tyr Asp Leu Asp Gly Cys
                85                  90                  95

Pro Val Trp Tyr Asp Ile Ile Gly Pro Leu Asp Ala Lys Gly Leu Leu
            100                 105                 110

Phe Ser Ala Ser Lys Gln Asp Leu Leu Arg Thr Lys Met Arg Glu Cys
        115                 120                 125

Glu Leu Leu Leu Gln Glu Cys Ala His Gln Thr Thr Lys Leu Gly Arg
    130                 135                 140

Lys Val Glu Thr Ile Thr Ile Ile Tyr Asp Cys Glu Gly Leu Gly Leu
145                 150                 155                 160

Lys His Leu Trp Lys Pro Ala Val Glu Ala Tyr Gly Glu Phe Leu Cys
                165                 170                 175

Met Phe Glu Glu Asn Tyr Pro Glu Thr Leu Lys Arg Leu Phe Val Val
            180                 185                 190

Lys Ala Pro Lys Leu Phe Pro Val Ala Tyr Asn Leu Ile Lys Pro Phe
        195                 200                 205

Leu Ser Glu Asp Thr Arg Lys Lys Ile Met Val Leu Gly Ala Asn Trp
    210                 215                 220

Lys Glu Val Leu Leu Lys His Ile Ser Pro Asp Gln Val Pro Val Glu
225                 230                 235                 240

Tyr Gly Gly Thr Met Thr Asp Pro Asp Gly Asn Pro Lys Cys Lys Ser
                245                 250                 255

Lys Ile Asn Tyr Gly Gly Asp Ile Pro Arg Lys Tyr Tyr Val Arg Asp
            260                 265                 270

Gln Val Lys Gln Gln Tyr Glu His Ser Val Gln Ile Ser Arg Gly Ser
        275                 280                 285

Ser His Gln Val Glu Tyr Glu Ile Leu Phe Pro Gly Cys Val Leu Arg
    290                 295                 300

Trp Gln Phe Met Ser Asp Gly Ala Asp Val Gly Phe Gly Ile Phe Leu
305                 310                 315                 320

Lys Thr Lys Met Gly Glu Arg Gln Arg Ala Gly Glu Met Thr Glu Val
                325                 330                 335
```

Leu Pro Asn Gln Arg Tyr Asn Ser His Leu Val Pro Glu Asp Gly Thr
                340                 345                 350

Leu Thr Cys Ser Asp Pro Gly Ile Cys Lys Tyr Leu Cys Leu Gly Asn
            355                 360                 365

Ala Leu Lys Pro His Val Gln Leu Ser Ala Cys Glu Val Pro Leu Pro
        370                 375                 380

Pro Trp Ile Phe Gly Ser Glu Cys
385                 390

<210> SEQ ID NO 5
<211> LENGTH: 4055
<212> TYPE: DNA
<213> ORGANISM: Homo sapiens

<400> SEQUENCE: 5

| | |
|---|---|
| gctccctact ccgcctctcg ggatccttta agaggcgggg cttggctgcc agctccgcgg | 60 |
| cccgggcaaa aggctgggac tttactccgg gtggcggcga ggacgagtct gtgctccatc | 120 |
| agctgccgca cccgccgcct cccgccccca aaccccatcc ccgcggttga ccacgatga | 180 |
| gcggcagagt cggcgatctg agccccaggc agaaggaggc attggccaag tttcgggaga | 240 |
| atgtccagga tgtgctgccg gccctgccga atccagatga ctattttctc ctgcgttggc | 300 |
| tccgagccag aagcttcgac ctgcagaagt cggaggccat gctccggaag ttggggagga | 360 |
| aggtggagac catcaccata atttatgact gcgaggggct tggcctcaag catctctgga | 420 |
| agcctgctgt ggaggcctat ggagagtttc tctgcatgtt tgaggaaaat tatcccgaaa | 480 |
| cactgaagcg tcttttttgtt gttaaagccc ccaaactgtt tcctgtggcc tataacctca | 540 |
| tcaaaccctt cctgagtgag gacactcgta agaagatcat ggtcctggga gcaaattgga | 600 |
| aggaggtttt actgaaacat atcagccctg accaggtgcc tgtggagtat gggggcacca | 660 |
| tgactgaccc tgatggaaac cccaagtgca atccaagat caactacggg ggtgacatcc | 720 |
| ccaggaagta ttatgtgcga gaccaggtga acagcagta tgaacacagc gtgcagattt | 780 |
| cccgtggctc ctcccaccaa gtggagtatg agatcctctt ccctggctgt gtcctcaggt | 840 |
| ggcagtttat gtcagatgga gcggatgttg gttttggat tttcctgaag accaagatgg | 900 |
| gagagaggca gcgggcaggg gagatgacag aggtgctgcc caaccagagg tacaactccc | 960 |
| acctggtccc tgaagatggg accctcacct gcagtgatcc tggcatctat gtcctgcggt | 1020 |
| ttgacaacac ctacagcttc attcatgcca agaaggtcaa tttcactgtg gaggtcctgc | 1080 |
| ttccagacaa agcctcagaa gagaagatga acagctgggg gcaggcaccc cgaaataac | 1140 |
| accttctcct atagcaggcc tggcccctc agtgtctccc tgtcaatttc tacccttgt | 1200 |
| agcagtcatt ttcgcacaac cctgaagccc aaagaaactg gctggagga cagacctcag | 1260 |
| gagctttcat ttcagttagg cagaggaaga gcgactgcag tgggtctccg tgtctatcaa | 1320 |
| atacctaagg agtccccagg agctggctgg ccatcgtgat aggatctgtc tgtcctgtaa | 1380 |
| actgtgccaa cttcacctgt ccagggacag cgaagctggg ggtggcgggg gcatgtacc | 1440 |
| acagggtggc agcagggaaa aaaattagaa aagggtgaaa gattgggact taacacttca | 1500 |
| gggaagtcag ctgccgggga gaaacttgct cctaaatgaa cacataagtt tagatcgcaa | 1560 |
| tgaggagtag cagggtagct ggttgctaga gttacggtgg ggatcagaaa ctcttccaaa | 1620 |
| cattttagca ctgaggctgg ggtagctttt ggcttttccc aggtctcagg aggtggcctg | 1680 |
| agtcagcaca catcttccca ctcggtagac aggctggcct ctccctcact ttgagacttt | 1740 |

```
ggcaactcct gggccacacg gcctgcctct ttgattacta atgattgtca gtgactcaga    1800
gcttcctggg acttcgggta cccacccgct gttctccatg caaacaaagc gccagggaaa    1860
tgacccacag ggatcgcagc tgcagggagg gccagggagg ttgggggtgg gagtgaatgc    1920
taaaagcaga tcgtccagtg ccctttttcag tgctaccggc ctctcaccaa gcagtcctcc    1980
atgtgagcaa ccccgagaca aaaatgctaa gtgggatcaa gagagcagca ctcggagagg    2040
gtgtttgcca gtctgagtgt cccgcggtgc ccgccaaccc gcttcctgac tgacctgagc    2100
aaggtcttac taagcagtcc catctctgtg ggaggcatgc aacgcgtgca gggagttcag    2160
gtgccggtcg gcgtagccag gcctggaggc cccccaggca ggaggccgcc caaaggcggg    2220
gccggcgtct cgcagactag gggctggggg cggccacaga cggcctcgaa accacagccc    2280
ttaccccaat cccacgagcc ccgccaacga accacaggtg ctgggcttta gaacatgg      2340 gaaggcggcc ccagacctgg cgggaacgcc tttccctcag agccaggccc cggccccgtc    2400
tgggaagctc atcttgcgaa gctgaggag ctcagggcaa aggccaggct agcgcggacc     2460
ggaaggggcc gaggctgcac gggcctctgc cagaacgctc aggacatccc ggcctgggtt    2520
tacaacgctg ttaggaaaat taaccaatga ataaagcaac gttcagtgcg cagggagtga    2580
aattcaatgc ccaccgctag gctcctcgct gcctctcact caagaggccc aaactcagac    2640
ggcgtcaggg acccggaccc agcagccgtt tcacgccaat agatagggcg catgcgcaga    2700
aatcctcctc ggctctctag cgtgagcttt cccaaggggc cacgcccagc ttgccttctg    2760
attggtccag ctggtgggtt gtcttccgcc atctttgatc agggcactaa ggatgctccc    2820
cacggccttc acagtgacgg cggagaccct gccccgccag ctgctcagta cgtgccgcgt    2880
agcccgtgcg agccaagtgt gagtccgggc gagcgcctgc ggagctagca ctgggcccag    2940
aatgagaggg aggcggagga gcagcgatca cgtggtttta gggactgtct aataattcca    3000
cgccagcatt gccggtgttt cagggggtgg gaaccgctgc gttccccatc aacttttctc    3060
ccacccacca ccctccccaa cctacaagcc cagctcagct tgaggtaact gctgaccgga    3120
ctgtcctata cagccctaca agacagaggc cctagggct gaaagcgggg gcctccgtag     3180
ggagccagcg ggggcctcaa tagttactca ttttctctac ctttgatgaa ataagagct    3240 aattcttaat aaggcctacc gggtatcacg caaaaccct gtgcttacta ttacactttg     3300
ggttgttgca aagattaaag gaaataagcc gtgcaaagcg cttaagagct tggtataagt    3360
aagtgctcgt caatgttggc tactctcatt ttttttgcag acgtgggaac tggggctcag    3420
ggaggctaac agccagtagg cggcacagct aggatttgaa cccaggattg tctccaacgc    3480
cgctcaatta tacccgccaa ggagtcacag agacttagtg aagtgcacac attgctcacc    3540
tgggtgaact gaggtccagc gggggaaggc ttcctcctgt tgtaatcact aaccccaact    3600
ctgtctccct tgcccgattc attcattcgt taattaattc atccaacatc ctgtccccaa    3660
gaagctcagt ctggggacat actgatccag ttaaatgcga gtgcttccta gttatacatg    3720
gcgactgctg agaagggact ccagagtcca ggcacctacc tcccaggggc tcaccgttca    3780
ctcctctagc ctcatttaga gctcgcatta agagcacggg atctggatcc acactgtttg    3840
gattcaaatc acaacttcac cacttagcag ctgtgtgttc tgggaaaatg acccaccttc    3900
tctgtgcctc cattttctca cctgtaaaac gggctcccag gctggtggga gggtttcagg    3960
tgtaagacat ggagagtcct ttagcgaaca tgtagactgg caataaactc aataaatggt    4020
gactgttata attaaaaaaa aaaaaaaaa aaaaa                                4055
```

<210> SEQ ID NO 6
<211> LENGTH: 320
<212> TYPE: PRT
<213> ORGANISM: Homo sapiens

<400> SEQUENCE: 6

```
Met Ser Gly Arg Val Gly Asp Leu Ser Pro Arg Gln Lys Glu Ala Leu
1               5                   10                  15

Ala Lys Phe Arg Glu Asn Val Gln Asp Val Leu Pro Ala Leu Pro Asn
            20                  25                  30

Pro Asp Asp Tyr Phe Leu Leu Arg Trp Leu Arg Ala Arg Ser Phe Asp
        35                  40                  45

Leu Gln Lys Ser Glu Ala Met Leu Arg Lys Leu Gly Arg Lys Val Glu
    50                  55                  60

Thr Ile Thr Ile Ile Tyr Asp Cys Glu Gly Leu Gly Leu Lys His Leu
65                  70                  75                  80

Trp Lys Pro Ala Val Glu Ala Tyr Gly Glu Phe Leu Cys Met Phe Glu
                85                  90                  95

Glu Asn Tyr Pro Glu Thr Leu Lys Arg Leu Phe Val Val Lys Ala Pro
            100                 105                 110

Lys Leu Phe Pro Val Ala Tyr Asn Leu Ile Lys Pro Phe Leu Ser Glu
        115                 120                 125

Asp Thr Arg Lys Lys Ile Met Val Leu Gly Ala Asn Trp Lys Glu Val
    130                 135                 140

Leu Leu Lys His Ile Ser Pro Asp Gln Val Pro Val Glu Tyr Gly Gly
145                 150                 155                 160

Thr Met Thr Asp Pro Asp Gly Asn Pro Lys Cys Lys Ser Lys Ile Asn
                165                 170                 175

Tyr Gly Gly Asp Ile Pro Arg Lys Tyr Tyr Val Arg Asp Gln Val Lys
            180                 185                 190

Gln Gln Tyr Glu His Ser Val Gln Ile Ser Arg Gly Ser Ser His Gln
        195                 200                 205

Val Glu Tyr Glu Ile Leu Phe Pro Gly Cys Val Leu Arg Trp Gln Phe
    210                 215                 220

Met Ser Asp Gly Ala Asp Val Gly Phe Gly Ile Phe Leu Lys Thr Lys
225                 230                 235                 240

Met Gly Glu Arg Gln Arg Ala Gly Glu Met Thr Glu Val Leu Pro Asn
                245                 250                 255

Gln Arg Tyr Asn Ser His Leu Val Pro Glu Asp Gly Thr Leu Thr Cys
            260                 265                 270

Ser Asp Pro Gly Ile Tyr Val Leu Arg Phe Asp Asn Thr Tyr Ser Phe
        275                 280                 285

Ile His Ala Lys Lys Val Asn Phe Thr Val Glu Val Leu Leu Pro Asp
    290                 295                 300

Lys Ala Ser Glu Glu Lys Met Lys Gln Leu Gly Ala Gly Thr Pro Lys
305                 310                 315                 320
```

<210> SEQ ID NO 7
<211> LENGTH: 9043
<212> TYPE: DNA
<213> ORGANISM: Homo sapiens

<400> SEQUENCE: 7

```
accagaaaac gctctgcggc tagagcttca gcacaggctg ggtctgctgt gccgggtctg    60
tatggggaca gctgcacgcc tcttccgctt gtgtgagaac aaaggccgga acctggattc   120
```

-continued

```
tgatccaaac cccctggccc ccaccttctg ggatgttagc agagccttt  aactggcacc    180 caggcatgtg gaatatgctc atagtggcga tgtgcttggc ccttctgggc tgcctgcaag    240
cccaggagct ccagggacat gtctccataa tcctgctggg agcaactggg gacctggcta    300
agaagtactt atggcaggga ctgttccagc tgtacctgga tgaagcgggg aggggtcaca    360
gttttagctt ccatggagct gctctgacag cccccaagca gggtcaagag ctcatggcca    420
aggccctgga atccctctcc tgccccaagg acatggcacc cagtcactgt gcagagcaca    480
aggatcagtt cctgcagctg agccagtacc gccaactgaa gacggccgag gactatcagg    540
ccctgaacaa ggacatcgag gcacagctcc agcacgcagg cctccgggag ctggcagga    600 tcttctactt ctcagtgcca cccttcgcct atgaagacat tgcccgcaac atcaacagta    660
gctgccggcc aggcccgggc gcctggctgc gggttgtcct tgagaaaccc tttggccatg    720
accacttctc agcccagcag ctggccacag aactcgggac ctttttccag gaggaggaga    780
tgtaccgggt ggaccattac ttaggcaagc aggctgtggc gcagatcctg cctttccgag    840
accagaaccg caaggctttg gacggcctct ggaaccggca ccatgtggag cgggtggaga    900
tcatcatgaa agagaccgtg gatgctgaag ccgcaccag cttctatgag gagtacggtg    960
tcattcgcga cgtcctccag aaccatctga cggaggtcct caccctcgtg gccatggagc   1020
tgccccacaa tgtcagcagt gcggaggctg tgctgcggca caagcttcag gtcttccagg   1080
cgctgcgggg cctgcagagg ggcagtgccg tcgtgggcca gtaccagtct tacagtgagc   1140
aggtgcgcag agagctgcag aagccagaca gcttccacag cctgacgccg accttcgcag   1200
ccgtcctagt gcacattgac aaccttcgct gggagggcgt gccttcatc ctgatgtctg    1260 gcaaagcctt ggacgagaga gtgggctacg ctcggatctt gttcaagaac caggcctgct   1320
gtgtgcagag cgaaaagcac tgggccgcg cgcagagcca gtgcctgccc cggcagctcg   1380
tcttccacat cggccatggc gacctgggca gccctgccgt gctggtcagc aggaacctgt   1440
tcaggccctc cctgccctcc agctggaagg aaatggaggg accacctggg ctccgccttt   1500
tcggcagccc tctgtccgat tactacgcct acagccctgt gcgggagcgg gacgcccact   1560
ccgtcctctt atcccatatc ttccatggcc ggaagaattt cttcatcacc acagagaact   1620
tgctggcctc ctggaacttc tggaccccctc tgctggagag cctggcccat aaggccccac   1680
gcctctaccc tggaggagct gagaatggcc gtctgttgga cttgagttc agtagcggcc   1740 ggttgttctt ttcccagcag cagccggagc agctggtgcc agggccaggg ccggcccaa   1800 tgcccagtga cttccaggtc ctcagggcca agtaccgaga gagcccgctg gtctccgcct   1860
ggtccgagga gctgatctct aagctggcta atgacatcga ggccaccgct gtgcgagccg   1920
tgcggcgctt tggccagttc cacctggcac tgtcgggggg ctcgagcccc gtggccctgt   1980
tccagcagct ggccacggcg cactatggct tccctgggc ccacacgcac ctgtggctgg   2040
ttgacgagcg ctgcgtccca ctctcagacc cggagtccaa cttccagggc ctgcaggccc   2100
acctgctgca gcacgtccgg atcccctact acaaacatcca ccccatgcct gtgcacctgc   2160
agcagcggct ctgcgccgag gaggaccagg cgcccagat ctatgccagg gagatctcag   2220
ccctggtggc caacagcagc ttcgacctgg tgctgctggg catgggtgcc gacgggcaca   2280
cagcctccct cttcccacag tcacccactg gcctggatgg cgagcagctg gtcgtgctga   2340
ccacgagccc ctcccagcca caccgccgca tgagccttag cctgcctctc atcaaccgcg   2400
ccaagaaggt ggcagtcctg gtcatgggca ggatgaagcg tgagatcacc acgctggtga   2460
gccgggtggg ccatgagccc aagaagtggc ccatctcggg tgtcctgccg cactccggcc   2520
```

```
agctggtgtg gtacatggac tacgacgcct tcctgggatg agggcgcctg tgcccttgc    2580 ccgcttcgct cctgtgcttt ccttcgcccg tgtcttccct cccttctcgg ccccgccacc    2640
tgcccagcgt gccctggctc tccagaacct tctatcccac agtcaggccc cagagagggc    2700
aggacaagcc ttgtcccgat gcctttgacc ggcagtctg tgtattggtg gatagatgca     2760
gaaacaagga agaaatggag tctgctcctg agaagcttca aattcaggcc aggagagaag    2820
tcttaagaaa agacctccag cagttacaca ttcatatcaa ccagcacaac acggatggc     2880 gcccaaactc cggcgttcac aagaggagac gtgacgtggt gggctgaggt taatcaggga    2940
aggtttcctg ggggaggtga tccttgaact ggctcccggg gaacattcag agcatgattg    3000
gtagacagaa gggtgcagag gcgcccaggg gagtacattg ccccgtgcaa agcagggca    3060 ttggggactg tcttgagacc ctgaggggt caagcccctc cttccccagc tgcccctcct     3120
tctagaacct ctgcacatct agcctctggc cctcctcttc actgcctcca cctgctcccg    3180
cttgccatcc ctgtctcctc catcctggct gtgcagtagg aattccaggc tcctccctgt    3240
gtctttgctg ttcttcagac tccatttata gagaatgagg gctgataaca ggaatacagt    3300
ggcaaagact agactgtgga aagggttcca gaaatctttt ttcttttttta attaaaaaaa   3360 atatttgcag agatgagctc ttgctatgtt gcccaggctg gtctcaaact cctgggctca    3420
agcgatcctc ccatctcagc ctcccagagt gctgggatta caggtgtgag ctactgcgcc    3480
cagccccaga aatctcagtg ctgtttggag ctccatttct catttgatga cttgctctgc    3540
gtggggaggt ggggtctcat tcccccaact tcctcaggga ggaccctgc cctccgctgc     3600 tcctctgtcc tgctagcctt cctccaggaa gcacactggg tgcagataat caggacattc    3660
cagagatccc caatttaaga gggtcatttc catctcaggg gactcccgga tgggtgtttc    3720
cgctctcaat agcccctctt gttttaccag gaaagatcca gttaaatcac ccactgaggt    3780
gacagctcat tagcggggag agagatggag catcgagtga cactgggcca tccaggcggc    3840
tctgctccca ccagacagga gctaggcctc actggcaggg gggctgccca cagccttttc    3900
aggggctcgc ttggcgggtg acggggccgc agccaggcct tctctccctg ccccttggtg    3960
accccgtggc ttcctgtctg ctggcctctc ctgctactta tcacttcacc acgaactctc    4020
tgcctgagac tggggaagta agcgggtatc ttctcagtga gcataggttg gggactgtga    4080
tcttgagaag ccatgggcca gcaataccag cttttctgaa gccccaagg agggctctga    4140 cattcttttt aaaaacacca caaagcaaaa ttcccaggac atgtgtagtt ttgtttgttc    4200
agtatcccac aacttaaggc tgggagatgg aactcttggt taaggtcgat ttttctgtct    4260
ggcttctccg caccttccac ttgctctctg gatcaggcag atataaactt tctagcgcat    4320
tttgagagag ggctttcttg ggtgagggag catggcaaag tcggtttctc tctgactgt    4380 ttacacttca aggcggtgga tttagaggaa tcctggcttt cattttcaat gccagtctga    4440
gacatgttcc caagccgggg ctcttgttca caccacttac tctggccacc aacaacaacc    4500
caggccagac agagcatctc tttttttttt ttttgagaca gagtctctgt cgcccaggct    4560
ggagcccagt ggcgagatct tggctcacta caacctccac ctcccgggtt caggcaattc    4620
tcgtgcctaa gcctcccgag tagctgcgac tacaggcgcc ggccagcatg cctgtctaat    4680
ttttgtattt tagtagagac agggtttcac catgttgccc aggctggtct cgaactcctg    4740
agctcaggca gtctacccac ctcagcctcc caaagtgctg ggattacagg cgtgagccac    4800
cgcgcccagc cagaacatct gttttacac ccagagagcg cccctcgtta ggacagaacc     4860
acggtgccca gagccaggaa gccgccctcc tggcgcccag catctgagct tctacacgtg    4920
```

```
atgggcgggc tcaggagagg acagggagtc gtggtggaag ttccacagct ggccgcgtgg    4980
gggggccctt gcaccgcact gccgcctcct gactgcccct atccccgcag cccctgtgcc    5040
ggatttcatt tccctcctct ctcccagggt acctggcccc agcactctcc catctgttct    5100
tcaggaaccg actcctctcc agttgcaaca ccagggagaa aggggcctcc acatgcccaa    5160
gtacccctgc aggatgaagg gcaggccggc ccttgatgtg ccatttctga ataatagtca    5220
ctgccgccga gtctaggatg tcctgttcta actcagccct gcctcggatg caccaccgat    5280
ctgtgcagag tgggtgtggg agtgtgggtg agggtcgaaa tgccaaaggt ctactttcca    5340
gaatcaagtg ccttctgcaa atcatgttgg aaaagtccaa acctggagat gtccctgtgc    5400
ctccgcccct acccacccct tttccttcag ctgtgttagg aaggagaagt tttcagaacc    5460
ctctaggctg gtggctttca aacttcagac catgatctgc agcaagaaac gtgccttcca    5520
tcataaatca gtccatttgt ttacaactgt gttccaagca ggtttcataa agaaattctt    5580
aaccttagaa cctcggatat cctctatgtt ttagttttca ttttttttaaa atgcttctta    5640
aaattcacta aattgggcta ggtgtggctc atgcctgtaa tcccagcact atgggaggct    5700
gaggtgagag gatcacttga gcccagaagg ttgaaaccag cctgggcaac atagtgagac    5760
cccatctcta caaaaagttt taaaaccagg tatggtggtg ccctcctgtg gtcccagcta    5820
ctcgggagtc tgaggtggga ggatcacctg agcccaggag actgaggctg cagtaaggtg    5880
tgattgcact attgctctct agcctggaaa acagagtgag accctatctc aaaaaaaaaa    5940
aaaaaaaaaa aggaaagagt gatgacaaca gcccagggag cagccccgct cagaacccaa    6000
gtcccaagtt ccagcactgt gttcccaggc aggctgtttg cctcttcctg gtctggaagc    6060
ccttgggtcc tatggtggcg gcagctccca cagtccaggt tccctggtgg ggaccaatga    6120
ttccatccgc atgaagccca cgtgtgcac ttaggggccc ataaatggca gaagggcccc    6180
tcctttggga gaccttgtca gtcagcatct ctagggcaac cgtgattgcc atttgtagag    6240
gggaaggaat caagggactt taagctagat caaaatctgg ggacaaattc tcctgctaac    6300
tgcaagttaa aataggccct tcttactgaa tttccctgtt tgtttctctg cagacaatgc    6360
tttagcccta ctcttgggcc cccaagttag cagagtaatc aaagcttcct accgtttggc    6420
ctactattcc agactagtcc ctcgagggt tcccttccaa aatatgcagg gctcaggctc    6480
ccaattccgg gcctgtctgc tttgcttgtg tttctcctgt ccctgttctc ccggagggcc    6540
caggtggaac tcacgacagg gagggagacg cttcccaaaa acctgcaggg ctatttccca    6600
gaatttggtt ttcaagtaca aaacttttg tcctgtaaga tatatgcagc ctcacagaag    6660
cagcctctgc ctccactta ccagctacgt ttttatctta agcacatggg gctcccttag    6720
aacttactcc actgatttaa aaaaaaaaaa ctgcctggca gcatctcagt gtcagagtga    6780
gcacggcaca ggaaaggccc gtggtgacga gggtgaggtg gccacagtga ccggacgaca    6840
aatgagactc tgcaaatgag actccagagg gtgaagatct gcggtctcca gacatcatag    6900
gccatgtgac ccactagggg ccgcttaccc ctggccgtcc gctggctgaa ctgaacgcat    6960
tccctctctc cgcaactctc ccgtgaggct gcacccgtgt gggtagcact ggaagcggca    7020
ctgtttgcat tgtacatagg aaggaaggaa gttcttccag cctcaccagc acctggcagc    7080
gagtcagagc ctgtgagggc atccgaagca gtgatgcagt gtcaacctcc cagctggtgc    7140
cactctgccc tcgggggctc caagcattgt aactcagtca tgggagctgc ctctttggaa    7200
gtgcagattt attcctgtaa taatcctgcc tgcttttacc tctcgtccac tgaccagcaa    7260
gtgtgagtcc cggtgtcagt cggcacagtc cagtgtccat ctgcatttgc tcatgcagag    7320
```

-continued

| | |
|---|---|
| ggggtgagtt gggcactccc tgttgttggt tttccttttg cagcacactg ggcagtctcc | 7380 |
| ctataaaaca aaaccccac cttctgtgcc ttctgcttta gagcagagct ccccctccca | 7440 |
| tttcctcagt cttccctgca aaatctgtcc accggggaag gcagcaggaa ccctgggcag | 7500 |
| cgggtgttct gggaaggcta gtgacagcag atgtcatcca ggaacagcca cacacggttc | 7560 |
| tccaggccgc cgtcagcagc tcaaggtggg gtatgagtga aagctgagg atctcgcagc | 7620 |
| ttgttgctga gcaaggtgca accgggctca tgctgtcatc agcacaagac gggatggcaa | 7680 |
| gggctttcag acgcatttcc aagagtccag caagccaggg ggaagatgat cccttttgccg | 7740 |
| aagtgtaccc tctagccaac ttttgggagc gcttctgttt gcaaagcgct ggggatgtgc | 7800 |
| ctgtctctgt gtgacccacg aacgggaagg gagagcactg gagtaatgac acttctgctg | 7860 |
| ctgctttgat tctcaaggct gatctttaaa accctcgcct tgctgacagg tgctttaaag | 7920 |
| gcagtctgca tcttttcttc ccttggtgtg ggagaggtaa acactttgat ttgctgaaag | 7980 |
| ctgtatggag tatatttgaa cagctagtag ttagctttga aagtggaagt gtgaacagac | 8040 |
| actacttgtg tcgctttggg tccttcactt tacccccaca gaagtctaga ggcgtctgtt | 8100 |
| ataaagcgtt acggggcgcc tgcatgcagg aggaaggacc tgtattagct ggaaatcatc | 8160 |
| aggaacccag cttgcctcca tctctctgag atgtgctggg tacagcctgc ccctcctagt | 8220 |
| tctgtccacc gggaagagcc ggctggcggc agatccccag gggcagagcc cctgctggat | 8280 |
| cctgggagct catctttacc tgtgccgag tgggaactgt gattccagcc gggcaggtca | 8340 |
| gagtggagca gtgctaagag gctgttgcag gagaactaga cgggcggggc ctgctgcatc | 8400 |
| tggatcatgt ttctgtgctc tgccccgcgc tagggactca gggtctgggc ttctgccagg | 8460 |
| tgaggagcag agagactgtt cccttgggtg gagaggtgtg ggcatgagag ccacccattg | 8520 |
| ccaagcagca agaatgttcg tgctttttttc cagagagggg aaccccactg gttttttgtgg | 8580 |
| aaacaatgga aacttacaga tgcctgcctg ggatgatgag gcacattcag aacaaatgct | 8640 |
| ttttttttttt tgagacagag tctcgctctg acgcccaggc tggagtgcag tggcgcgatc | 8700 |
| tcggctcact gcaaactttg cctcccaggt tcaagtgatt ctcctacctc agcctcccga | 8760 |
| gtagctggga ttacaccacc atgcccagca aattttgtg ttttagtag agacggagtt | 8820 |
| tcaccatgtt ggccaggctg gtctcgaact cctgacctca ggtgatccat ccgccttggc | 8880 |
| ctcccaaagt gctgggatta caggcgggag ccaccatgcc tggccagaac aaatgccttt | 8940 |
| ttaaaccttt taagaacatt tttaaaatgt ctttttctat gtcaaatgta acgtttattt | 9000 |
| ttttaaacaa taaaattgat ttgccaaaaa aaaaaaaaaa aaa | 9043 |

<210> SEQ ID NO 8
<211> LENGTH: 802
<212> TYPE: PRT
<213> ORGANISM: Homo sapiens

<400> SEQUENCE: 8

Met Leu Ala Glu Pro Phe Asn Trp His Pro Gly Met Trp Asn Met Leu
1               5                   10                  15

Ile Val Ala Met Cys Leu Ala Leu Leu Gly Cys Leu Gln Ala Gln Glu
            20                  25                  30

Leu Gln Gly His Val Ser Ile Ile Leu Leu Gly Ala Thr Gly Asp Leu
        35                  40                  45

Ala Lys Lys Tyr Leu Trp Gln Gly Leu Phe Gln Leu Tyr Leu Asp Glu
    50                  55                  60

-continued

```
Ala Gly Arg Gly His Ser Phe Ser Phe His Gly Ala Ala Leu Thr Ala
 65                  70                  75                  80

Pro Lys Gln Gly Gln Glu Leu Met Ala Lys Ala Leu Glu Ser Leu Ser
                 85                  90                  95

Cys Pro Lys Asp Met Ala Pro Ser His Cys Ala Glu His Lys Asp Gln
            100                 105                 110

Phe Leu Gln Leu Ser Gln Tyr Arg Gln Leu Lys Thr Ala Glu Asp Tyr
        115                 120                 125

Gln Ala Leu Asn Lys Asp Ile Glu Ala Gln Leu Gln His Ala Gly Leu
    130                 135                 140

Arg Glu Ala Gly Arg Ile Phe Tyr Phe Ser Val Pro Pro Phe Ala Tyr
145                 150                 155                 160

Glu Asp Ile Ala Arg Asn Ile Asn Ser Ser Cys Arg Pro Gly Pro Gly
                165                 170                 175

Ala Trp Leu Arg Val Val Leu Glu Lys Pro Phe Gly His Asp His Phe
            180                 185                 190

Ser Ala Gln Gln Leu Ala Thr Glu Leu Gly Thr Phe Phe Gln Glu Glu
        195                 200                 205

Glu Met Tyr Arg Val Asp His Tyr Leu Gly Lys Gln Ala Val Ala Gln
    210                 215                 220

Ile Leu Pro Phe Arg Asp Gln Asn Arg Lys Ala Leu Asp Gly Leu Trp
225                 230                 235                 240

Asn Arg His His Val Glu Arg Val Glu Ile Met Lys Glu Thr Val
                245                 250                 255

Asp Ala Glu Gly Arg Thr Ser Phe Tyr Glu Glu Tyr Gly Val Ile Arg
            260                 265                 270

Asp Val Leu Gln Asn His Leu Thr Glu Val Leu Thr Leu Val Ala Met
        275                 280                 285

Glu Leu Pro His Asn Val Ser Ser Ala Glu Ala Val Leu Arg His Lys
    290                 295                 300

Leu Gln Val Phe Gln Ala Leu Arg Gly Leu Gln Arg Gly Ser Ala Val
305                 310                 315                 320

Val Gly Gln Tyr Gln Ser Tyr Ser Glu Gln Val Arg Arg Glu Leu Gln
                325                 330                 335

Lys Pro Asp Ser Phe His Ser Leu Thr Pro Thr Phe Ala Ala Val Leu
            340                 345                 350

Val His Ile Asp Asn Leu Arg Trp Glu Gly Val Pro Phe Ile Leu Met
        355                 360                 365

Ser Gly Lys Ala Leu Asp Glu Arg Val Gly Tyr Ala Arg Ile Leu Phe
    370                 375                 380

Lys Asn Gln Ala Cys Cys Val Gln Ser Glu Lys His Trp Ala Ala Ala
385                 390                 395                 400

Gln Ser Gln Cys Leu Pro Arg Gln Leu Val Phe His Ile Gly His Gly
                405                 410                 415

Asp Leu Gly Ser Pro Ala Val Leu Val Ser Arg Asn Leu Phe Arg Pro
            420                 425                 430

Ser Leu Pro Ser Ser Trp Lys Glu Met Glu Gly Pro Gly Leu Arg
        435                 440                 445

Leu Phe Gly Ser Pro Leu Ser Asp Tyr Tyr Ala Tyr Ser Pro Val Arg
    450                 455                 460

Glu Arg Asp Ala His Ser Val Leu Leu Ser His Ile Phe His Gly Arg
465                 470                 475                 480
```

-continued

```
Lys Asn Phe Phe Ile Thr Thr Glu Asn Leu Leu Ala Ser Trp Asn Phe
                485                 490                 495

Trp Thr Pro Leu Leu Glu Ser Leu Ala His Lys Ala Pro Arg Leu Tyr
            500                 505                 510

Pro Gly Gly Ala Glu Asn Gly Arg Leu Leu Asp Phe Glu Phe Ser Ser
            515                 520                 525

Gly Arg Leu Phe Phe Ser Gln Gln Pro Glu Gln Leu Val Pro Gly
530                 535                 540

Pro Gly Pro Ala Pro Met Pro Ser Asp Phe Gln Val Leu Arg Ala Lys
545                 550                 555                 560

Tyr Arg Glu Ser Pro Leu Val Ser Ala Trp Ser Glu Glu Leu Ile Ser
                565                 570                 575

Lys Leu Ala Asn Asp Ile Glu Ala Thr Ala Val Arg Ala Val Arg Arg
            580                 585                 590

Phe Gly Gln Phe His Leu Ala Leu Ser Gly Gly Ser Ser Pro Val Ala
            595                 600                 605

Leu Phe Gln Gln Leu Ala Thr Ala His Tyr Gly Phe Pro Trp Ala His
            610                 615                 620

Thr His Leu Trp Leu Val Asp Glu Arg Cys Val Pro Leu Ser Asp Pro
625                 630                 635                 640

Glu Ser Asn Phe Gln Gly Leu Gln Ala His Leu Leu Gln His Val Arg
                645                 650                 655

Ile Pro Tyr Tyr Asn Ile His Pro Met Pro Val His Leu Gln Gln Arg
            660                 665                 670

Leu Cys Ala Glu Glu Asp Gln Gly Ala Gln Ile Tyr Ala Arg Glu Ile
            675                 680                 685

Ser Ala Leu Val Ala Asn Ser Ser Phe Asp Leu Val Leu Leu Gly Met
690                 695                 700

Gly Ala Asp Gly His Thr Ala Ser Leu Phe Pro Gln Ser Pro Thr Gly
705                 710                 715                 720

Leu Asp Gly Glu Gln Leu Val Val Leu Thr Thr Ser Pro Ser Gln Pro
                725                 730                 735

His Arg Arg Met Ser Leu Ser Leu Pro Leu Ile Asn Arg Ala Lys Lys
            740                 745                 750

Val Ala Val Leu Val Met Gly Arg Met Lys Arg Glu Ile Thr Thr Leu
            755                 760                 765

Val Ser Arg Val Gly His Glu Pro Lys Lys Trp Pro Ile Ser Gly Val
770                 775                 780

Leu Pro His Ser Gly Gln Leu Val Trp Tyr Met Asp Tyr Asp Ala Phe
785                 790                 795                 800

Leu Gly
```

<210> SEQ ID NO 9
<211> LENGTH: 9117
<212> TYPE: DNA
<213> ORGANISM: Homo sapiens

<400> SEQUENCE: 9

```
tgaggcctga ggcctggggc ggggtggcgg ccgggctggc cttggcctcg cgccttcccc      60
tgcggccgcc gcgggctccg cgggcggtat cggagtgtcg tgcggcgcgt ggccgcgtga     120
cacgcgcact tgtcggagtg acgggccctg cggaagagga ggtgcggccc agggcgcagg     180
ggagccctcg ggagcgggcc cggccctcag cgccgccccg gccgtgtccc ggaggagcgg     240
cctgcgccgc cgcgcgagag gaagcaccca ggcatgtgga atatgctcat agtggcgatg     300
```

```
tgcttggccc ttctgggctg cctgcaagcc caggagctcc agggacatgt ctccataatc    360
ctgctgggag caactgggga cctggctaag aagtacttat ggcagggact gttccagctg    420
tacctggatg aagcggggag gggtcacagt tttagcttcc atggagctgc tctgacagcc    480
cccaagcagg gtcaagagct catggccaag gccctggaat ccctctcctg ccccaaggac    540
atggcaccca gtcactgtgc agagcacaag gatcagttcc tgcagctgag ccagtaccgc    600
caactgaaga cggccgagga ctatcaggcc ctgaacaagg acatcgaggc acagctccag    660
cacgcaggcc tccgggaggc tggcaggatc ttctacttct cagtgccacc cttcgcctat    720
gaagacattg cccgcaacat caacagtagc tgccggccag cccgggcgc ctggctgcgg    780 gttgtccttg agaaacccttt tggccatgac cacttctcag cccagcagct ggccacagaa    840
ctcgggacct ttttccagga ggaggagatg taccgggtgg accattactt aggcaagcag    900
gctgtggcgc agatcctgcc tttccgagac cagaaccgca aggctttgga cggcctctgg    960
aaccggcacc atgtggagcg ggtggagatc atcatgaaag agaccgtgga tgctgaaggc   1020
cgcaccagct tctatgagga gtacggtgtc attcgcgacg tcctccagaa ccatctgacg   1080
gaggtcctca ccctcgtggc catggagctg ccccacaatg tcagcagtgc ggaggctgtg   1140
ctgcggcaca agcttcaggt cttccaggcg ctgcggggcc tgcagagggg cagtgccgtc   1200
gtgggccagt accagtctta cagtgagcag gtgcgcagag agctgcagaa gccagacagc   1260
ttccacagcc tgacgccgac cttcgcagcc gtcctagtgc acattgacaa ccttcgctgg   1320
gagggcgtgc ctttcatcct gatgtctggc aaagccttgg acgagagagt gggctacgct   1380
cggatcttgt tcaagaacca ggcctgctgt gtgcagagcg aaaagcactg gccgcggcg   1440 cagagccagt gcctgccccg gcagctcgtc ttccacatcg ccatggcgga cctgggcagc   1500
cctgccgtgc tggtcagcag gaacctgttc aggccctccc tgccctccag ctggaaggaa   1560
atggagggac cacctgggct ccgccttttc ggcagccctc tgtccgatta ctacgcctac   1620
agccctgtgc gggagcggga cgcccactcc gtcctcttat cccatatctt ccatggccgg   1680
aagaatttct tcatcaccac agagaacttg ctggcctcct ggaacttctg gaccccctctg   1740 ctggagagcc tggcccataa ggccccacgc ctctaccctg gaggagctga gaatggccgt   1800
ctgttggact ttgagttcag tagcggccgg ttgttctttt cccagcagca gccggagcag   1860
ctggtgccag ggccagggcc ggccccaatg cccagtgact ccaggtcct cagggccaag   1920 taccgagaga gcccgctggt ctccgcctgg tccgaggagc tgatctctaa gctggctaat   1980
gacatcgagg ccaccgctgt gcgagccgtg cggcgctttg ccagttcca cctggcactg   2040 tcgggggggct cgagccccgt ggccctgttc cagcagctgg ccacggcgca ctatggcttc   2100
ccctgggccc acacgcacct gtggctggtt gacgagcgct gcgtcccact ctcagacccg   2160
gagtccaact tccagggcct gcaggccac ctgctgcagc acgtccggat cccctactac   2220
aacatccacc ccatgcctgt gcacctgcag cagcggctct gcgccgagga ggaccagggc   2280
gcccagatct atgccaggga gatctcagcc ctggtggcca acagcagctt cgacctggtg   2340
ctgctgggca tgggtgccga cgggcacaca gcctccctct tcccacagtc acccactggc   2400
ctggatggcg agcagctggt cgtgctgacc acgagcccct cccagccaca ccgccgcatg   2460
agccttagcc tgcctctcat caaccgcgcc aagaaggtgg cagtcctggt catgggcagg   2520
atgaagcgtg agatcaccac gctggtgagc cgggtgggcc atgagcccaa gaagtggccc   2580 atctcggtg tcctgccgca ctccggccag ctggtgtggg acatggacta cgacgccttc   2640
ctgggatgag ggcgcctgtg cccccttgccc gcttcgctcc tgtgcttccc ttcgcccgtg   2700
```

```
tcttccctcc cttctcggcc ccgccacctg cccagcgtgc cctggctctc cagaaccttc   2760
tatcccacag tcaggcccca gagagggcag gacaagcctt gtcccgatgc ctttgaccgg   2820
cagctctgtg tattggtgga tagatgcaga aacaaggaag aaatggagtc tgctcctgag   2880
aagcttcaaa ttcaggccag gagagaagtc ttaagaaaag acctccagca gttacacatt   2940
catatcaacc agcacaacac gggatggcgc ccaaactccg gcgttcacaa gaggagacgt   3000
gacgtggtgg gctgaggtta atcagggaag gtttcctggg ggaggtgatc cttgaactgg   3060
ctcccgggga acattcagag catgattggt agacagaagg gtgcagaggc gcccagggga   3120
gtacattgcc ccgtgcaaag caggggcatt ggggactgtc ttgagaccct gaggggtca    3180 agcccctcct tccccagctg cccctccttc tagaacctct gcacatctag cctctggccc   3240
tcctcttcac tgcctccacc tgctcccgct tgccatccct gtctcctcca tcctggctgt   3300
gcagtaggaa ttccaggctc ctccctgtgt ctttgctgtt cttcagactc catttataga   3360
gaatgagggc tgataacagg aatacagtgg caaagactag actgtggaaa gggttccaga   3420
aatctttttt ctttttttaat taaaaaaaat atttgcagag atgagctctt gctatgttgc   3480
ccaggctggt ctcaaactcc tgggctcaag cgatcctccc atctcagcct cccagagtgc   3540
tgggattaca ggtgtgagct actgcgccca gccccagaaa tctcagtgct gtttggagct   3600
ccatttctca tttgatgact tgctctgcgt ggggaggtgg ggtctcattc ccccaacttc   3660
ctcagggagg accccctgccc tccgctgctc ctctgtcctg ctagccttcc tccaggaagc   3720
acactgggtg cagataatca ggacattcca gagatcccca atttaagagg gtcatttcca   3780
tctcagggga ctcccggatg ggtgtttccg ctctcaatag ccctcttgt tttaccagga    3840 aagatccagt taaatcaccc actgaggtga cagctcatta gcggggagag agatggagca   3900
tcgagtgaca ctgggccatc caggcggctc tgctcccacc agacaggagc taggcctcac   3960 tggcagggg gctgcccaca gccttttcag gggctcgctt ggcgggtgac ggggccgcag    4020
ccaggccttc tctccctgcc ccttggtgac cccgtggctt cctgtctgct ggcctctcct   4080
gctacttatc acttcaccac gaactctctg cctgagactg gggaagtaag cgggtatctt   4140
ctcagtgagc ataggttggg gactgtgatc ttgagaagcc atgggccagc aatacctgct   4200
tttctgaagc ccccaaggag ggctctgaca ttctttttaa aaacaccaca aagcaaaatt   4260
cccaggacat gtgtagtttt gtttgttcag tatcccacaa cttaaggctg ggagatggaa   4320
ctcttggtta aggtcgattt ttctgtctgg cttctccgca ccttccactt gctctctgga   4380
tcaggcagat ataaactttc tagcgcattt tgagagaggg cttttcttggg tgagggagca   4440 tggcaaagtc ggtttctctc tggactgttt acacttcaag gcggtggatt tagaggaatc   4500
ctggctttca ttttcaatgc cagtctgaga catgttccca agccggggct cttgttcaca   4560
ccacttactc tggccaccaa caacaaccca ggccagacag agcatctctt tttttttttt   4620
ttgagacaga gtctctgtcg cccaggctgg agcccagtgg cgagatcttg gctcactaca   4680
acctccacct cccgggttca ggcaattctc gtgcctaagc ctcccgagta gctgcgacta   4740
caggcgccgg ccagcatgcc tgtctaattt ttgtatttta gtagagacag ggtttcacca   4800
tgttgcccag gctggtctcg aactcctgag ctcaggcagt ctaccacct cagcctccca    4860 aagtgctggg attacaggcg tgagccaccg cgcccagcca aacatctgt ttttacaccc    4920 agagagcgcc cctcgttagg acagaaccac ggtgccagag ccaggaagc cgccctcctg    4980 gcgcccagca tctgagcttc tacacgtgat gggcgggctc aggagaggac agggagtcgt   5040
ggtggaagtt ccacagctgg ccgcgtgggg gggcccttgc accgcactgc cgcctcctga   5100
```

```
ctgcccctat ccccgcagcc cctgtgccgg atttcatttc cctcctctct cccagggtac    5160
ctggccccag cactctccca tctgttcttc aggaaccgac tcctctccag ttgcaacacc    5220
agggagaaag gggcctccac atgcccaagt acccctgcag gatgaagggc aggccggccc    5280
ttgatgtgcc atttctgaat aatagtcact gccgccgagt ctaggatgtc ctgttctaac    5340
tcagccctgc ctcggatgca ccaccgatct gtgcagagtg ggtgtgggag tgtgggtgag    5400
ggtcgaaatg ccaaaggtct actttccaga atcaagtgcc ttctgcaaat catgttggaa    5460
aagtccaaac ctggagatgt ccctgtgcct ccgcccctac ccaccccttt tccttcagct    5520
gtgttaggaa ggagaagttt tcagaaccct ctaggctggt ggctttcaaa cttcagacca    5580
tgatctgcag caagaaacgt gccttccatc ataaatcagt ccatttgttt acaactgtgt    5640
tccaagcagg tttcataaag aaattcttaa ccttagaacc tcggatatcc tctatgtttt    5700
agttttcatt tttttaaaat gcttcttaaa attcactaaa ttgggctagg tgtggctcat    5760
gcctgtaatc ccagcactat gggaggctga ggtgagagga tcacttgagc ccagaaggtt    5820
gaaaccagcc tgggcaacat agtgagaccc catctctaca aaaagtttta aaaccaggta    5880
tggtggtgcc ctcctgtggt cccagctact cgggagtctg aggtgggagg atcacctgag    5940
cccaggagac tgaggctgca gtaaggtgtg attgcactat tgctctctag cctggaaaac    6000
agagtgagac cctatctcaa aaaaaaaaaa aaaaaaaag gaaagagtga tgacaacagc    6060
ccagggagca gccccgctca gaacccaagt cccaagttcc agcactgtgt tcccaggcag    6120
gctgtttgcc tcttcctggt ctggaagccc ttgggtccta tggtggcggc agctcccaca    6180
gtccaggttc cctggtgggg accaatgatt ccatccgcat ggaagcccac gtgtgcactt    6240
aggggcccat aaatggcaga agggcccctc ctttgggaga ccttgtcagt cagcatctct    6300
agggcaaccg tgattgccat tgtagaggg gaaggaatca agggacttta agctagatca    6360
aaatctgggg acaaattctc ctgctaactg caagttaaaa taggcccttc ttactgaatt    6420
tccctgtttg tttctctgca gacaatgctt tagccctact cttgggcccc caagttagca    6480
gagtaatcaa agcttcctac cgtttggcct actattccag actagtccct cgaggggttc    6540
ccttccaaaa tatgcagggc tcaggctccc aattccgggc ctgtctgctt tgcttgtgtt    6600
tctcctgtcc ctgttctccc ggagggccca ggtggaactc acgacaggga gggagacgct    6660
tcccaaaaac ctgcagggct atttcccaga atttggtttt caagtacaaa acttttgtc    6720 ctgtaagata tatgcagcct cacagaagca gcctctgcct ccactttacc agctacgttt    6780
ttatcttaag cacatggggc tcccttagaa cttactccac tgatttaaaa aaaaaaaact    6840
gcctggcagc atctcagtgt cagagtgagc acggcacagg aaaggcccgt ggtgacgagg    6900
gtgaggtggc cacagtgacc ggacgacaaa tgagactctg caaatgagac tccagagggt    6960
gaagatctgc ggtctccaga catcataggc catgtgaccc actagggcc gcttacccct    7020 ggccgtccgc tggctgaact gaacgcattc cctctctccg caactctccc gtgaggctgc    7080
acccgtgtgg gtagcactgg aagcggcact gtttgcattg tacataggaa ggaaggaagt    7140
tcttccagcc tcaccagcac ctggcagcga gtcagagcct gtgagggcat ccgaagcagt    7200
gatgcagtgt caacctccca gctggtgcca ctctgccctc gggggctcca agcattgtaa    7260
ctcagtcatg ggagctgcct ctttggaagt gcagatttat tcctgtaata atcctgcctg    7320
cttttacctc tcgtccactg accagcaagt gtgagtcccg gtgtcagtcg gcacagtcca    7380
gtgtccatct gcatttgctc atgcagaggg ggtgagttgg cactccctg ttgttggttt    7440 tccttttgca gcacactggg cagtctccct ataaaacaaa aaccccacct tctgtgcctt    7500
```

-continued

```
ctgctttaga gcagagctcc ccctcccatt tcctcagtct tccctgcaaa atctgtccac    7560
cggggaaggc agcaggaacc ctgggcagcg ggtgttctgg gaaggctagt gacagcagat    7620
gtcatccagg aacagccaca cacggttctc caggccgccg tcagcagctc aaggtggggt    7680
atgagtgaga agctgaggat ctcgcagctt gttgctgagc aaggtgcaac cgggctcatg    7740
ctgtcatcag cacaagacgg gatggcaagg gctttcagac gcatttccaa gagtccagca    7800
agccaggggg aagatgatcc ctttgccgaa gtgtaccctc tagccaactt tttggagcgc    7860
ttctgtttgc aaagcgctgg ggatgtgcct gtctctgtgt gacccacgaa cgggaaggga    7920
gagcactgga gtaatgacac ttctgctgct gctttgattc tcaaggctga tcttaaaaac    7980
cctcgccttg ctgacaggtg ctttaaaggc agtctgcatc ttttcttccc ttggtgtggg    8040
agaggtaaac actttgattt gctgaaagct gtatggagta tatttgaaca gctagtagtt    8100
agctttgaaa gtggaagtgt gaacagacac tacttgtgtc gctttgggtc cttcactttA    8160
cccccacaga agtctagagg cgtctgttat aaagcgttac ggggcgcctg catgcaggag    8220
gaaggacctg tattagctgg aaatcatcag gaacccagct tgcctccatc tctctgagat    8280
gtgctgggta cagcctgccc ctcctagttc tgtccaccgg gaagagccgg ctggcggcag    8340
atccccaggg gcagagcccc tgctggatcc tgggagctca tctttacctg tgccggagtg    8400
ggaactgtga ttccagccgg gcaggtcaga gtggagcagt gctaagaggc tgttgcagga    8460
gaactagacg ggcggggcct gctgcatctg gatcatgttt ctgtgctctg ccccgcgcta    8520
gggactcagg gtctgggctt ctgccaggtg aggagcagag agactgttcc cttgggtgga    8580
gaggtgtggg catgagagcc acccattgcc aagcagcaag aatgttcgtg cttttttcca    8640
gagagggaa ccccactggt ttttgtggaa acaatggaaa cttacagatg cctgcctggg    8700
atgatgaggc acattcagaa caaatgcttt ttttttttg agacagagtc tcgctctgac    8760
gcccaggctg gagtgcagtg gcgcgatctc ggctcactgc aaactttgcc tcccaggttc    8820
aagtgattct cctacctcag cctcccgagt agctgggatt acaccaccat gcccagcaaa    8880
ttttgtgtt tttagtagag acggagtttc accatgttgg ccaggctggt ctcgaactcc    8940
tgacctcagg tgatccatcc gccttggcct cccaaagtgc tgggattaca ggcgggagcc    9000
accatgcctg gccagaacaa atgccttttt aaaccttttA agaacatttt taaaatgtct    9060
ttttctatgt caaatgtaac gtttattttt ttaaacaata aaattgattt gccaaaa      9117
```

<210> SEQ ID NO 10
<211> LENGTH: 791
<212> TYPE: PRT
<213> ORGANISM: Homo sapiens

<400> SEQUENCE: 10

```
Met Trp Asn Met Leu Ile Val Ala Met Cys Leu Ala Leu Leu Gly Cys
1               5                   10                  15

Leu Gln Ala Gln Glu Leu Gln Gly His Val Ser Ile Ile Leu Leu Gly
            20                  25                  30

Ala Thr Gly Asp Leu Ala Lys Lys Tyr Leu Trp Gln Gly Leu Phe Gln
        35                  40                  45

Leu Tyr Leu Asp Glu Ala Gly Arg Gly His Ser Phe Ser Phe His Gly
    50                  55                  60

Ala Ala Leu Thr Ala Pro Lys Gln Gly Gln Glu Leu Met Ala Lys Ala
65                  70                  75                  80

Leu Glu Ser Leu Ser Cys Pro Lys Asp Met Ala Pro Ser His Cys Ala
                85                  90                  95
```

```
Glu His Lys Asp Gln Phe Leu Gln Leu Ser Gln Tyr Arg Gln Leu Lys
            100                 105                 110

Thr Ala Glu Asp Tyr Gln Ala Leu Asn Lys Asp Ile Glu Ala Gln Leu
        115                 120                 125

Gln His Ala Gly Leu Arg Glu Ala Gly Arg Ile Phe Tyr Phe Ser Val
    130                 135                 140

Pro Pro Phe Ala Tyr Glu Asp Ile Ala Arg Asn Ile Asn Ser Ser Cys
145                 150                 155                 160

Arg Pro Gly Pro Gly Ala Trp Leu Arg Val Val Leu Glu Lys Pro Phe
                165                 170                 175

Gly His Asp His Phe Ser Ala Gln Gln Leu Ala Thr Glu Leu Gly Thr
            180                 185                 190

Phe Phe Gln Glu Glu Glu Met Tyr Arg Val Asp His Tyr Leu Gly Lys
        195                 200                 205

Gln Ala Val Ala Gln Ile Leu Pro Phe Arg Asp Gln Asn Arg Lys Ala
    210                 215                 220

Leu Asp Gly Leu Trp Asn Arg His Val Glu Arg Val Glu Ile Ile
225                 230                 235                 240

Met Lys Glu Thr Val Asp Ala Glu Gly Arg Thr Ser Phe Tyr Glu Glu
                245                 250                 255

Tyr Gly Val Ile Arg Asp Val Leu Gln Asn His Leu Thr Glu Val Leu
            260                 265                 270

Thr Leu Val Ala Met Glu Leu Pro His Asn Val Ser Ser Ala Glu Ala
        275                 280                 285

Val Leu Arg His Lys Leu Gln Val Phe Gln Ala Leu Arg Gly Leu Gln
    290                 295                 300

Arg Gly Ser Ala Val Val Gly Gln Tyr Gln Ser Tyr Ser Glu Gln Val
305                 310                 315                 320

Arg Arg Glu Leu Gln Lys Pro Asp Ser Phe His Ser Leu Thr Pro Thr
                325                 330                 335

Phe Ala Ala Val Leu Val His Ile Asp Asn Leu Arg Trp Glu Gly Val
            340                 345                 350

Pro Phe Ile Leu Met Ser Gly Lys Ala Leu Asp Glu Arg Val Gly Tyr
        355                 360                 365

Ala Arg Ile Leu Phe Lys Asn Gln Ala Cys Cys Val Gln Ser Glu Lys
    370                 375                 380

His Trp Ala Ala Ala Gln Ser Gln Cys Leu Pro Arg Gln Leu Val Phe
385                 390                 395                 400

His Ile Gly His Gly Asp Leu Gly Ser Pro Ala Val Leu Val Ser Arg
                405                 410                 415

Asn Leu Phe Arg Pro Ser Leu Pro Ser Ser Trp Lys Glu Met Glu Gly
            420                 425                 430

Pro Pro Gly Leu Arg Leu Phe Gly Ser Pro Leu Ser Asp Tyr Tyr Ala
        435                 440                 445

Tyr Ser Pro Val Arg Glu Arg Asp Ala His Ser Val Leu Leu Ser His
    450                 455                 460

Ile Phe His Gly Arg Lys Asn Phe Phe Ile Thr Thr Glu Asn Leu Leu
465                 470                 475                 480

Ala Ser Trp Asn Phe Trp Thr Pro Leu Leu Glu Ser Leu Ala His Lys
                485                 490                 495

Ala Pro Arg Leu Tyr Pro Gly Gly Ala Glu Asn Gly Arg Leu Leu Asp
            500                 505                 510
```

Phe Glu Phe Ser Ser Gly Arg Leu Phe Phe Ser Gln Gln Pro Glu
            515                 520                 525

Gln Leu Val Pro Gly Pro Gly Pro Ala Pro Met Pro Ser Asp Phe Gln
        530                 535                 540

Val Leu Arg Ala Lys Tyr Arg Glu Ser Pro Leu Val Ser Ala Trp Ser
545                 550                 555                 560

Glu Glu Leu Ile Ser Lys Leu Ala Asn Asp Ile Glu Ala Thr Ala Val
                565                 570                 575

Arg Ala Val Arg Arg Phe Gly Gln Phe His Leu Ala Leu Ser Gly Gly
            580                 585                 590

Ser Ser Pro Val Ala Leu Phe Gln Gln Leu Ala Thr Ala His Tyr Gly
        595                 600                 605

Phe Pro Trp Ala His Thr His Leu Trp Leu Val Asp Glu Arg Cys Val
    610                 615                 620

Pro Leu Ser Asp Pro Glu Ser Asn Phe Gln Gly Leu Gln Ala His Leu
625                 630                 635                 640

Leu Gln His Val Arg Ile Pro Tyr Tyr Asn Ile His Pro Met Pro Val
                645                 650                 655

His Leu Gln Gln Arg Leu Cys Ala Glu Glu Asp Gln Gly Ala Gln Ile
            660                 665                 670

Tyr Ala Arg Glu Ile Ser Ala Leu Val Ala Asn Ser Ser Phe Asp Leu
        675                 680                 685

Val Leu Leu Gly Met Gly Ala Asp Gly His Thr Ala Ser Leu Phe Pro
    690                 695                 700

Gln Ser Pro Thr Gly Leu Asp Gly Glu Gln Leu Val Val Leu Thr Thr
705                 710                 715                 720

Ser Pro Ser Gln Pro His Arg Arg Met Ser Leu Ser Leu Pro Leu Ile
                725                 730                 735

Asn Arg Ala Lys Lys Val Ala Val Leu Val Met Gly Arg Met Lys Arg
            740                 745                 750

Glu Ile Thr Thr Leu Val Ser Arg Val Gly His Glu Pro Lys Lys Trp
        755                 760                 765

Pro Ile Ser Gly Val Leu Pro His Ser Gly Gln Leu Val Trp Tyr Met
    770                 775                 780

Asp Tyr Asp Ala Phe Leu Gly
785                 790

<210> SEQ ID NO 11
<211> LENGTH: 2072
<212> TYPE: DNA
<213> ORGANISM: Homo sapiens

<400> SEQUENCE: 11
gaaacgaaag tgaaatcagc tgatagtgac atcagtcaga acaaatgtac caaagttcag        60
agagctgttt actaggcacg actgcgaagg caagggggca ccagctcagg actgcatctg       120
cctgccattt cccttccact cctcctttct ggagtctgac attagaaagc cagcgagaag       180
gaagattcaa acaaccaacc ctgatttcct gcttctcctt ttcatgagtg ttcctgtggt       240
ctctgcacct cctttctgtc cccggcagag gggcagtaga gatggccggc ccaaggcctc       300
ggtggcgcga ccagctgctg ttcatgagca tcatagtcct cgtgattgtg gtcatctgcc       360
tgatgtttta cgctcttctc tgggaggctg gcaacctcac tgacctgccc aacctgagaa       420
tcggcttcta taacttctgc ctgtggaatg aggacaccag cacctacagt gtcaccagt       480 tccctgagct ggaagccctg ggggtgcctc gggttggcct gggcctggcc aggcttggcg       540

-continued

```
tgtacgggtc cctggtcctc accctctttg ccccccagcc tctcctccta gcccagtgca      600
acagtgatga gagagcgtgg cggctggcag tgggcttcct ggctgtgtcc tctgtgctgc      660
tggcaggcgg cctgggcctc ttcctctcct atgtgtggaa gtgggtcagg ctctccctcc      720
cggggcctgg gtttctagct ctgggcagcg cccaggcctt actcatcctc ttgcttatag      780
ccatggctgt gttccctctg agggctgaga gggctgagag caagcttgag agctgctaaa      840
ggcttacgtg attgcaaggg ttcagttcca accatggtca gaggtggcac atctgctcag      900
ccatctcatt ttacagctaa cgctgatctc cagctccagc gatggaaccc actacagagg      960
aggtggggcc cctgtgtcaa agaggccgag gggcagcaag ggcagccagg gcacctgtga     1020
cttcttagta caagattgtc tgtccttcag gacttccaag gctcccaaag actccctaaa     1080
ccatgcagct cattgtcaca ccaattcctg ctttaattaa tggatctgag caaatcttcc     1140
tctagcttca ggagggtggg gagggagtga ttgctgtcat ggggccagac ttccaggctg     1200
atttgccaaa tgccaaaatg aaacctagca agaacttac ggcaacaaac gaggacatta      1260
aaagagcgag cacctcagtg tctctgggga catggttaag gagcttccac tcagcccacc     1320
atagtgagtg ggccgccata agccatcact ggaactccaa ccccagaggt ccaggagtga     1380
tctctgagtg actcaacaaa gacaggacac atggggtaca agacaaggc ttgactgctt      1440 caaagcttcc ctggacctga agccagacag ggcagaggcg tccgctgaca aatcactccc     1500
atgatgagac cctggaggac tccaaatcct cgctgtgaac aggactggac ggctgcacac     1560
aaacaaacgc tgccaccctc cacttcccaa cccagaactt ggaaagacat tagcacaact     1620
tacgcattgg ggaattgtgt gtattttcta gcacttgtgt attggaaaac ctgtatggca     1680
gtgatttatt catatattcc tgtccaaagc cacactgaaa acagaggcag agacatgtac     1740
tctggtgtga tctcttgtcc tcagtgtctc ttctgggctc ctgtccctct tgctttatag     1800
ctagctgccc ggggaccaag gtacaggtga aagcaaggta gcagcttgcg ggaggaggcc     1860
tgtctggctt accagtctat acactgtggc ctcaacctcc cagacagggc agagaactgt     1920
gggcagctcg tttgctttct aggctggctg gagaggtggg agctcattga tagactcatg     1980
atggaaacta tttttgaaac aggcttcctc cttcaggaga gatcatgcgg actaaactgt     2040
agcaattcca gtgcaaaaaa aaaaaaaaaa aa                                    2072
```

<210> SEQ ID NO 12
<211> LENGTH: 185
<212> TYPE: PRT
<213> ORGANISM: Homo sapiens

<400> SEQUENCE: 12

Met Ala Gly Pro Arg Pro Arg Trp Arg Asp Gln Leu Leu Phe Met Ser
1               5                   10                  15

Ile Ile Val Leu Val Ile Val Ile Cys Leu Met Phe Tyr Ala Leu
            20                  25                  30

Leu Trp Glu Ala Gly Asn Leu Thr Asp Leu Pro Asn Leu Arg Ile Gly
        35                  40                  45

Phe Tyr Asn Phe Cys Leu Trp Asn Glu Asp Thr Ser Thr Leu Gln Cys
    50                  55                  60

His Gln Phe Pro Glu Leu Glu Ala Leu Gly Val Pro Arg Val Gly Leu
65                  70                  75                  80

Gly Leu Ala Arg Leu Gly Val Tyr Gly Ser Leu Val Leu Thr Leu Phe
                85                  90                  95

```
Ala Pro Gln Pro Leu Leu Leu Ala Gln Cys Asn Ser Asp Glu Arg Ala
            100                 105                 110

Trp Arg Leu Ala Val Gly Phe Leu Ala Val Ser Ser Val Leu Leu Ala
        115                 120                 125

Gly Gly Leu Gly Leu Phe Leu Ser Tyr Val Trp Lys Trp Val Arg Leu
    130                 135                 140

Ser Leu Pro Gly Pro Gly Phe Leu Ala Leu Gly Ser Ala Gln Ala Leu
145                 150                 155                 160

Leu Ile Leu Leu Leu Ile Ala Met Ala Val Phe Pro Leu Arg Ala Glu
                165                 170                 175

Arg Ala Glu Ser Lys Leu Glu Ser Cys
            180                 185

<210> SEQ ID NO 13
<211> LENGTH: 2454
<212> TYPE: DNA
<213> ORGANISM: Homo sapiens

<400> SEQUENCE: 13
ctttagcaat ggggaaatac cgtagactgt tccatcagga caatgctggg cctgcagtcc     60
ccaggggggca cccacttact tagccaaacc ccagacgttt catttaaaag cagaagtgaa    120
aggaagacca ggttcctgaa agggttattc tgacttaatc tggctataaa aatgctattg    180
gctgttattt ggcatggcca aagtgcaccc agaatgtctt ctctctccat tcagtgcacg    240
cgttactttg gctaaaagga ggtgagcggc actctgccct ccagagcaa gcatggagca    300
acaggatcag agcatgaagg aagggaggct gacgcttgtg cttgccctgg caaccctgat    360
agctgccttt gggtcatcct tccagtatgg gtacaacgtg gctgctgtca actccccagc    420
actgctcatg caacaatttt acaatgagac ttactatggt aggaccggtg aattcatgga    480
agacttcccc ttgacgttgc tgtggtctgt aaccgtgtcc atgtttccat tggagggtt    540
tatcggatcc ctcctggtcg gccccttggt gaataaattt ggcagaaaag gggcttgct   600
gttcaacaac atattttcta tcgtgcctgc gatcttaatg ggatgcagca gagtcgccac    660
atcatttgag cttatcatta tttccagact tttggtggga atatgtgcag gtgtatcttc    720
caacgtggtc cccatgtact aggggagct ggcccctaaa aacctgcggg gggctctcgg    780
ggtggtgccc cagctcttca tcactgttgg catccttgtg gcccagatct ttggtcttcg    840
gaatctcctt gcaaacgtag atggctggcc gatcctgctg gggctgaccg gggtccccgc    900
ggcgctgcag ctccttctgc tgcccttctt ccccgagagc cccaggtacc tgctgattca    960
gaagaaagac gaagcggccg ccaagaaagc cctacagacg ctgcgcggct gggactctgt   1020
ggacagggag gtggccgaga tccggcagga ggatgaggca gagaaggccg cgggcttcat   1080
ctccgtgctg aagctgttcc ggatgcgctc gctgcgctgg cagctgctgt ccatcatcgt   1140
cctcatgggc ggccagcagc tgtcgggcgt caacgctatc tactactacg cggaccagat   1200
ctacctgagc gccggcgtgc cggaggagca cgtgcagtac gtgacggccg gcaccggggc   1260
cgtgaacgtg gtcatgacct tctgcgccgt gttcgtggtg gagctcctgg gtcggaggct   1320
gctgctgctg ctgggcttct ccatctgcct catagcctgc tgcgtgctca ctgcagctct   1380
ggcactgcag gacacagtgt cctggatgcc atacatcagc atcgtctgtg tcatctccta   1440
cgtcatagga catgccctcg ggccagtcc catacccgcg ctgctcatca ctgagatctt   1500
cctgcagtcc tctcggccat ctgccttcat ggtgggggggc agtgtgcact ggctctccaa   1560
cttcaccgtg ggcttgatct tccccgttca tccaggaggg ctcggcccgt acagcttcat   1620
```

```
tgtcttcgcc gtgatctgcc tcctcaccac catctacatc ttcttgattg tcccggagac    1680
caaggccaag acgttcatag agatcaacca gattttcacc aagatgaata aggtgtctga    1740
agtgtacccg gaaaaggagg aactgaaaga gcttccacct gtcacttcgg aacagtgact    1800
ctggagagga agccagtgga gctggtctgc caggggcttc ccactttggc ttatttttct    1860
gacttctagc tgtctgtgaa tatccagaaa taaaacaact ctgatgtgga atgcagtcct    1920
catctccagc ctccccaccc cagtgggaac tgtgcaaagg gctgccttgc tgttcttgaa    1980
gctgggctgt ctctctccat gttggcctgt caccagaccc gagtcaatta acagctggt    2040
cctccacttt gctggttcag ccttcgtgtg gctcctggta acgtggctcc accttgatgg    2100
gtcaaccttt gtgtggctcc tggtaacata acaacaacag ttactatagt ggtgagatgg    2160
aaggaatcaa attttgccag agaaactaac ttggtggccc cgacaggtct tccggggcca    2220
tgggcatttg tttagagcca aattcatcct cttaccagat ccttttccag aaatacctgt    2280
ctaggaaggt gtgatgtcag aaacaatgac atccagaaag ctgaggaaca ggttcctgtg    2340
gagacactga gtcagaattc ttcatcctaa attattttgt tagtgaaaaa tggaattgct    2400
tctgtgtagt caataaaatg aacctgatca cttttcaaaa aaaaaaaaaa aaaa          2454
```

<210> SEQ ID NO 14
<211> LENGTH: 501
<212> TYPE: PRT
<213> ORGANISM: Homo sapiens

<400> SEQUENCE: 14

```
Met Glu Gln Gln Asp Gln Ser Met Lys Glu Gly Arg Leu Thr Leu Val
1               5                   10                  15

Leu Ala Leu Ala Thr Leu Ile Ala Ala Phe Gly Ser Ser Phe Gln Tyr
            20                  25                  30

Gly Tyr Asn Val Ala Ala Val Asn Ser Pro Ala Leu Leu Met Gln Gln
        35                  40                  45

Phe Tyr Asn Glu Thr Tyr Tyr Gly Arg Thr Gly Glu Phe Met Glu Asp
    50                  55                  60

Phe Pro Leu Thr Leu Leu Trp Ser Val Thr Val Ser Met Phe Pro Phe
65                  70                  75                  80

Gly Gly Phe Ile Gly Ser Leu Leu Val Gly Pro Leu Val Asn Lys Phe
                85                  90                  95

Gly Arg Lys Gly Ala Leu Leu Phe Asn Asn Ile Phe Ser Ile Val Pro
            100                 105                 110

Ala Ile Leu Met Gly Cys Ser Arg Val Ala Thr Ser Phe Glu Leu Ile
        115                 120                 125

Ile Ile Ser Arg Leu Leu Val Gly Ile Cys Ala Gly Val Ser Ser Asn
    130                 135                 140

Val Val Pro Met Tyr Leu Gly Glu Leu Ala Pro Lys Asn Leu Arg Gly
145                 150                 155                 160

Ala Leu Gly Val Val Pro Gln Leu Phe Ile Thr Val Gly Ile Leu Val
                165                 170                 175

Ala Gln Ile Phe Gly Leu Arg Asn Leu Leu Ala Asn Val Asp Gly Trp
            180                 185                 190

Pro Ile Leu Leu Gly Leu Thr Gly Val Pro Ala Ala Leu Gln Leu Leu
        195                 200                 205

Leu Leu Pro Phe Phe Pro Glu Ser Pro Arg Tyr Leu Leu Ile Gln Lys
    210                 215                 220
```

Lys Asp Glu Ala Ala Ala Lys Lys Ala Leu Gln Thr Leu Arg Gly Trp
225                 230                 235                 240

Asp Ser Val Asp Arg Glu Val Ala Glu Ile Arg Gln Glu Asp Glu Ala
            245                 250                 255

Glu Lys Ala Ala Gly Phe Ile Ser Val Leu Lys Leu Phe Arg Met Arg
        260                 265                 270

Ser Leu Arg Trp Gln Leu Leu Ser Ile Ile Val Leu Met Gly Gly Gln
    275                 280                 285

Gln Leu Ser Gly Val Asn Ala Ile Tyr Tyr Ala Asp Gln Ile Tyr
290                 295                 300

Leu Ser Ala Gly Val Pro Glu Glu His Val Gln Tyr Val Thr Ala Gly
305                 310                 315                 320

Thr Gly Ala Val Asn Val Val Met Thr Phe Cys Ala Val Phe Val Val
            325                 330                 335

Glu Leu Leu Gly Arg Arg Leu Leu Leu Leu Gly Phe Ser Ile Cys
        340                 345                 350

Leu Ile Ala Cys Cys Val Leu Thr Ala Ala Leu Ala Leu Gln Asp Thr
    355                 360                 365

Val Ser Trp Met Pro Tyr Ile Ser Ile Val Cys Val Ile Ser Tyr Val
370                 375                 380

Ile Gly His Ala Leu Gly Pro Ser Pro Ile Pro Ala Leu Leu Ile Thr
385                 390                 395                 400

Glu Ile Phe Leu Gln Ser Ser Arg Pro Ser Ala Phe Met Val Gly Gly
            405                 410                 415

Ser Val His Trp Leu Ser Asn Phe Thr Val Gly Leu Ile Phe Pro Phe
        420                 425                 430

Ile Gln Glu Gly Leu Gly Pro Tyr Ser Phe Ile Val Phe Ala Val Ile
    435                 440                 445

Cys Leu Leu Thr Thr Ile Tyr Ile Phe Leu Ile Val Pro Glu Thr Lys
450                 455                 460

Ala Lys Thr Phe Ile Glu Ile Asn Gln Ile Phe Thr Lys Met Asn Lys
465                 470                 475                 480

Val Ser Glu Val Tyr Pro Glu Lys Glu Glu Leu Lys Glu Leu Pro Pro
            485                 490                 495

Val Thr Ser Glu Gln
        500

<210> SEQ ID NO 15
<211> LENGTH: 1280
<212> TYPE: DNA
<213> ORGANISM: Homo sapiens

<400> SEQUENCE: 15
ctttagcaat ggggaaatac cgtagactgt tccatcagga caatgctggg cctgcagtcc    60 ccaggggggca cccacttact tagccaaacc ccagacgttt catttaaaag cagaagtgaa   120
aggaagacca ggttcctgaa agggttattc tgacttaatc tggctataaa aatgctattg   180
gctgttattt ggcatggcca agtgcaccc agaatgtctt ctctctccat tcagtgcacg    240
cgttactttg gctaaaagga ggtgagcggc actctgccct tccagagcaa gcatggagca   300
acaggatcag agcatgaagg aagggaggct gacgcttgtg cttgccctgg caaccctgat   360
agctgccttt gggtcatcct tccagtatgg gtacaacgtg ctgctgtca actccccagc   420 actgctcatg caacaatttt acaatgagac ttactatggt aggaccggtg aattcatgga   480
agacttcccc ttgacgttgc tgtggtctgt aaccgtgtcc atgtttccat tggagggtt    540

```
tatcggatcc ctcctggtcg gccccttggt gaataaattt ggcagaaaag gggccttgct    600
gttcaacaac atattttcta tcgtgcctgc gatcttaatg ggatgcagca gagtcgccac    660
atcatttgag cttatcatta tttccagact tttggtggga atatgtgcag gtgtatcttc    720
caacgtggtc cccatgtact tagggagct ggcccctaaa aacctgcggg gggctctcgg     780
ggtggtgccc cagctcttca tcactgttgg catccttgtg gcccagatct ttggtcttcg    840
gaatctcctt gcaaacgtag atggtgagtt caggacatct cgggagcacc cccacccctt    900
caccactacc cttggcccc ccttgtgtt ccaaagccac caccacagga caggactttc       960
tgcagactgg tctcttctaa caggctggat gtccttgggg ggcccatcct gtcccgagcc    1020
aacatagcag gccatggaca aaggcgcgat aagggactgg ccagcgttta ctatctagtc    1080
cctcttagga gatggatgag gtggctttga gtgatgggct tccctgcctg ctcagcagct    1140
gtccatatgg aggcccgtgg catagcaatg acagccacca gtgtgccagg ctctgtgctt    1200
ggggcggacc cagcatcagt tcataggacc ctcccagcaa cgctgctgcc tgggactcag    1260
tgattatccc attttgcaga                                                1280
```

<210> SEQ ID NO 16
<211> LENGTH: 244
<212> TYPE: PRT
<213> ORGANISM: Homo sapiens

<400> SEQUENCE: 16

```
Met Glu Gln Gln Asp Gln Ser Met Lys Glu Gly Arg Leu Thr Leu Val
1               5                   10                  15

Leu Ala Leu Ala Thr Leu Ile Ala Ala Phe Gly Ser Ser Phe Gln Tyr
            20                  25                  30

Gly Tyr Asn Val Ala Ala Val Asn Ser Pro Ala Leu Leu Met Gln Gln
        35                  40                  45

Phe Tyr Asn Glu Thr Tyr Tyr Gly Arg Thr Gly Glu Phe Met Glu Asp
    50                  55                  60

Phe Pro Leu Thr Leu Leu Trp Ser Val Thr Val Ser Met Phe Pro Phe
65                  70                  75                  80

Gly Gly Phe Ile Gly Ser Leu Leu Val Gly Pro Leu Val Asn Lys Phe
                85                  90                  95

Gly Arg Lys Gly Ala Leu Leu Phe Asn Asn Ile Phe Ser Ile Val Pro
            100                 105                 110

Ala Ile Leu Met Gly Cys Ser Arg Val Ala Thr Ser Phe Glu Leu Ile
        115                 120                 125

Ile Ile Ser Arg Leu Leu Val Gly Ile Cys Ala Gly Val Ser Ser Asn
    130                 135                 140

Val Val Pro Met Tyr Leu Gly Glu Leu Ala Pro Lys Asn Leu Arg Gly
145                 150                 155                 160

Ala Leu Gly Val Val Pro Gln Leu Phe Ile Thr Val Gly Ile Leu Val
                165                 170                 175

Ala Gln Ile Phe Gly Leu Arg Asn Leu Leu Ala Asn Val Asp Gly Glu
            180                 185                 190

Phe Arg Thr Ser Arg Glu His Pro His Pro Phe Thr Thr Thr Leu Gly
        195                 200                 205

Pro Leu Leu Val Phe Gln Ser His His His Arg Thr Gly Leu Ser Ala
    210                 215                 220
```

Asp Trp Ser Leu Leu Thr Gly Trp Met Ser Leu Gly Gly Pro Ser Cys
225                 230                 235                 240

Pro Glu Pro Thr

<210> SEQ ID NO 17
<211> LENGTH: 1509
<212> TYPE: DNA
<213> ORGANISM: Homo sapiens

<400> SEQUENCE: 17

| | | | | | |
|---|---|---|---|---|---|
| ccaccgcagc | ggacagcgcc | aagtgaagcc | tcgcttcccc | tccgcggcga | ccagggcccg | 60 |
| agccgagagt | agcagttgta | gctaccgcc | cagaaactag | acacaatgtg | cgacgaagac | 120 |
| gagaccaccg | ccctcgtgtg | cgacaatggc | tccggcctgg | tgaaagccgg | cttcgccggg | 180 |
| gatgacgccc | ctagggccgt | gttcccgtcc | atcgtgggcc | gccccgaca | ccagggcgtc | 240 |
| atggtcggta | tgggtcagaa | agattcctac | gtgggcgacg | aggctcagag | caagagaggt | 300 |
| atcctgaccc | tgaagtaccc | tatcgagcac | ggcatcatca | ccaactggga | tgacatggag | 360 |
| aagatctggc | accacacctt | ctacaacgag | cttcgcgtgg | ctcccgagga | gcaccccacc | 420 |
| ctgctcaccg | aggcccccct | caatcccaag | gccaaccgcg | agaagatgac | ccagatcatg | 480 |
| tttgagacct | tcaacgtgcc | cgccatgtac | gtggccatcc | aggccgtgct | gtccctctac | 540 |
| gcctccggca | ggaccaccgg | catcgtgctg | gactccggcg | acggcgtcac | ccacaacgtg | 600 |
| cccatttatg | agggctacgc | gctgccgcac | gccatcatgc | gcctggacct | ggcgggccgc | 660 |
| gatctcaccg | actacctgat | gaagatcctc | actgagcgtg | gctactcctt | cgtgaccaca | 720 |
| gctgagcgcg | agatcgtgcg | cgacatcaag | gagaagctgt | gctacgtggc | cctggacttc | 780 |
| gagaacgaga | tggcgacggc | cgcctcctcc | tcctccctgg | aaaagagcta | cgagctgcca | 840 |
| gacgggcagg | tcatcaccat | cggcaacgag | cgcttccgct | gcccggagac | gctcttccag | 900 |
| ccctccttca | tcggtatgga | gtcggcgggc | attcacgaga | ccacctacaa | cagcatcatg | 960 |
| aagtgtgaca | tcgacatcag | gaaggacctg | tatgccaaca | acgtcatgtc | gggggggcacc | 1020 |
| acgatgtacc | ctgggatcgc | tgaccgcatg | cagaaagaga | tcaccgcgct | ggcacccagc | 1080 |
| accatgaaga | tcaagatcat | cgccccgccg | gagcgcaaat | actcggtgtg | gatcggcggc | 1140 |
| tccatcctgg | cctcgctgtc | caccttccag | cagatgtgga | tcaccaagca | ggagtacgac | 1200 |
| gaggccggcc | cttccatcgt | ccaccgcaaa | tgcttctaga | cacactccac | ctccagcacg | 1260 |
| cgacttctca | ggacgacgaa | tcttctcaat | ggggggggcgg | ctgagctcca | gccacccgc | 1320 |
| agtcactttc | tttgtaacaa | cttccgttgc | tgccatcgta | aactgacaca | gtgtttataa | 1380 |
| cgtgtacata | cattaactta | ttacctcatt | ttgttatttt | tcgaaacaaa | gccctgtgga | 1440 |
| agaaaatgga | aaacttgaag | aagcattaaa | gtcattctgt | taagctgcgt | aaaaaaaaaa | 1500 |
| aaaaaaaaa | | | | | | 1509 |

<210> SEQ ID NO 18
<211> LENGTH: 377
<212> TYPE: PRT
<213> ORGANISM: Homo sapiens

<400> SEQUENCE: 18

Met Cys Asp Glu Asp Glu Thr Thr Ala Leu Val Cys Asp Asn Gly Ser
1               5                   10                  15

Gly Leu Val Lys Ala Gly Phe Ala Gly Asp Asp Ala Pro Arg Ala Val
                20                  25                  30

Phe Pro Ser Ile Val Gly Arg Pro Arg His Gln Gly Val Met Val Gly
            35                  40                  45

Met Gly Gln Lys Asp Ser Tyr Val Gly Asp Glu Ala Gln Ser Lys Arg
 50                  55                  60

Gly Ile Leu Thr Leu Lys Tyr Pro Ile Glu His Gly Ile Ile Thr Asn
 65                  70                  75                  80

Trp Asp Asp Met Glu Lys Ile Trp His His Thr Phe Tyr Asn Glu Leu
                 85                  90                  95

Arg Val Ala Pro Glu Glu His Pro Thr Leu Leu Thr Glu Ala Pro Leu
                100                 105                 110

Asn Pro Lys Ala Asn Arg Glu Lys Met Thr Gln Ile Met Phe Glu Thr
            115                 120                 125

Phe Asn Val Pro Ala Met Tyr Val Ala Ile Gln Ala Val Leu Ser Leu
130                 135                 140

Tyr Ala Ser Gly Arg Thr Thr Gly Ile Val Leu Asp Ser Gly Asp Gly
145                 150                 155                 160

Val Thr His Asn Val Pro Ile Tyr Glu Gly Tyr Ala Leu Pro His Ala
                165                 170                 175

Ile Met Arg Leu Asp Leu Ala Gly Arg Asp Leu Thr Asp Tyr Leu Met
            180                 185                 190

Lys Ile Leu Thr Glu Arg Gly Tyr Ser Phe Val Thr Thr Ala Glu Arg
        195                 200                 205

Glu Ile Val Arg Asp Ile Lys Glu Lys Leu Cys Tyr Val Ala Leu Asp
210                 215                 220

Phe Glu Asn Glu Met Ala Thr Ala Ala Ser Ser Ser Ser Leu Glu Lys
225                 230                 235                 240

Ser Tyr Glu Leu Pro Asp Gly Gln Val Ile Thr Ile Gly Asn Glu Arg
                245                 250                 255

Phe Arg Cys Pro Glu Thr Leu Phe Gln Pro Ser Phe Ile Gly Met Glu
            260                 265                 270

Ser Ala Gly Ile His Glu Thr Thr Tyr Asn Ser Ile Met Lys Cys Asp
        275                 280                 285

Ile Asp Ile Arg Lys Asp Leu Tyr Ala Asn Asn Val Met Ser Gly Gly
290                 295                 300

Thr Thr Met Tyr Pro Gly Ile Ala Asp Arg Met Gln Lys Glu Ile Thr
305                 310                 315                 320

Ala Leu Ala Pro Ser Thr Met Lys Ile Lys Ile Ile Ala Pro Pro Glu
                325                 330                 335

Arg Lys Tyr Ser Val Trp Ile Gly Gly Ser Ile Leu Ala Ser Leu Ser
            340                 345                 350

Thr Phe Gln Gln Met Trp Ile Thr Lys Gln Glu Tyr Asp Glu Ala Gly
        355                 360                 365

Pro Ser Ile Val His Arg Lys Cys Phe
370                 375

<210> SEQ ID NO 19
<211> LENGTH: 2678
<212> TYPE: DNA
<213> ORGANISM: Homo sapiens

<400> SEQUENCE: 19
agcgcggcag caagcgtggg aacgcgggcg gcgagacggc ggcaggacgg cggcaggatg        60
tgtgaccgga atggtggtcg gcggcttcga cagtggctga tcgagcagat tgacagtagc       120
atgtatccag gactgatttg ggagaatgag gagaagagca tgttccggat cccttggaaa       180

-continued

```
cacgctggca agcaagatta taatcaggaa gtggatgcct ccattttaa ggcctgggca      240 gtttttaaag ggaagtttaa agaaggggac aaagctgaac cagccacttg aagacgagg      300 ttacgctgtg ctttgaataa gagcccagat tttgaggaag tgacggaccg gtcccaactg     360
gacatttccg agccatacaa agtttaccga attgttcctg aggaagagca aaaatgcaaa     420
ctaggcgtgg caactgctgg ctgcgtgaat gaagttacag agatggagtg cggtcgctct     480
gaaatcgacg agctgatcaa ggagccttct gtggacgatt acatggggat gatcaaaagg     540
agcccttccc cgccggaggc ctgtcggagt cagctccttc cagactggtg ggcgcagcag     600
cccagcacag gcgtgccgct ggtgacgggg tacaccacct acgacgcgca ccattcagca     660
ttctcccaga tggtgatcag cttctactat gggggcaagc tggtgggcca ggccaccacc     720
acctgccccg agggctgccg cctgtccctg agccagcctg gctgccccgg caccaagctg     780
tatgggcccg agggcctgga gctggtgcgc ttcccgccgg ccgacgccat ccccagcgag     840
cgacagaggc aggtgacgcg gaagctgttc gggcacctgg agcgcggggt gctgctgcac     900
agcagccggc agggcgtgtt cgtcaagcgg ctgtgccagg ccgcgtgtt ctgcagcggc      960 aacgccgtgg tgtgcaaagg caggcccaac aagctggagc gtgatgaggt ggtccaggtc     1020
ttcgacacca gccagttctt ccgagagctg cagcagttct ataacagcca gggccggctt     1080
cctgacggca gggtggtgct gtgctttggg gaagagtttc ggatatggc ccccttgcgc      1140 tccaaactca ttctcgtgca gattgagcag ctgtatgtcc ggcaactggc agaagaggct     1200
gggaagagct gtggagccgg ctctgtgatg caggcccccg aggagccgcc gccagaccag     1260
gtcttccgga tgtttccaga tatttgtgcc tcacaccaga gatcatttt cagagaaaac      1320 caacagatca ccgtctaagt gcgtcgcttg ggcgccccac cccgtctgcg tcctgcatcc     1380
atctccctgt tacagtggcc cgcatcatga ttaaagaatg tggatccctc tgtctggggt     1440
gggatgcctt actttgcact taatttaata agggcattct cggaggagta gacgtttaat     1500
acgaagtggc ggcatagccc tgccgagatg tcggtgatgg cctggatgct gtaaccacaa     1560
cctgtggcta aaaattttat tttctatcct ttacccgtca ttatcattag ttgctatgat     1620
tctttctgca ttttcggtta actatcattt ccaaagactt gtcattcagt aatattagca     1680
gatagctgct tcgataaagg aatttggagt ttaaaaatca acttgtgaaa acaaggttgt     1740
ttttgtcttt atcgtttgtt agagttatag atttatgatt tcataggctt gattctatgt      1800
gaaatatctt tttactttta tgcattttaa taagatttaa aaatatttag attaaagccc     1860
cctttaatga gtacaagaaa aactcttggc ttgttagaag aaagtatatt ctttctagaa     1920
tttggtgcag gaatatgtgt tcatatccag gcaaacgggt gtgttttat cttcagacaa      1980 tgaaaccttc tcctctgggg ctttgttgcc aggaagatta gaactaaatt tattttttc      2040 atttctgtca tgaaatcatt ccagatacct cttttcttct ttccaaatgg ttttcacatg     2100
tgtttgaaat atttgtactt cgaattgtcg gattttccat gtcctccttt ctcctttgtg     2160
cccagcctga gtcagcacca atcccgcatt cagaacctcc cagtgaaagg gcagccttca     2220
ttttgagaag gtggaaggtg ttagggtttg ggagacagct catccaatct cccaagtctc     2280
atggtggatt tgtgactgtg agagtttccg gtttaaaatc tgaaaagcca gatatgcctg     2340
tttccttttc ccagcaccat gcctgtggag gggacagtca gacccagagg tcctttacgt     2400
gtggatggag ttcacaggcg aatagaggag aggaccaggg gacgtggctt gtcccttttg     2460
tccaacaaag cattatattt ttaagaatgg cagacctgtt tgctgaagtg ttcataagat     2520
aacaataggc ttgaatctcc aattcaaatg aatgtcaaag cacatatctt taatatgctg     2580
```

```
aatgaatatt tatttttgta tccattaaaa cagtatattg atctctttta ttctttatta    2640
aaataaaatg ctctttttta aaaaaaaaaa aaaaaaaa                            2678
```

<210> SEQ ID NO 20
<211> LENGTH: 426
<212> TYPE: PRT
<213> ORGANISM: Homo sapiens

<400> SEQUENCE: 20

```
Met Cys Asp Arg Asn Gly Gly Arg Arg Leu Arg Gln Trp Leu Ile Glu
1               5                   10                  15

Gln Ile Asp Ser Ser Met Tyr Pro Gly Leu Ile Trp Glu Asn Glu Glu
            20                  25                  30

Lys Ser Met Phe Arg Ile Pro Trp Lys His Ala Gly Lys Gln Asp Tyr
        35                  40                  45

Asn Gln Glu Val Asp Ala Ser Ile Phe Lys Ala Trp Ala Val Phe Lys
    50                  55                  60

Gly Lys Phe Lys Glu Gly Asp Lys Ala Glu Pro Ala Thr Trp Lys Thr
65                  70                  75                  80

Arg Leu Arg Cys Ala Leu Asn Lys Ser Pro Asp Phe Glu Glu Val Thr
                85                  90                  95

Asp Arg Ser Gln Leu Asp Ile Ser Glu Pro Tyr Lys Val Tyr Arg Ile
            100                 105                 110

Val Pro Glu Glu Gln Lys Cys Lys Leu Gly Val Ala Thr Ala Gly
        115                 120                 125

Cys Val Asn Glu Val Thr Glu Met Glu Cys Gly Arg Ser Glu Ile Asp
130                 135                 140

Glu Leu Ile Lys Glu Pro Ser Val Asp Asp Tyr Met Gly Met Ile Lys
145                 150                 155                 160

Arg Ser Pro Ser Pro Glu Ala Cys Arg Ser Gln Leu Leu Pro Asp
                165                 170                 175

Trp Trp Ala Gln Gln Pro Ser Thr Gly Val Pro Leu Val Thr Gly Tyr
            180                 185                 190

Thr Thr Tyr Asp Ala His His Ser Ala Phe Ser Gln Met Val Ile Ser
        195                 200                 205

Phe Tyr Tyr Gly Gly Lys Leu Val Gly Gln Ala Thr Thr Thr Cys Pro
    210                 215                 220

Glu Gly Cys Arg Leu Ser Leu Ser Gln Pro Gly Leu Pro Gly Thr Lys
225                 230                 235                 240

Leu Tyr Gly Pro Glu Gly Leu Glu Leu Val Arg Phe Pro Pro Ala Asp
                245                 250                 255

Ala Ile Pro Ser Glu Arg Gln Arg Gln Val Thr Arg Lys Leu Phe Gly
            260                 265                 270

His Leu Glu Arg Gly Val Leu Leu His Ser Ser Arg Gln Gly Val Phe
        275                 280                 285

Val Lys Arg Leu Cys Gln Gly Arg Val Phe Cys Ser Gly Asn Ala Val
    290                 295                 300

Val Cys Lys Gly Arg Pro Asn Lys Leu Glu Arg Asp Glu Val Val Gln
305                 310                 315                 320

Val Phe Asp Thr Ser Gln Phe Arg Glu Leu Gln Gln Phe Tyr Asn
                325                 330                 335

Ser Gln Gly Arg Leu Pro Asp Gly Arg Val Val Leu Cys Phe Gly Glu
            340                 345                 350
```

```
Glu Phe Pro Asp Met Ala Pro Leu Arg Ser Lys Leu Ile Leu Val Gln
            355                 360                 365
Ile Glu Gln Leu Tyr Val Arg Gln Leu Ala Glu Ala Gly Lys Ser
        370                 375                 380
Cys Gly Ala Gly Ser Val Met Gln Ala Pro Glu Glu Pro Pro Asp
385                 390                 395                 400
Gln Val Phe Arg Met Phe Pro Asp Ile Cys Ala Ser His Gln Arg Ser
                    405                 410                 415
Phe Phe Arg Glu Asn Gln Gln Ile Thr Val
            420                 425

<210> SEQ ID NO 21
<211> LENGTH: 4576
<212> TYPE: DNA
<213> ORGANISM: Homo sapiens

<400> SEQUENCE: 21
```

| | | | | | |
|---|---|---|---|---|---|
| tggcagccag | tgtcggggtg | gcggctggga | atggggccg | ctccggactt | ccgctgccaa | 60 |
| ctacaagggg | gcgggtccga | gggggttag | ccgaagttgt | aggcggggcg | cgaggttcta | 120 |
| gtacccgagc | tcatactagg | gacgggaagt | cgcgaccaga | gccattggag | ggcgcgggga | 180 |
| ctgcaaccct | aatcagagcc | caaatggcgc | agtgggaaat | gctgcagaat | cttgacagcc | 240 |
| cctttcagga | tcagctgcac | cagctttact | cgcacagcct | cctgcctgtg | acattcgac | 300 |
| agtacttggc | tgtctggatt | gaagaccaga | actggcagga | agctgcactt | gggagtgatg | 360 |
| attccaaggc | taccatgcta | ttcttccact | tcttggatca | gctgaactat | gagtgtggcc | 420 |
| gttgcagcca | ggacccagag | tccttgttgc | tgcagcacaa | tttgcggaaa | ttctgccggg | 480 |
| acattcagcc | cttttcccag | gatcctaccc | agttggctga | tgatctttt | aacctccttc | 540 |
| tggaagaaaa | aagaattttg | atccaggctc | agagggccca | attggaacaa | ggagagccag | 600 |
| ttctcgaaac | acctgtggag | agccagcaac | atgagattga | atcccggatc | ctggatttaa | 660 |
| gggctatgat | ggagaagctg | gtaaaatcca | tcagccaact | gaaagaccag | caggatgtct | 720 |
| tctgcttccg | atataagatc | caggccaaag | ggaagacacc | ctctctggac | ccccatcaga | 780 |
| ccaaagagca | gaagattctg | caggaaactc | tcaatgaact | ggacaaaagg | agaaaggagg | 840 |
| tgctggatgc | ctccaaagca | ctgctaggcc | gattaactac | cctaatcgag | ctactgctgc | 900 |
| caaagttgga | ggagtggaag | gcccagcagc | aaaaagcctg | catcagagct | cccattgacc | 960 |
| acgggttgga | acagctggag | acatggttca | cagctggagc | aaagctgttg | tttcacctga | 1020 |
| ggcagctgct | gaaggagctg | aagggactga | gttgcctggt | tagctatcag | gatgaccctc | 1080 |
| tgaccaaagg | ggtggaccta | cgcaacgccc | aggtcacaga | gttgctacag | cgtctgctcc | 1140 |
| acagagcctt | tgtggtagaa | acccagccct | gcatgcccca | aactcccct | cgacccctca | 1200 |
| tcctcaagac | tggcagcaag | ttcaccgtcc | gaacaaggct | gctggtgaga | ctccaggaag | 1260 |
| gcaatgagtc | actgactgtg | gaagtctcca | ttgacaggaa | tcctcctcaa | ttacaaggct | 1320 |
| tccggaagtt | caacattctg | acttcaaacc | agaaaacttt | gaccccgag | aaggggcaga | 1380 |
| gtcagggttt | gatttgggac | tttgttacc | tgactctggt | ggagcaacgt | tcaggtggtt | 1440 |
| caggaaaggg | cagcaataag | gggccactag | gtgtgacaga | ggaactgcac | atcatcagct | 1500 |
| tcacggtcaa | atatacctac | cagggtctga | gcaggagct | gaaaacggac | accctccctg | 1560 |
| tggtgattat | ttccaacatg | aaccagctct | caattgcctg | gcttcagtt | ctctggttca | 1620 |
| atttgctcag | cccaaaacctt | cagaaccagc | agttcttctc | caaccccccc | aaggccccct | 1680 |

-continued

```
ggagcttgct gggccctgct ctcagttggc agttctcctc ctatgttggc cgaggcctca    1740
actcagacca gctgagcatg ctgagaaaca agctgttcgg gcagaactgt aggactgagg    1800
atccattatt gtcctgggct gacttcacta agcgagagag ccctcctggc aagttaccat    1860
tctggacatg gctggacaaa attctggagt tggtacatga ccacctgaag gatctctgga    1920
atgatggacg catcatgggc tttgtgagtc ggagccagga gcgccggctg ctgaagaaga    1980
ccatgtctgg caccttttcta ctgcgcttca gtgaatcgtc agaaggggc attacctgct    2040 cctgggtgga gcaccaggat gatgacaagg tgctcatcta ctctgtgcaa ccgtacacga    2100
aggaggtgct gcagtcactc ccgctgactg aaatcatccg ccattaccag ttgctcactg    2160
aggagaatat acctgaaaac ccactgcgct tcctctatcc ccgaatcccc cgggatgaag    2220
cttttgggtg ctactaccag gagaaagtta atctccagga acggaggaaa tacctgaaac    2280
acaggctcat tgtggtctct aatagacagg tggatgaact gcaacaaccg ctggagctta    2340
agccagagcc agagctggag tcattagagc tggaactagg gctggtgcca gagccagagc    2400
tcagcctgga cttagagcca ctgctgaagg cagggctgga tctggggcca gagctagagt    2460
ctgtgctgga gtccactctg gagcctgtga tagagcccac actatgcatg gtatcacaaa    2520
cagtgccaga gccagaccaa ggacctgtat cacagccagt gccagagcca gatttgccct    2580
gtgatctgag acatttgaac actgagccaa tggaaatctt cagaaactgt gtaaagattg    2640
aagaaatcat gccgaatggt gacccactgt ggctggcca gaacaccgtg gatgaggttt    2700
acgtctcccg ccccagccac ttctacactg atggacccct tgatgccttct gacttctagg    2760 aaccacattt cctctgttct tttcatatct cttgcccttc ctactcctca tagcatgata    2820
ttgttctcca aggatgggaa tcaggcatgt gtcccttcca agctgtgtta actgttcaaa    2880
ctcaggcctg tgtgactcca ttggggtgag aggtgaaagc ataacatggg tacagagggg    2940
acaacaatga atcagaacag atgctgagcc ataggtctaa ataggatcct ggaggctgcc    3000
tgctgtgctg ggaggtatag gggtcctggg ggcaggccag ggcagttgac aggtacttgg    3060
agggctcagg gcagtggctt ctttccagta tggaaggatt tcaacatttt aatagttggt    3120
taggctaaac tggtgcatac tggcattggc ccttggtggg gagcacagac acaggatagg    3180
actccatttc tttcttccat tccttcatgt ctaggataac ttgctttctt ctttcctta    3240 ctcctggctc aagccctgaa tttcttcttt tcctgcaggg gttgagagct ttctgcctta    3300
gcctaccatg tgaaactcta ccctgaagaa agggatggat aggaagtaga cctcttttc    3360 ttaccagtct cctcccctac tctgccccta agctggctgt acctgttcct cccccataaa    3420
atgatcctgc caatctaatg tgagtgtgaa gctttgcaca ctagtttatg ctacctagtc    3480
tccactttct caatgcttag gagacagatc actcctggag gctggggatg gtaggattgc    3540
tggggatttt ttttttttta aacagggtct cactctgttg cccaggctag agtgcaatgg    3600
tgcaatcaca gctcactgca gcctcaacct cctgggttca agcaatcctc ctacctcagc    3660
ctcctgggta gctagcacca tggcatgcgc caccatgccc tatttttttt ttttaaagac    3720
agggtcttgc tatattgccc aggctggtct tgaactgggc tcaagtgatc ctcacgcctt    3780
ggcctcccaa agtgctggga ttataggcat gagccactgt gcttggccag gatttttttt    3840
tttttttttt tgagatggag tttctctctt gttgtccagg ctggagtgca atggtgtgat    3900
ctcggctcac tgcaacctcc gccttccggg ttcaagtgac tctcctgcct cagcctcccc    3960
agtagctggg attacagatc tgcaccacca tgcccagcta ttttgtatt tttagtagag    4020 acggggtttc tccatgttgg tcaggctggt ctcgaactcc tgacctcaag tgatctgtcc    4080
```

```
acctcggcct cccagagtgc tgggattaca ggcgtgagcc actgttccca gcaggaattt    4140
cttttttata gtattggata aagtttggtg ttttacaga ggagaagcaa tgggtcttag    4200
ctctttctct attatgttat catcctccct ttttgtaca atatgttgtt tacctgaaag    4260
gaaggtttct attcgttggt tgtggacctg gacaaagtcc aagtctgtgg aacttaaaac    4320
cttgaaggtc tgtcatagga ctctggacaa tctcacacct tagctattcc cagggaaccc    4380 caggggcaa ctgacattgc tccaagatgt tctcctgatg tagcttgaga tataaaggaa    4440
aggccctgca caggtggctg tttcttgtct gttatgtcag aggaacagtc ctgttcagaa    4500
aggggctctt ctgagcagaa atggctaata aactttgtgc tgatctggaa aaaaaaaaa    4560 aaaaaaaaaa aaaaaa                                                    4576
```

<210> SEQ ID NO 22
<211> LENGTH: 851
<212> TYPE: PRT
<213> ORGANISM: Homo sapiens

<400> SEQUENCE: 22

```
Met Ala Gln Trp Glu Met Leu Gln Asn Leu Asp Ser Pro Phe Gln Asp
1               5                   10                  15

Gln Leu His Gln Leu Tyr Ser His Ser Leu Leu Pro Val Asp Ile Arg
            20                  25                  30

Gln Tyr Leu Ala Val Trp Ile Glu Asp Gln Asn Trp Gln Glu Ala Ala
        35                  40                  45

Leu Gly Ser Asp Asp Ser Lys Ala Thr Met Leu Phe Phe His Phe Leu
    50                  55                  60

Asp Gln Leu Asn Tyr Glu Cys Gly Arg Cys Ser Gln Asp Pro Glu Ser
65                  70                  75                  80

Leu Leu Leu Gln His Asn Leu Arg Lys Phe Cys Arg Asp Ile Gln Pro
                85                  90                  95

Phe Ser Gln Asp Pro Thr Gln Leu Ala Glu Met Ile Phe Asn Leu Leu
            100                 105                 110

Leu Glu Glu Lys Arg Ile Leu Ile Gln Ala Gln Arg Ala Gln Leu Glu
        115                 120                 125

Gln Gly Glu Pro Val Leu Glu Thr Pro Val Glu Ser Gln Gln His Glu
    130                 135                 140

Ile Glu Ser Arg Ile Leu Asp Leu Arg Ala Met Met Glu Lys Leu Val
145                 150                 155                 160

Lys Ser Ile Ser Gln Leu Lys Asp Gln Gln Asp Val Phe Cys Phe Arg
                165                 170                 175

Tyr Lys Ile Gln Ala Lys Gly Lys Thr Pro Ser Leu Asp Pro His Gln
            180                 185                 190

Thr Lys Glu Gln Lys Ile Leu Gln Glu Thr Leu Asn Glu Leu Asp Lys
        195                 200                 205

Arg Arg Lys Glu Val Leu Asp Ala Ser Lys Ala Leu Leu Gly Arg Leu
    210                 215                 220

Thr Thr Leu Ile Glu Leu Leu Pro Lys Leu Glu Glu Trp Lys Ala
225                 230                 235                 240

Gln Gln Gln Lys Ala Cys Ile Arg Ala Pro Ile Asp His Gly Leu Glu
                245                 250                 255

Gln Leu Glu Thr Trp Phe Thr Ala Gly Ala Lys Leu Leu Phe His Leu
            260                 265                 270

Arg Gln Leu Leu Lys Glu Leu Lys Gly Leu Ser Cys Leu Val Ser Tyr
        275                 280                 285
```

```
Gln Asp Asp Pro Leu Thr Lys Gly Val Asp Leu Arg Asn Ala Gln Val
    290                 295                 300

Thr Glu Leu Leu Gln Arg Leu Leu His Arg Ala Phe Val Val Glu Thr
305                 310                 315                 320

Gln Pro Cys Met Pro Gln Thr Pro His Arg Pro Leu Ile Leu Lys Thr
                325                 330                 335

Gly Ser Lys Phe Thr Val Arg Thr Arg Leu Leu Val Arg Leu Gln Glu
            340                 345                 350

Gly Asn Glu Ser Leu Thr Val Glu Val Ser Ile Asp Arg Asn Pro Pro
        355                 360                 365

Gln Leu Gln Gly Phe Arg Lys Phe Asn Ile Leu Thr Ser Asn Gln Lys
    370                 375                 380

Thr Leu Thr Pro Glu Lys Gly Gln Ser Gln Gly Leu Ile Trp Asp Phe
385                 390                 395                 400

Gly Tyr Leu Thr Leu Val Glu Gln Arg Ser Gly Ser Gly Lys Gly
                405                 410                 415

Ser Asn Lys Gly Pro Leu Gly Val Thr Glu Glu Leu His Ile Ile Ser
            420                 425                 430

Phe Thr Val Lys Tyr Thr Tyr Gln Gly Leu Lys Gln Glu Leu Lys Thr
        435                 440                 445

Asp Thr Leu Pro Val Val Ile Ile Ser Asn Met Asn Gln Leu Ser Ile
    450                 455                 460

Ala Trp Ala Ser Val Leu Trp Phe Asn Leu Leu Ser Pro Asn Leu Gln
465                 470                 475                 480

Asn Gln Gln Phe Phe Ser Asn Pro Pro Lys Ala Pro Trp Ser Leu Leu
                485                 490                 495

Gly Pro Ala Leu Ser Trp Gln Phe Ser Ser Tyr Val Gly Arg Gly Leu
            500                 505                 510

Asn Ser Asp Gln Leu Ser Met Leu Arg Asn Lys Leu Phe Gly Gln Asn
        515                 520                 525

Cys Arg Thr Glu Asp Pro Leu Leu Ser Trp Ala Asp Phe Thr Lys Arg
    530                 535                 540

Glu Ser Pro Pro Gly Lys Leu Pro Phe Trp Thr Trp Leu Asp Lys Ile
545                 550                 555                 560

Leu Glu Leu Val His Asp His Leu Lys Asp Leu Trp Asn Asp Gly Arg
                565                 570                 575

Ile Met Gly Phe Val Ser Arg Ser Gln Glu Arg Leu Leu Lys Lys
            580                 585                 590

Thr Met Ser Gly Thr Phe Leu Leu Arg Phe Ser Glu Ser Ser Glu Gly
        595                 600                 605

Gly Ile Thr Cys Ser Trp Val Glu His Gln Asp Asp Lys Val Leu
    610                 615                 620

Ile Tyr Ser Val Gln Pro Tyr Thr Lys Glu Val Leu Gln Ser Leu Pro
625                 630                 635                 640

Leu Thr Glu Ile Ile Arg His Tyr Gln Leu Leu Thr Glu Glu Asn Ile
                645                 650                 655

Pro Glu Asn Pro Leu Arg Phe Leu Tyr Pro Arg Ile Pro Arg Asp Glu
            660                 665                 670

Ala Phe Gly Cys Tyr Tyr Gln Glu Lys Val Asn Leu Gln Glu Arg Arg
        675                 680                 685

Lys Tyr Leu Lys His Arg Leu Ile Val Val Ser Asn Arg Gln Val Asp
    690                 695                 700
```

```
Glu Leu Gln Gln Pro Leu Glu Leu Lys Pro Glu Pro Glu Leu Glu Ser
705                 710                 715                 720

Leu Glu Leu Glu Leu Gly Leu Val Pro Glu Pro Glu Leu Ser Leu Asp
            725                 730                 735

Leu Glu Pro Leu Leu Lys Ala Gly Leu Asp Leu Gly Pro Glu Leu Glu
        740                 745                 750

Ser Val Leu Glu Ser Thr Leu Glu Pro Val Ile Glu Pro Thr Leu Cys
        755                 760                 765

Met Val Ser Gln Thr Val Pro Glu Pro Asp Gln Gly Pro Val Ser Gln
    770                 775                 780

Pro Val Pro Glu Pro Asp Leu Pro Cys Asp Leu Arg His Leu Asn Thr
785                 790                 795                 800

Glu Pro Met Glu Ile Phe Arg Asn Cys Val Lys Ile Glu Glu Ile Met
                805                 810                 815

Pro Asn Gly Asp Pro Leu Leu Ala Gly Gln Asn Thr Val Asp Glu Val
            820                 825                 830

Tyr Val Ser Arg Pro Ser His Phe Tyr Thr Asp Gly Pro Leu Met Pro
        835                 840                 845

Ser Asp Phe
    850

<210> SEQ ID NO 23
<211> LENGTH: 4564
<212> TYPE: DNA
<213> ORGANISM: Homo sapiens

<400> SEQUENCE: 23
tggcagccag tgtcggggtg gcggctggga atgggggccg ctccggactt ccgctgccaa      60
ctacaagggg gcgggtccga gggggttag ccgaagttgt aggcggggcg cgaggttcta     120
gtacccgagc tcatactagg acgggaagt cgcgaccaga gccattggag ggcgcgggga     180
ctgcaaccct aatcagagcc caaatggcgc agtgggaaat gctgcagaat cttgacagcc     240
cctttcagga tcagctgcac cagctttact cgcacagcct cctgctgtga cattcgac       300 agtacttggc tgtctggatt gaagaccaga actggcagga agctgcactt gggagtgatg     360
attccaaggc taccatgcta ttcttccact tcttggatca gctgaactat gagtgtggcc     420
gttgcagcca ggacccagag tccttgttgc tgcagcacaa tttgcggaaa ttctgccggg     480
acattcagga tcctacccag ttggctgaga tgatctttaa cctccttctg gaagaaaaaa     540
gaattttgat ccaggctcag agggcccaat tggaacaagg agagccagtt ctcgaaacac     600
ctgtggagag ccagcaacat gagattgaat cccggatcct ggatttaagg gctatgatgg     660
agaagctggt aaaatccatc agccaactga agaccagca ggatgtcttc tgcttccgat      720
ataagatcca ggccaaaggg aagacaccct ctctggaccc ccatcagacc aaagagcaga     780
agattctgca ggaaactctc aatgaactgg acaaaggag aaaggaggtg ctggatgcct     840
ccaaagcact gctaggccga ttaactaccc taatcgagct actgctgcca agttggagg      900 agtggaaggc ccagcagcaa aaagcctgca tcagagctcc cattgaccac gggttggaac     960
agctggagac atggttcaca gctggagcaa agctgttgtt tcacctgagg cagctgctga    1020
aggagctgaa gggactgagt tgcctggtta gctatcagga tgaccctctg accaaagggg    1080
tggacctacg caacgcccag gtcacagagt tgctacagcg tctgctccac agagcctttg    1140
tggtagaaac ccagcctgc atgccccaaa ctccccatcg acccctcatc ctcaagactg      1200
gcagcaagtt caccgtccga acaaggctgc tggtgagact ccaggaaggc aatgagtcac    1260
```

```
tgactgtgga agtctccatt gacaggaatc ctcctcaatt acaaggcttc cggaagttca    1320
acattctgac ttcaaaccag aaaactttga cccccgagaa ggggcagagt cagggtttga    1380
tttgggactt tggttacctg actctggtgg agcaacgttc aggtggttca ggaaagggca    1440
gcaataaggg gccactaggt gtgacagagg aactgcacat catcagcttc acggtcaaat    1500
atacctacca gggtctgaag caggagctga aaacggacac cctccctgtg gtgattattt    1560
ccaacatgaa ccagctctca attgcctggg cttcagttct ctggttcaat ttgctcagcc    1620
caaaccttca gaaccagcag ttcttctcca accccccaa ggcccctgg agcttgctgg     1680 gccctgctct cagttggcag ttctcctcct atgttggccg aggcctcaac tcagaccagc    1740
tgagcatgct gagaaacaag ctgttcgggc agaactgtag gactgaggat ccattattgt    1800
cctgggctga cttcactaag cgagagagcc ctcctggcaa gttaccattc tggacatggc    1860
tggacaaaat tctggagttg gtacatgacc acctgaagga tctctggaat gatggacgca    1920
tcatgggctt tgtgagtcgg agccaggagc gccggctgct gaagaagacc atgtctggca    1980
cctttctact gcgcttcagt gaatcgtcag aagggggcat tacctgctcc tgggtggagc    2040
accaggatga tgacaaggtg ctcatctact ctgtgcaacc gtacacgaag gaggtgctgc    2100
agtcactccc gctgactgaa atcatccgcc attaccagtt gctcactgag gagaatatac    2160
ctgaaacccc actgcgcttc ctctatcccc gaatccccg ggatgaagct tttgggtgct    2220
actaccagga gaaagttaat ctccaggaac ggaggaaata cctgaaacac aggctcattg    2280
tggtctctaa tagacaggtg gatgaactgc aacaaccgct ggagcttaag ccagagccag    2340
agctggagtc attagagctg gaactagggc tggtgccaga gccagagctc agcctggact    2400
tagagccact gctgaaggca gggctggatc tggggccaga gctagagtct gtgctggagt    2460
ccactctgga gcctgtgata gagcccacac tatgcatggt atcacaaaca gtgccagagc    2520
cagaccaagg acctgtatca cagccagtgc cagagccaga tttgccctgt gatctgagac    2580
atttgaacac tgagccaatg gaaatcttca gaaactgtgt aaagattgaa gaatcatgc    2640 cgaatggtga cccactgttg gctggccaga acaccgtgga tgaggtttac gtctcccgcc    2700
ccagccactt ctacactgat ggaccccttga tgccttctga cttctaggaa ccacatttcc    2760
tctgttcttt tcatatctct tgcccttcct actcctcata gcatgatatt gttctccaag    2820
gatgggaatc aggcatgtgt cccttccaag ctgtgttaac tgttcaaact caggcctgtg    2880
tgactccatt ggggtgagag gtgaaagcat aacatgggta cagaggggac aacaatgaat    2940
cagaacagat gctgagccat aggtctaaat aggatcctgg aggctgcctg ctgtgctggg    3000
aggtataggg gtcctggggg caggccaggg cagttgacag gtacttggag ggctcagggc    3060
agtggcttct ttccagtatg gaaggatttc aacattttaa tagttggtta ggctaaactg    3120
gtgcatactg gcattggccc ttggtgggga gcacagacac aggataggac tccatttctt    3180
tcttccattc cttcatgtct aggataactt gctttcttct ttcctttact cctggctcaa    3240
gccctgaatt tcttcttttc ctgcaggggt tgagagcttt ctgccttagc ctaccatgtg    3300
aaactctacc ctgaagaaag ggatggatag gaagtagacc tctttttctt accagtctcc    3360
tcccctactc tgcccctaag ctggctgtac ctgttcctcc cccataaaat gatcctgcca    3420
atctaatgtg agtgtgaagc tttgcacact agtttatgct acctagtctc cactttctca    3480
atgcttagga gacagatcac tcctggaggc tggggatggt aggattgctg ggatttttt    3540 ttttttaaa caggggtctca ctctgttgcc caggctagag tgcaatgtg caatcacagc     3600 tcactgcagc ctcaaccctcc tgggttcaag caatcctcct acctcagcct cctgggtagc    3660
```

-continued

```
tagcaccatg gcatgcgcca ccatgcccta tttttttttt ttaaagacag ggtcttgcta    3720
tattgcccag gctggtcttg aactgggctc aagtgatcct cacgccttgg cctcccaaag    3780
tgctgggatt ataggcatga gccactgtgc ttggccagga tttttttttt tttttttttg    3840
agatggagtt tctctcttgt tgtccaggct ggagtgcaat ggtgtgatct cggctcactg    3900
caacctccgc cttccgggtt caagtgactc tcctgcctca gcctcccag tagctgggat     3960 tacagatctg caccaccatg cccagctaat tttgtatttt tagtagagac ggggtttctc    4020
catgttggtc aggctggtct cgaactcctg acctcaagtg atctgtccac ctcggcctcc    4080
cagagtgctg ggattacagg cgtgagccac tgttcccagc aggaatttct tttttatagt    4140
attggataaa gtttggtgtt tttacagagg agaagcaatg ggtcttagct ctttctctat    4200
tatgttatca tcctcccttt tttgtacaat atgttgttta cctgaaagga aggtttctat    4260
tcgttggttg tggacctgga caaagtccaa gtctgtggaa cttaaaacct tgaaggtctg    4320
tcataggact ctggacaatc tcacaccttα gctattccca gggaacccca gggggcaact    4380
gacattgctc caagatgttc tcctgatgta gcttgagata taaaggaaag gccctgcaca    4440
ggtggctgtt tcttgtctgt tatgtcagag gaacagtcct gttcagaaag gggctcttct    4500
gagcagaaat ggctaataaa ctttgtgctg atctggaaaa aaaaaaaaa aaaaaaaaa      4560 aaaa                                                                 4564
```

```
<210> SEQ ID NO 24
<211> LENGTH: 847
<212> TYPE: PRT
<213> ORGANISM: Homo sapiens

<400> SEQUENCE: 24
```

Met Ala Gln Trp Glu Met Leu Gln Asn Leu Asp Ser Pro Phe Gln Asp
1               5                   10                  15

Gln Leu His Gln Leu Tyr Ser His Ser Leu Leu Pro Val Asp Ile Arg
            20                  25                  30

Gln Tyr Leu Ala Val Trp Ile Glu Asp Gln Asn Trp Gln Glu Ala Ala
        35                  40                  45

Leu Gly Ser Asp Asp Ser Lys Ala Thr Met Leu Phe Phe His Phe Leu
    50                  55                  60

Asp Gln Leu Asn Tyr Glu Cys Gly Arg Cys Ser Gln Asp Pro Glu Ser
65                  70                  75                  80

Leu Leu Leu Gln His Asn Leu Arg Lys Phe Cys Arg Asp Ile Gln Asp
                85                  90                  95

Pro Thr Gln Leu Ala Glu Met Ile Phe Asn Leu Leu Leu Glu Glu Lys
            100                 105                 110

Arg Ile Leu Ile Gln Ala Gln Arg Ala Gln Leu Glu Gln Gly Glu Pro
        115                 120                 125

Val Leu Glu Thr Pro Val Glu Ser Gln Gln His Glu Ile Glu Ser Arg
    130                 135                 140

Ile Leu Asp Leu Arg Ala Met Met Glu Lys Leu Val Lys Ser Ile Ser
145                 150                 155                 160

Gln Leu Lys Asp Gln Gln Asp Val Phe Cys Phe Arg Tyr Lys Ile Gln
                165                 170                 175

Ala Lys Gly Lys Thr Pro Ser Leu Asp Pro His Gln Thr Lys Glu Gln
            180                 185                 190

Lys Ile Leu Gln Glu Thr Leu Asn Glu Leu Asp Lys Arg Arg Lys Glu
        195                 200                 205

```
Val Leu Asp Ala Ser Lys Ala Leu Leu Gly Arg Leu Thr Thr Leu Ile
    210                 215                 220
Glu Leu Leu Leu Pro Lys Leu Glu Glu Trp Lys Ala Gln Gln Gln Lys
225                 230                 235                 240
Ala Cys Ile Arg Ala Pro Ile Asp His Gly Leu Glu Gln Leu Glu Thr
                245                 250                 255
Trp Phe Thr Ala Gly Ala Lys Leu Leu Phe His Leu Arg Gln Leu Leu
            260                 265                 270
Lys Glu Leu Lys Gly Leu Ser Cys Leu Val Ser Tyr Gln Asp Asp Pro
        275                 280                 285
Leu Thr Lys Gly Val Asp Leu Arg Asn Ala Gln Val Thr Glu Leu Leu
    290                 295                 300
Gln Arg Leu Leu His Arg Ala Phe Val Val Glu Thr Gln Pro Cys Met
305                 310                 315                 320
Pro Gln Thr Pro His Arg Pro Leu Ile Leu Lys Thr Gly Ser Lys Phe
                325                 330                 335
Thr Val Arg Thr Arg Leu Leu Val Arg Leu Gln Glu Gly Asn Glu Ser
            340                 345                 350
Leu Thr Val Glu Val Ser Ile Asp Arg Asn Pro Pro Gln Leu Gln Gly
        355                 360                 365
Phe Arg Lys Phe Asn Ile Leu Thr Ser Asn Gln Lys Thr Leu Thr Pro
    370                 375                 380
Glu Lys Gly Gln Ser Gln Gly Leu Ile Trp Asp Phe Gly Tyr Leu Thr
385                 390                 395                 400
Leu Val Glu Gln Arg Ser Gly Ser Gly Lys Gly Ser Asn Lys Gly
                405                 410                 415
Pro Leu Gly Val Thr Glu Leu His Ile Ile Ser Phe Thr Val Lys
            420                 425                 430
Tyr Thr Tyr Gln Gly Leu Lys Gln Glu Leu Lys Thr Asp Thr Leu Pro
        435                 440                 445
Val Val Ile Ile Ser Asn Met Asn Gln Leu Ser Ile Ala Trp Ala Ser
    450                 455                 460
Val Leu Trp Phe Asn Leu Leu Ser Pro Asn Leu Gln Asn Gln Gln Phe
465                 470                 475                 480
Phe Ser Asn Pro Pro Lys Ala Pro Trp Ser Leu Leu Gly Pro Ala Leu
                485                 490                 495
Ser Trp Gln Phe Ser Ser Tyr Val Gly Arg Gly Leu Asn Ser Asp Gln
            500                 505                 510
Leu Ser Met Leu Arg Asn Lys Leu Phe Gly Gln Asn Cys Arg Thr Glu
        515                 520                 525
Asp Pro Leu Leu Ser Trp Ala Asp Phe Thr Lys Arg Glu Ser Pro Pro
    530                 535                 540
Gly Lys Leu Pro Phe Trp Thr Trp Leu Asp Lys Ile Leu Glu Leu Val
545                 550                 555                 560
His Asp His Leu Lys Asp Leu Trp Asn Asp Gly Arg Ile Met Gly Phe
                565                 570                 575
Val Ser Arg Ser Gln Glu Arg Arg Leu Leu Lys Lys Thr Met Ser Gly
            580                 585                 590
Thr Phe Leu Leu Arg Phe Ser Glu Ser Ser Glu Gly Gly Ile Thr Cys
        595                 600                 605
Ser Trp Val Glu His Gln Asp Asp Asp Lys Val Leu Ile Tyr Ser Val
    610                 615                 620
```

| Gln | Pro | Tyr | Thr | Lys | Glu | Val | Leu | Gln | Ser | Leu | Pro | Leu | Thr | Glu | Ile |
|---|---|---|---|---|---|---|---|---|---|---|---|---|---|---|---|
| 625 | | | | | 630 | | | | | 635 | | | | | 640 |

| Ile | Arg | His | Tyr | Gln | Leu | Leu | Thr | Glu | Glu | Asn | Ile | Pro | Glu | Asn | Pro |
|---|---|---|---|---|---|---|---|---|---|---|---|---|---|---|---|
| | | | | 645 | | | | | 650 | | | | | 655 | |

| Leu | Arg | Phe | Leu | Tyr | Pro | Arg | Ile | Pro | Arg | Asp | Glu | Ala | Phe | Gly | Cys |
|---|---|---|---|---|---|---|---|---|---|---|---|---|---|---|---|
| | | | 660 | | | | | 665 | | | | | 670 | | |

| Tyr | Tyr | Gln | Glu | Lys | Val | Asn | Leu | Gln | Glu | Arg | Arg | Lys | Tyr | Leu | Lys |
|---|---|---|---|---|---|---|---|---|---|---|---|---|---|---|---|
| | | 675 | | | | | 680 | | | | | 685 | | | |

| His | Arg | Leu | Ile | Val | Val | Ser | Asn | Arg | Gln | Val | Asp | Glu | Leu | Gln | Gln |
|---|---|---|---|---|---|---|---|---|---|---|---|---|---|---|---|
| | 690 | | | | | 695 | | | | | 700 | | | | |

| Pro | Leu | Glu | Leu | Lys | Pro | Glu | Pro | Glu | Leu | Glu | Ser | Leu | Glu | Leu | Glu |
|---|---|---|---|---|---|---|---|---|---|---|---|---|---|---|---|
| 705 | | | | | 710 | | | | | 715 | | | | | 720 |

| Leu | Gly | Leu | Val | Pro | Glu | Pro | Glu | Leu | Ser | Leu | Asp | Leu | Glu | Pro | Leu |
|---|---|---|---|---|---|---|---|---|---|---|---|---|---|---|---|
| | | | | 725 | | | | | 730 | | | | | 735 | |

| Leu | Lys | Ala | Gly | Leu | Asp | Leu | Gly | Pro | Glu | Leu | Glu | Ser | Val | Leu | Glu |
|---|---|---|---|---|---|---|---|---|---|---|---|---|---|---|---|
| | | | 740 | | | | | 745 | | | | | 750 | | |

| Ser | Thr | Leu | Glu | Pro | Val | Ile | Glu | Pro | Thr | Leu | Cys | Met | Val | Ser | Gln |
|---|---|---|---|---|---|---|---|---|---|---|---|---|---|---|---|
| | | 755 | | | | | 760 | | | | | 765 | | | |

| Thr | Val | Pro | Glu | Pro | Asp | Gln | Gly | Pro | Val | Ser | Gln | Pro | Val | Pro | Glu |
|---|---|---|---|---|---|---|---|---|---|---|---|---|---|---|---|
| | 770 | | | | | 775 | | | | | 780 | | | | |

| Pro | Asp | Leu | Pro | Cys | Asp | Leu | Arg | His | Leu | Asn | Thr | Glu | Pro | Met | Glu |
|---|---|---|---|---|---|---|---|---|---|---|---|---|---|---|---|
| 785 | | | | | 790 | | | | | 795 | | | | | 800 |

| Ile | Phe | Arg | Asn | Cys | Val | Lys | Ile | Glu | Glu | Ile | Met | Pro | Asn | Gly | Asp |
|---|---|---|---|---|---|---|---|---|---|---|---|---|---|---|---|
| | | | | 805 | | | | | 810 | | | | | 815 | |

| Pro | Leu | Leu | Ala | Gly | Gln | Asn | Thr | Val | Asp | Glu | Val | Tyr | Val | Ser | Arg |
|---|---|---|---|---|---|---|---|---|---|---|---|---|---|---|---|
| | | | 820 | | | | | 825 | | | | | 830 | | |

| Pro | Ser | His | Phe | Tyr | Thr | Asp | Gly | Pro | Leu | Met | Pro | Ser | Asp | Phe |
|---|---|---|---|---|---|---|---|---|---|---|---|---|---|---|
| | | 835 | | | | | 840 | | | | | 845 | | |

<210> SEQ ID NO 25
<211> LENGTH: 2656
<212> TYPE: DNA
<213> ORGANISM: Homo sapiens

<400> SEQUENCE: 25

| | | |
|---|---|---|
| ttacattcgg cttcttccta atgtcaaatg agtgctgtta aagttcctcc aggaaacttc | 60 |
| agcagagaaa acatttgct tcacatctca tcaaatcttc tgcatcaagc cacatcatgt | 120 |
| taaacaacct tctgctgttc tcccttcaga taagtctcat aggaaccact cttggtggga | 180 |
| atgttttgat ttggccaatg gaaggtagtc attggctaaa tgttaagata attatagatg | 240 |
| agctcattaa aaaggagcat aatgtgactg tcctagttgc ctctggtgca cttttcatca | 300 |
| caccaacctc taacccatct ctgacatttg aaatatatag ggtgcccttt ggcaaagaaa | 360 |
| gaatagaagg agtaattaag gacttcgttt tgacatggct ggaaaataga ccatctcctt | 420 |
| caaccatttg gagattctat caggagatgg ccaaagtaat caaggacttc cacatggtgt | 480 |
| ctcaggagat ctgtgatggc gttcttaaaa accaacagct gatggcaaag ctaaagaaaa | 540 |
| gcaagtttga agtcctggtg tctgatccag tatttccttg tggcgatata gtagctttaa | 600 |
| aacttggaat tccatttatg tactccttga ggttttctcc agcctcaaca gtggaaaagc | 660 |
| actgtgggaa ggtaccatac cctccttcct atgttcctgc tgttttatca gaactcaccg | 720 |
| accaaatgtc tttcactgac agaataagaa atttcatctc ctaccaccta caggactaca | 780 |
| tgtttgaaac tctttggaaa tcatgggatt catactatag taaagcttta ggaagaccca | 840 |
| ctacgttatg tgagactatg gggaaagctg aaatttggtt aatccgaaca tattgggatt | 900 |

```
ttgaatttcc tcgtccatac ttacctaatt ttgagtttgt tggaggattg cactgcaaac    960
ctgccaaacc tttacctaag gaaatggaag aatttatcca gagctcaggt aaaaatggtg   1020
ttgtggtgtt ttctctggga tcaatggtca aaaaccttac agaagaaaag gccaatctta   1080
ttgcctcagc ccttgcccag attccacaga aggttttatg gagatacaaa ggaaagaaac   1140
cagccacatt aggaaacaat actcagctct ttgattggat accccagaat gatcttcttg   1200
gacatcccaa aaccaaagct tttatcactc atggtggaac taatgggatc tacgaagcta   1260
tttaccacgg agtccctatg gtgggagttc ccatgtttgc tgatcagcct gataacattg   1320
ctcacatgaa ggccaaagga gcagctgtgg aagtgaacct aaacacaatg acaagtgtgg   1380
atttgcttag cgcttttgaga acagtcatta atgaaccttc ttataaagag aatgctatga   1440
ggttatcaag aattcaccat gatcaacctg taaagcccct ggatcgagca gtcttctgga   1500
tcgagtttgt catgcgccac aaaggagcca agcaccttcg ggttgcagcc catgacctca   1560
cctggttcca gtaccactct ttggatgtaa ttgggttctt gctggtctgt gtgacaacgg   1620
ctatattttt ggtcatacaa tgttgtttgt tttcctgtca aaaatttggt aagataggaa   1680
agaagaaaaa aagagaatag gtcaagaaaa agaggaaata tatatatttt taagtttggc   1740
aaaatcctga gtagtgtagt cctattaatt ccagacaaaa ggagtttaac aaaaacacgt   1800
ctcccatcct gtttccaaat tttctatttc tctacctgcg ataagcctac tgataaagcc   1860
tagattttgg catgattatt attaacttgt gagttatagt cttctatttt tcctttgtct   1920
ctccctgctg actataccct cttcctgtca cttttctgac acaaggatac tacctaattt   1980
taaatatgtt ctattcatag tatcaaatta ttttatcgtt aaccttaatt aatgattaac   2040
aatatgctga atcctggtaa tgcatacagt gtagatggaa tttgataggt gtaaggaaga   2100
gtcaaattca caaatttcca tataccaaac aaatcaggga gccaccgtag gagagtagtg   2160
tgttatgaga aaggtaatga tttccttttt taataaaaac aaactcttct gcttgctcaa   2220
tgtttcagga gttagagaat gaattttaag tgtgacgtgc gtccctatta aatgtctaca   2280
aaatttttcat taagcatatc tagaaaatca cggcataact tgcctgcctt tcttcaacat   2340
atattcttat ataacctgta gtggaagatt tgggtactgt ctttaataaa tcaatcaatc   2400
gactctttta tttcaaggag aaagttctat gttatatgtt gaaggtgaac agatcatatt   2460
tagaggatat aacaattaga aatctagaaa ataattatca tttttataaa attttttagtc   2520
aactgtacaa ataattacat aaaacatcaa ttaattatgc ttaaaaatca ctaatgttca   2580
taatatataa tcactatttg taatcaaaag tttaatttta tgccaaaaaa taaaaaatgc   2640
ttacttggaa tttgaa                                                   2656
```

<210> SEQ ID NO 26  
<211> LENGTH: 527  
<212> TYPE: PRT  
<213> ORGANISM: Homo sapiens

<400> SEQUENCE: 26

```
Met Leu Asn Asn Leu Leu Leu Phe Ser Leu Gln Ile Ser Leu Ile Gly
1               5                  10                  15

Thr Thr Leu Gly Gly Asn Val Leu Ile Trp Pro Met Glu Gly Ser His
            20                  25                  30

Trp Leu Asn Val Lys Ile Ile Ile Asp Glu Leu Ile Lys Lys Glu His
        35                  40                  45

Asn Val Thr Val Leu Val Ala Ser Gly Ala Leu Phe Ile Thr Pro Thr
    50                  55                  60
```

Ser Asn Pro Ser Leu Thr Phe Glu Ile Tyr Arg Val Pro Phe Gly Lys
65                  70                  75                  80

Glu Arg Ile Glu Gly Val Ile Lys Asp Phe Val Leu Thr Trp Leu Glu
                85                  90                  95

Asn Arg Pro Ser Pro Ser Thr Ile Trp Arg Phe Tyr Gln Glu Met Ala
            100                 105                 110

Lys Val Ile Lys Asp Phe His Met Val Ser Gln Glu Ile Cys Asp Gly
        115                 120                 125

Val Leu Lys Asn Gln Gln Leu Met Ala Lys Leu Lys Ser Lys Phe
    130                 135                 140

Glu Val Leu Val Ser Asp Pro Val Phe Pro Cys Gly Asp Ile Val Ala
145                 150                 155                 160

Leu Lys Leu Gly Ile Pro Phe Met Tyr Ser Leu Arg Phe Ser Pro Ala
                165                 170                 175

Ser Thr Val Glu Lys His Cys Gly Lys Val Pro Tyr Pro Pro Ser Tyr
            180                 185                 190

Val Pro Ala Val Leu Ser Glu Leu Thr Asp Gln Met Ser Phe Thr Asp
        195                 200                 205

Arg Ile Arg Asn Phe Ile Ser Tyr His Leu Gln Asp Tyr Met Phe Glu
    210                 215                 220

Thr Leu Trp Lys Ser Trp Asp Ser Tyr Tyr Ser Lys Ala Leu Gly Arg
225                 230                 235                 240

Pro Thr Thr Leu Cys Glu Thr Met Gly Lys Ala Glu Ile Trp Leu Ile
                245                 250                 255

Arg Thr Tyr Trp Asp Phe Glu Phe Pro Arg Pro Tyr Leu Pro Asn Phe
            260                 265                 270

Glu Phe Val Gly Gly Leu His Cys Lys Pro Ala Lys Pro Leu Pro Lys
        275                 280                 285

Glu Met Glu Glu Phe Ile Gln Ser Ser Gly Lys Asn Gly Val Val Val
    290                 295                 300

Phe Ser Leu Gly Ser Met Val Lys Asn Leu Thr Glu Glu Lys Ala Asn
305                 310                 315                 320

Leu Ile Ala Ser Ala Leu Ala Gln Ile Pro Gln Lys Val Leu Trp Arg
                325                 330                 335

Tyr Lys Gly Lys Lys Pro Ala Thr Leu Gly Asn Asn Thr Gln Leu Phe
            340                 345                 350

Asp Trp Ile Pro Gln Asn Asp Leu Leu Gly His Pro Lys Thr Lys Ala
        355                 360                 365

Phe Ile Thr His Gly Gly Thr Asn Gly Ile Tyr Glu Ala Ile Tyr His
    370                 375                 380

Gly Val Pro Met Val Gly Val Pro Met Phe Ala Asp Gln Pro Asp Asn
385                 390                 395                 400

Ile Ala His Met Lys Ala Lys Gly Ala Ala Val Glu Val Asn Leu Asn
                405                 410                 415

Thr Met Thr Ser Val Asp Leu Leu Ser Ala Leu Arg Thr Val Ile Asn
            420                 425                 430

Glu Pro Ser Tyr Lys Glu Asn Ala Met Arg Leu Ser Arg Ile His His
        435                 440                 445

Asp Gln Pro Val Lys Pro Leu Asp Arg Ala Val Phe Trp Ile Glu Phe
    450                 455                 460

Val Met Arg His Lys Gly Ala Lys His Leu Arg Val Ala Ala His Asp
465                 470                 475                 480

Leu Thr Trp Phe Gln Tyr His Ser Leu Asp Val Ile Gly Phe Leu Leu
            485                 490                 495

Val Cys Val Thr Thr Ala Ile Phe Leu Val Ile Gln Cys Cys Leu Phe
        500                 505                 510

Ser Cys Gln Lys Phe Gly Lys Ile Gly Lys Lys Lys Arg Glu
        515                 520                 525

<210> SEQ ID NO 27
<211> LENGTH: 3154
<212> TYPE: DNA
<213> ORGANISM: Homo sapiens

<400> SEQUENCE: 27

| | | | | | |
|---|---|---|---|---|---|
| ttacattcgg | cttcttccta | atgtcaaatg | agtgctgtta | aagttcctcc | aggaaacttc | 60 |
| agcagagaaa | aacatttgct | tcacatctca | tcaaatcttc | tgcatcaagc | cacatcatgt | 120 |
| taaacaacct | tctgctgttc | tcccttcaga | taagtctcat | aggaaccact | cttggtggga | 180 |
| atgttttgat | ttggccaatg | gaaggtagtc | attggctaaa | tgttaagata | attatagatg | 240 |
| agctcattaa | aaaggagcat | aatgtgactg | tcctagttgc | ctctggtgca | cttttcatca | 300 |
| caccaacctc | taacccatct | ctgacatttg | aaatatatag | ggtgcccttt | ggcaaagaaa | 360 |
| gaatagaagg | agtaattaag | gacttcgttt | tgacatggct | ggaaaataga | ccatctcctt | 420 |
| caaccatttg | gagattctat | caggagatgg | ccaaagtaat | caaggacttc | acatggtgt | 480 |
| ctcaggagat | ctgtgatggc | gttcttaaaa | accaacagct | gatggcaaag | ctaaagaaaa | 540 |
| gcaagtttga | agtcctggtg | tctgatccag | tatttccttg | tggcgatata | gtagctttaa | 600 |
| aacttggaat | tccatttatg | tactccttga | ggttttctcc | agcctcaaca | gtggaaaagc | 660 |
| actgtgggaa | ggtaccatac | cctccttcct | atgttcctgc | tgttttatca | gaactcaccg | 720 |
| accaaatgtc | tttcactgac | agaataagaa | atttcatctc | ctaccaccta | caggactaca | 780 |
| tgtttgaaac | tctttggaaa | tcatgggatt | catactatag | taaagcttta | gatggtagcc | 840 |
| attggttaaa | tattaagatt | attctagaag | agttgattca | aagaaatcac | aatgtgactg | 900 |
| tactggcttc | atcagcaact | ctattcatca | actccaatcc | cgattctcct | gtgaattttg | 960 |
| aagtgatacc | tgtttcctac | aagaagagca | atatagattc | cttaattgag | catatgaataa | 1020 |
| tgctgtggat | tgaccataga | ccaactcctc | tcacaatatg | ggctttctac | aaagaactag | 1080 |
| gaaaacttct | agacactttc | tttcaaatta | acatacaact | ctgtgatggt | gtactaaaga | 1140 |
| acccaaagtt | gatggcaaga | cttcagaaag | gtggttttga | tgtgttggta | gcagacccag | 1200 |
| taacaatctg | tggtgatctt | gttgctctga | aattaggaat | tccatttatg | tacacattga | 1260 |
| ggttctctcc | agcatcaaca | gtggagagac | actgtgggaa | aatcccagca | ccagtctcct | 1320 |
| atgtaccggc | agccttatca | gagctcactg | accagatgac | ctttggtgaa | aggattaaaa | 1380 |
| ataccatatc | ttattctctg | caagactata | tatttcagtc | ctactgggga | gaatggaatt | 1440 |
| catactatag | caaaattta | ggaagaccca | ctacgttatg | tgagactatg | ggaaagctg | 1500 |
| aaatttggtt | aatccgaaca | tattgggatt | ttgaatttcc | tcgtccatac | ttacctaatt | 1560 |
| ttgagtttgt | tggaggattg | cactgcaaac | ctgccaaacc | tttacctaag | gttttatgga | 1620 |
| gatacaaagg | aaagaaacca | gccacattag | gaaacaatac | tcagctcttt | gattggatac | 1680 |
| cccagaatga | tcttcttgga | catcccaaaa | ccaaagcttt | tatcactcat | ggtggaacta | 1740 |
| atgggatcta | cgaagctatt | taccacggag | tccctatggt | gggagttccc | atgtttgctg | 1800 |
| atcagcctga | taacattgct | cacatgaagg | ccaaaggagc | agctgtggaa | gtgaacctaa | 1860 |

```
acacaatgac aagtgtggat ttgcttagcg ctttgagaac agtcattaat gaaccttctt    1920
ataaagagaa tgctatgagg ttatcaagaa ttcaccatga tcaacctgta aagcccctgg    1980
atcgagcagt cttctggatc gagtttgtca tgcgccacaa aggagccaag caccttcggg    2040
ttgcagccca tgacctcacc tggttccagt accactcttt ggatgtaatt gggttcttgc    2100
tggtctgtgt gacaacggct atattttggg tcatacaatg ttgtttgttt tcctgtcaaa    2160
aatttggtaa gataggaaag aagaaaaaaa gagaataggt caagaaaaag aggaaatata    2220
tatattttta agtttggcaa aatcctgagt agtgtagtcc tattaattcc agacaaaagg    2280
agtttaacaa aaacacgtct cccatcctgt ttccaaattt tctatttctc tacctgcgat    2340
aagcctactg ataaagccta gattttggca tgattattat taacttgtga gttatagtct    2400
tctatttttc ctttgtctct ccctgctgac tatacccctct tcctgtcact tttctgacac    2460
aaggatacta cctaatttta aatatgttct attcatagta tcaaattatt ttatcgttaa    2520
ccttaattaa tgattaacaa tatgctgaat cctggtaatg catacagtgt agatggaatt    2580
tgataggtgt aaggaagagt caaattcaca aatttccata taccaaacaa atcagggagc    2640
caccgtagga gagtagtgtg ttatgagaaa ggtaatgatt tccttttta ataaaaacaa    2700 actcttctgc ttgctcaatg tttcaggagt tagagaatga attttaagtg tgacgtgcgt    2760
ccctattaaa tgtctacaaa attttcatta agcatatcta gaaaatcacg gcataacttg    2820 cctgccttc ttcaacatat attcttatat aacctgtagt ggaagatttg ggtactgtct    2880
ttaataaatc aatcaatcga ctctttttatt tcaaggagaa agttctatgt tatatgttga    2940
aggtgaacag atcatattta gaggatataa caattagaaa tctagaaaat aattatcatt    3000
tttataaaat tttagtcaa ctgtacaaat aattacataa acatcaatt aattatgctt    3060 aaaaatcact aatgttcata atatataatc actatttgta atcaaagtt taattttatg    3120 ccaaaaaata aaaatgctt acttggaatt tgaa                                3154
```

<210> SEQ ID NO 28
<211> LENGTH: 693
<212> TYPE: PRT
<213> ORGANISM: Homo sapiens

<400> SEQUENCE: 28

```
Met Leu Asn Asn Leu Leu Phe Ser Leu Gln Ile Ser Leu Ile Gly
1               5                   10                  15

Thr Thr Leu Gly Gly Asn Val Leu Ile Trp Pro Met Glu Gly Ser His
            20                  25                  30

Trp Leu Asn Val Lys Ile Ile Ile Asp Glu Leu Ile Lys Lys Glu His
        35                  40                  45

Asn Val Thr Val Leu Val Ala Ser Gly Ala Leu Phe Ile Thr Pro Thr
    50                  55                  60

Ser Asn Pro Ser Leu Thr Phe Glu Ile Tyr Arg Val Pro Phe Gly Lys
65                  70                  75                  80

Glu Arg Ile Glu Gly Val Ile Lys Asp Phe Val Leu Thr Trp Leu Glu
                85                  90                  95

Asn Arg Pro Ser Pro Ser Thr Ile Trp Arg Phe Tyr Gln Glu Met Ala
            100                 105                 110

Lys Val Ile Lys Asp Phe His Met Val Ser Gln Glu Ile Cys Asp Gly
        115                 120                 125

Val Leu Lys Asn Gln Gln Leu Met Ala Lys Leu Lys Lys Ser Lys Phe
    130                 135                 140
```

```
Glu Val Leu Val Ser Asp Pro Val Phe Pro Cys Gly Asp Ile Val Ala
145                 150                 155                 160

Leu Lys Leu Gly Ile Pro Phe Met Tyr Ser Leu Arg Phe Ser Pro Ala
            165                 170                 175

Ser Thr Val Glu Lys His Cys Gly Lys Val Pro Tyr Pro Pro Ser Tyr
        180                 185                 190

Val Pro Ala Val Leu Ser Glu Leu Thr Asp Gln Met Ser Phe Thr Asp
        195                 200                 205

Arg Ile Arg Asn Phe Ile Ser Tyr His Leu Gln Asp Tyr Met Phe Glu
        210                 215                 220

Thr Leu Trp Lys Ser Trp Asp Ser Tyr Tyr Ser Lys Ala Leu Asp Gly
225                 230                 235                 240

Ser His Trp Leu Asn Ile Lys Ile Ile Leu Glu Glu Leu Ile Gln Arg
                245                 250                 255

Asn His Asn Val Thr Val Leu Ala Ser Ser Ala Thr Leu Phe Ile Asn
            260                 265                 270

Ser Asn Pro Asp Ser Pro Val Asn Phe Glu Val Ile Pro Val Ser Tyr
        275                 280                 285

Lys Lys Ser Asn Ile Asp Ser Leu Ile Glu His Met Ile Met Leu Trp
        290                 295                 300

Ile Asp His Arg Pro Thr Pro Leu Thr Ile Trp Ala Phe Tyr Lys Glu
305                 310                 315                 320

Leu Gly Lys Leu Leu Asp Thr Phe Phe Gln Ile Asn Ile Gln Leu Cys
                325                 330                 335

Asp Gly Val Leu Lys Asn Pro Lys Leu Met Ala Arg Leu Gln Lys Gly
            340                 345                 350

Gly Phe Asp Val Leu Val Ala Asp Pro Val Thr Ile Cys Gly Asp Leu
        355                 360                 365

Val Ala Leu Lys Leu Gly Ile Pro Phe Met Tyr Thr Leu Arg Phe Ser
        370                 375                 380

Pro Ala Ser Thr Val Glu Arg His Cys Gly Lys Ile Pro Ala Pro Val
385                 390                 395                 400

Ser Tyr Val Pro Ala Ala Leu Ser Glu Leu Thr Asp Gln Met Thr Phe
                405                 410                 415

Gly Glu Arg Ile Lys Asn Thr Ile Ser Tyr Ser Leu Gln Asp Tyr Ile
            420                 425                 430

Phe Gln Ser Tyr Trp Gly Glu Trp Asn Ser Tyr Tyr Ser Lys Ile Leu
        435                 440                 445

Gly Arg Pro Thr Thr Leu Cys Glu Thr Met Gly Lys Ala Glu Ile Trp
        450                 455                 460

Leu Ile Arg Thr Tyr Trp Asp Phe Glu Phe Pro Arg Pro Tyr Leu Pro
465                 470                 475                 480

Asn Phe Glu Phe Val Gly Gly Leu His Cys Lys Pro Ala Lys Pro Leu
                485                 490                 495

Pro Lys Val Leu Trp Arg Tyr Lys Gly Lys Lys Pro Ala Thr Leu Gly
            500                 505                 510

Asn Asn Thr Gln Leu Phe Asp Trp Ile Pro Gln Asn Asp Leu Leu Gly
        515                 520                 525

His Pro Lys Thr Lys Ala Phe Ile Thr His Gly Gly Thr Asn Gly Ile
        530                 535                 540

Tyr Glu Ala Ile Tyr His Gly Val Pro Met Val Gly Val Pro Met Phe
545                 550                 555                 560
```

-continued

```
Ala Asp Gln Pro Asp Asn Ile Ala His Met Lys Ala Lys Gly Ala Ala
            565                 570                 575

Val Glu Val Asn Leu Asn Thr Met Thr Ser Val Asp Leu Leu Ser Ala
        580                 585                 590

Leu Arg Thr Val Ile Asn Glu Pro Ser Tyr Lys Glu Asn Ala Met Arg
    595                 600                 605

Leu Ser Arg Ile His His Asp Gln Pro Val Lys Pro Leu Asp Arg Ala
610                 615                 620

Val Phe Trp Ile Glu Phe Val Met Arg His Lys Gly Ala Lys His Leu
625                 630                 635                 640

Arg Val Ala Ala His Asp Leu Thr Trp Phe Gln Tyr His Ser Leu Asp
                645                 650                 655

Val Ile Gly Phe Leu Leu Val Cys Val Thr Thr Ala Ile Phe Leu Val
            660                 665                 670

Ile Gln Cys Cys Leu Phe Ser Cys Gln Lys Phe Gly Lys Ile Gly Lys
        675                 680                 685

Lys Lys Lys Arg Glu
    690
```

```
<210> SEQ ID NO 29
<211> LENGTH: 2656
<212> TYPE: DNA
<213> ORGANISM: Homo sapiens

<400> SEQUENCE: 29
```

| | | | | |
|---|---|---|---|---|
| ttacattcgg | cttcttccta | atgtcaaatg | agtgctgtta | aagttcctcc aggaaacttc | 60 |
| agcagagaaa | acatttgct | tcacatctca | tcaaatcttc | tgcatcaagc cacatcatgt | 120 |
| taaacaacct | tctgctgttc | tcccttcaga | taagtctcat | aggaaccact cttggtggga | 180 |
| atgttttgat | ttggccaatg | gaaggtagtc | attggctaaa | tgttaagata attatagatg | 240 |
| agctcattaa | aaaggagcat | aatgtgactg | tcctagttgc | ctctggtgca cttttcatca | 300 |
| caccaacctc | taacccatct | ctgacatttg | aaatatatag | ggtgcccttt ggcaaagaaa | 360 |
| gaatagaagg | agtaattaag | gacttcgttt | tgacatggct | ggaaaataga ccatctcctt | 420 |
| caaccatttg | gagattctat | caggagatgg | ccaaagtaat | caaggacttc acatggtgt | 480 |
| ctcaggagat | ctgtgatggc | gttcttaaaa | accaacagct | gatggcaaag ctaaagaaaa | 540 |
| gcaagtttga | agtcctggtg | tctgatccag | tatttccttg | tggcgatata gtagctttaa | 600 |
| aacttggaat | tccatttatg | tactccttga | ggttttctcc | agcctcaaca gtggaaaagc | 660 |
| actgtgggaa | ggtaccatac | cctccttcct | atgttcctgc | tgttttatca gaactcaccg | 720 |
| accaaatgtc | tttcactgac | agaataagaa | atttcatctc | ctaccaccta caggactaca | 780 |
| tgtttgaaac | tctttggaaa | tcatgggatt | catactatag | taaagcttta ggtggactct | 840 |
| tactctgttg | cccaggctgg | agtgcagtgg | cggatcttgg | ctcactgcaa cctctgcttc | 900 |
| ccgggttcaa | gcgattctcc | cgcctcagcc | tccattgtag | ttgggattac aggctgccag | 960 |
| caggaagacc | cactacgtta | tgtgagacta | tggggaaagc | tgaaatttgg ttaatccgaa | 1020 |
| catattggga | ttttgaattt | cctcgtccat | acttacctaa | ttttgagttt gttggaggat | 1080 |
| tgcactgcaa | acctgccaaa | cctttaccta | aggttttatg | gagatacaaa ggaagagaac | 1140 |
| cagccacatt | aggaaacaat | actcagctct | tgattggat | accccagaat gatcttcttg | 1200 |
| gacatcccca | aaccaaagct | tttatcactc | atggtggaac | taatgggatc tacgaagcta | 1260 |
| tttaccacgg | agtccctatg | gtgggagttc | ccatgttttg | tgatcagcct gataacattg | 1320 |

-continued

| | |
|---|---|
| ctcacatgaa ggccaaagga gcagctgtgg aagtgaacct aaacacaatg acaagtgtgg | 1380 |
| atttgcttag cgctttgaga acagtcatta atgaaccttc ttataaagag aatgctatga | 1440 |
| ggttatcaag aattcaccat gatcaacctg taaagcccct ggatcgagca gtcttctgga | 1500 |
| tcgagtttgt catgcgccac aaaggagcca agcaccttcg ggttgcagcc catgacctca | 1560 |
| cctggttcca gtaccactct ttggatgtaa ttgggttctt gctggtctgt gtgacaacgg | 1620 |
| ctatattttt ggtcatacaa tgttgtttgt tttcctgtca aaatttggt aagataggaa | 1680 |
| agaagaaaaa aagagaatag gtcaagaaaa agaggaaata tatatatttt taagtttggc | 1740 |
| aaaatcctga gtagtgtagt cctattaatt ccagacaaaa ggagtttaac aaaaacacgt | 1800 |
| ctcccatcct gtttccaaat tttctatttc tctacctgcg ataagcctac tgataaagcc | 1860 |
| tagattttgg catgattatt attaacttgt gagttatagt cttctatttt tcctttgtct | 1920 |
| ctccctgctg actataccct cttcctgtca cttttctgac acaaggatac tacctaattt | 1980 |
| taaatatgtt ctattcatag tatcaaatta ttttatcgtt aaccttaatt aatgattaac | 2040 |
| aatatgctga atcctggtaa tgcatacagt gtagatggaa tttgataggt gtaaggaaga | 2100 |
| gtcaaattca caaatttcca tataccaaac aaatcaggga gccaccgtag agagtagtg | 2160 |
| tgttatgaga aaggtaatga tttccttttt taataaaaac aaactcttct gcttgctcaa | 2220 |
| tgtttcagga gttagagaat gaattttaag tgtgacgtgc gtccctatta aatgtctaca | 2280 |
| aaattttcat taagcatatc tagaaaatca cggcataact tgcctgcctt tcttcaacat | 2340 |
| atattcttat ataacctgta gtggaagatt tgggtactgt ctttaataaa tcaatcaatc | 2400 |
| gactctttta tttcaaggag aaagttctat gttatatgtt gaaggtgaac agatcatatt | 2460 |
| tagaggatat aacaattaga aatctagaaa ataattatca tttttataaa atttttagtc | 2520 |
| aactgtacaa ataattacat aaaacatcaa ttaattatgc ttaaaaatca ctaatgttca | 2580 |
| taatatataa tcactatttg taatcaaaag tttaattta tgccaaaaaa taaaaatgc | 2640 |
| ttacttggaa tttgaa | 2656 |

<210> SEQ ID NO 30
<211> LENGTH: 527
<212> TYPE: PRT
<213> ORGANISM: Homo sapiens

<400> SEQUENCE: 30

Met Leu Asn Asn Leu Leu Leu Phe Ser Leu Gln Ile Ser Leu Ile Gly
1               5                   10                  15

Thr Thr Leu Gly Gly Asn Val Leu Ile Trp Pro Met Glu Gly Ser His
            20                  25                  30

Trp Leu Asn Val Lys Ile Ile Ile Asp Glu Leu Ile Lys Lys Glu His
        35                  40                  45

Asn Val Thr Val Leu Val Ala Ser Gly Ala Leu Phe Ile Thr Pro Thr
    50                  55                  60

Ser Asn Pro Ser Leu Thr Phe Glu Ile Tyr Arg Val Pro Phe Gly Lys
65                  70                  75                  80

Glu Arg Ile Glu Gly Val Ile Lys Asp Phe Val Leu Thr Trp Leu Glu
                85                  90                  95

Asn Arg Pro Ser Pro Ser Thr Ile Trp Arg Phe Tyr Gln Glu Met Ala
            100                 105                 110

-continued

```
Lys Val Ile Lys Asp Phe His Met Val Ser Gln Glu Ile Cys Asp Gly
            115                 120                 125
Val Leu Lys Asn Gln Gln Leu Met Ala Lys Leu Lys Lys Ser Lys Phe
130                 135                 140
Glu Val Leu Val Ser Asp Pro Val Phe Pro Cys Gly Asp Ile Val Ala
145                 150                 155                 160
Leu Lys Leu Gly Ile Pro Phe Met Tyr Ser Leu Arg Phe Ser Pro Ala
                165                 170                 175
Ser Thr Val Glu Lys His Cys Gly Lys Val Pro Tyr Pro Pro Ser Tyr
            180                 185                 190
Val Pro Ala Val Leu Ser Glu Leu Thr Asp Gln Met Ser Phe Thr Asp
            195                 200                 205
Arg Ile Arg Asn Phe Ile Ser Tyr His Leu Gln Asp Tyr Met Phe Glu
            210                 215                 220
Thr Leu Trp Lys Ser Trp Asp Ser Tyr Tyr Ser Lys Ala Leu Gly Gly
225                 230                 235                 240
Leu Leu Leu Cys Cys Pro Gly Trp Ser Ala Val Ala Asp Leu Gly Ser
                245                 250                 255
Leu Gln Pro Leu Leu Pro Gly Phe Lys Arg Phe Ser Arg Leu Ser Leu
            260                 265                 270
His Cys Ser Trp Asp Tyr Arg Leu Pro Ala Gly Arg Pro Thr Thr Leu
            275                 280                 285
Cys Glu Thr Met Gly Lys Ala Glu Ile Trp Leu Ile Arg Thr Tyr Trp
            290                 295                 300
Asp Phe Glu Phe Pro Arg Pro Tyr Leu Pro Asn Phe Glu Phe Val Gly
305                 310                 315                 320
Gly Leu His Cys Lys Pro Ala Lys Pro Leu Pro Lys Val Leu Trp Arg
                325                 330                 335
Tyr Lys Gly Lys Lys Pro Ala Thr Leu Gly Asn Asn Thr Gln Leu Phe
            340                 345                 350
Asp Trp Ile Pro Gln Asn Asp Leu Leu Gly His Pro Lys Thr Lys Ala
            355                 360                 365
Phe Ile Thr His Gly Gly Thr Asn Gly Ile Tyr Glu Ala Ile Tyr His
            370                 375                 380
Gly Val Pro Met Val Gly Val Pro Met Phe Ala Asp Gln Pro Asp Asn
385                 390                 395                 400
Ile Ala His Met Lys Ala Lys Gly Ala Ala Val Glu Val Asn Leu Asn
                405                 410                 415
Thr Met Thr Ser Val Asp Leu Leu Ser Ala Leu Arg Thr Val Ile Asn
            420                 425                 430
Glu Pro Ser Tyr Lys Glu Asn Ala Met Arg Leu Ser Arg Ile His His
            435                 440                 445
Asp Gln Pro Val Lys Pro Leu Asp Arg Ala Val Phe Trp Ile Glu Phe
            450                 455                 460
Val Met Arg His Lys Gly Ala Lys His Leu Arg Val Ala Ala His Asp
465                 470                 475                 480
Leu Thr Trp Phe Gln Tyr His Ser Leu Asp Val Ile Gly Phe Leu Leu
                485                 490                 495
Val Cys Val Thr Thr Ala Ile Phe Leu Val Ile Gln Cys Cys Leu Phe
            500                 505                 510
Ser Cys Gln Lys Phe Gly Lys Ile Gly Lys Lys Lys Arg Glu
            515                 520                 525
```

```
<210> SEQ ID NO 31
<211> LENGTH: 22
<212> TYPE: DNA
<213> ORGANISM: Artificial Sequence
<220> FEATURE:
<223> OTHER INFORMATION: MET specific primer 1

<400> SEQUENCE: 31
gctggtggtc ctaccataca tg                                                22

<210> SEQ ID NO 32
<211> LENGTH: 22
<212> TYPE: DNA
<213> ORGANISM: Artificial Sequence
<220> FEATURE:
<223> OTHER INFORMATION: MET specific primer 2

<400> SEQUENCE: 32
ctggcttaca gctagtttgc ca                                                22
```

GENE EXPRESSION SIGNATURES PREDICTIVE OF SUBJECT RESPONSE TO A MULTI-KINASE INHIBITOR AND METHODS OF USING THE SAME

CROSS-REFERENCE TO RELATED APPLICATIONS

The present application is a National Stage Entry of International Patent Application No. PCT/US2014/053142, filed Aug. 28, 2014, which claims priority to, and the benefit of International Patent Application Serial No. PCT/CN2013/082487, filed Aug. 28, 2013, each of which is herein incorporated by reference in its entirety for all purposes.

FIELD OF THE INVENTION

The present invention relates to treatment of subjects as well as identification and selection of subjects for treatment with a multi-kinase inhibitor, e.g., Sorafenib, Sunitinib, Axitinib, Vandetanib, Pazopanib, Cabozantinib, etc. or a salt, solvate, or physiologically functional derivative thereof, or a mixture thereof. Provided are methods, reagents, and tools for the prediction, diagnosis, prognosis, and therapy of a disease such as cancer.

DESCRIPTION OF THE TEXT FILE SUBMITTED ELECTRONICALLY

The content of the text file submitted electronically herewith is incorporated herein by reference in its entirety: A computer readable format copy of the Sequence Listing (filename: CRBI-005-01US_ST25.txt; date recorded: Feb. 25, 2016; file size 140 KB).

BACKGROUND OF THE INVENTION

Hepatocellular carcinoma (HCC) is an aggressive tumor and the fifth deadliest cancers worldwide. It is particularly prevalent in East Asia and in man (Parkin D M, Bray F, Ferlay J, Pisani P. Global cancer statistics, 2002. CA Cancer J Clin 2005; 55:74-108. El-Serag H B, 7. Rudolph K L. Hepatocellular carcinoma: epidemiology and molecular carcinogenesis. Gastroenterology 2007; 132:2557-76). Its incidence is increasing steadily in both the United States and China (1). So far, there have been few effective treatment options. The common standard chemotherapy (e.g. doxorubicin) has little clinical benefit.

The only approved target therapy available is Sorafenib that recently became available (1). Sorafenib is a multi-kinase inhibitor targeting vascular endothelial growth factor (VEGF)-mediated angiogenesis and blocking the RAF/extracellular signal regulated kinase (ERK) kinase (MEK)/ERK cascade. It is the first drug found to prolong survival of patients with advanced hepatocellular carcinoma (HCC), and has been marketed for treatment of advanced renal cell carcinoma and unresectable HCC. However, increase survival for HCC patients is by modest 3 months. Like many new generation target therapies, Sorafenib also has unfavorable side effects. Many HCC patients do not respond well to Sorafenib both in term of safety and lack of efficacy. There is a clear need for predictive markers of Sorafenib to help selecting the patient population that may benefit the most.

It was reported that the baseline level of phosphorylated ERK (pERK) might be a relevant marker from the initial single arm phase II study of Sorafenib, and a few reports have been published on relationship between the serum markers (e.g. soluble c-KIT, HGF, AFP, VEGF, etc) and the outcome of Sorafenib treatment, but these results are either very preliminary or not consistent across studies. Thus, the utility of these factors as potential predictive markers need to be further evaluated, and new strategies like genomic-based molecular signature analysis could be useful to identify new predictive markers, and help us better understand the mechanism of action of Sorafenib in HCC.

SUMMARY OF THE INVENTION

The present invention provides a panel of gene markers that can be used to predict a subject's responsiveness/resistance to a drug. In some embodiments, the gene markers include SEC14L2, H6PD, TMEM140, SLC2A5, ACTA1, IRF8, STAT2, UGT2A1, functional variants, fragments, or orthologs thereof.

The present invention also provides a collection of activity profile of a panel of gene markers comprising at least two or more gene markers selected from the group consisting of SEC14L2, H6PD, TMEM140, SLC2A5, ACTA1, IRF8, STAT2, UGT2A1, functional variants, fragments, or orthologs thereof. In some embodiments, the activity profile is collected from more than one subject that is responding to a drug. In some embodiments, the activity profile is collected from more than one subject that is resistant to a drug. In some embodiments, the drug is a multi-kinase inhibitor. In some embodiments, the multi-kinase inhibitor targets to vascular endothelial growth factor (VEGF)-mediated angiogenesis and blocks the RAF/extracellular signal regulated kinase (ERK) kinase (MEK)/ERK cascade. In some embodiments, the multi-kinase inhibitor comprises Sorafenib, or a salt, solvate, or physiologically functional derivative thereof. In some embodiments, the collection of activity profile is collected from the subjects, parts of the subjects, or cells derived from the subjects before, during and/or after being treated with the drug. In some embodiments, the panel of gene markers includes at least two, three, or four of gene markers of the present invention.

The present invention also provides methods for determining a subject's responsiveness or resistance to a drug. In some embodiments, the drug is a multi-kinase inhibitor. In some embodiments, the multi-kinase inhibitor targets to vascular endothelial growth factor (VEGF)-mediated angiogenesis and blocks the RAF/extracellular signal regulated kinase (ERK) kinase (MEK)/ERK cascade. In some embodiments, the multi-kinase inhibitor comprises Sorafenib, or a salt, solvate, or physiologically functional derivative thereof. In some embodiments, the methods comprise measuring activity profile of a panel of gene markers. In some embodiments, the methods further comprise comparing the activity profile of the panel to a predetermined activity profile. In some embodiments, the subject's responsiveness is determined based on the comparison between the activity profile of the panel of gene markers and the predetermined activity profile. In some embodiments, the subject is determined to be responsive to the drug if the activity profile of the panel is within the predetermined activity profile, or determined to be resistant to the drug if the activity profile of the panel is not within the predetermined activity profile. In some embodiments, activity profile derived from subjects that are not responsive to the drug can also be used. For example, the subject is determined to be not responsive to the drug if the activity profile of the panel is within the activity profile derived from subjects that are not responsive to the drug.

In some embodiments, the activity profile of a panel of gene markers includes one or more parameters describing gene expression level, RNA activity level, and/or protein activity level. In some embodiments, the activity profile is reflected by a quantitative signature value or a set of signature values that are calculated on the basis of gene expression level, RNA activity level, and/or protein activity level.

In some embodiments, the panel comprises at least two, three, or four of gene markers. In some embodiments, the gene markers include at least one or more markers selected from the group consisting of SEC14L2, H6PD, TMEM140, SLC2A5, ACTA1, IRF8, STAT2, and UGT2A1, or any combination thereof.

In some embodiments, the activity profile is gene expression level, wherein a similar or lower expression of one or more gene markers in comparison to the predetermined activity profile before the treatment of the multi-kinase inhibitor indicates the responsiveness of the subject, and a higher expression of one or more gene markers in comparison to the predetermined activity profile before the treatment of the multi-kinase inhibitor indicates the resistance of the subject.

Alternatively, a normalization or stabilization in the activity level of a biomarker of the present invention toward a predetermined standard level after the treatment indicates responsiveness of subject. In some embodiments, a normalization or stabilization of SEC14L2, H6PD, TMEM140, SLC2A5, ACTA1, IRF8, STAT2, and/or UGT2A1 toward a predetermined standard level indicates the responsiveness of the subject. In some embodiments, an absence of normalization and stabilization of SEC14L2, H6PD, TMEM140, SLC2A5, ACTA1, IRF8, STAT2, and/or UGT2A1 toward a predetermined standard level indicates the resistance of the subject to the treatment. As used herein, when the level of a biomarker goes toward the predetermined standard level, it is called normalization. As used herein, when the level of a biomarker reduces its speed of going away from the predetermined standard level, it is called stabilization.

In some embodiments, the multi-kinase inhibitor is Sorafenib, Axitinib, Vandetanib, Pazopanib, Cabozantinib, or any combination thereof.

In some embodiments, the subject is a human with cancer. In some embodiments, the cancer is hepatocellular carcinoma.

The present invention also provides methods for administering a drug to a subject. In some embodiments, the drug is a multi-kinase inhibitor. In some embodiments, the methods comprise testing the subject for activity profile of a panel of gene markers. In some embodiments, the panel of gene markers includes at least one or more markers selected from the group consisting of SEC14L2, H6PD, TMEM140, SLC2A5, ACTA1, IRF8, STAT2, and UGT2A1. In some embodiments, the methods further comprise comparing the activity profile of the panel to a predetermined activity profile. In some embodiments, the comparison is conducted before, during, or after administration of the drug. In some embodiments, the drug comprises at least one multi-kinase inhibitor. In some embodiments, the multi-kinase inhibitor targets to vascular endothelial growth factor (VEGF)-mediated angiogenesis and blocks the RAF/extracellular signal regulated kinase (ERK) kinase (MEK)/ERK cascade. In some embodiments, the multi-kinase inhibitor is administered to the subject if the activity profile of the panel is within the predetermined activity profile derived from a population of subjects that are responding to the drug.

The present invention also provides an array comprising probes for detection of at least two or more gene markers. In some embodiments, the gene markers are selected from the group consisting of SEC14L2, H6PD, TMEM140, SLC2A5, ACTA1, IRF8, STAT2, and UGT2A1. In some embodiments, the array is a microarray.

BRIEF DESCRIPTION OF THE DRAWINGS

FIG. 1A: $\Delta T/\Delta C$ was calculated, where $\Delta T$ and $\Delta C$ were the mean tumor volume changes of the treated and control groups, respectively on a given day, as indicated by arrows in FIGS. B-E. *:$p<0.05$; :$p<0.01$; *:$p<0.001$. FIGS. 1B to 1E show representative HCC-HuPrime® respond to Sorafenib, model codes 001, 006, 020, and 021, respectively.

DETAILED DESCRIPTION OF THE INVENTION

Figure 1A:
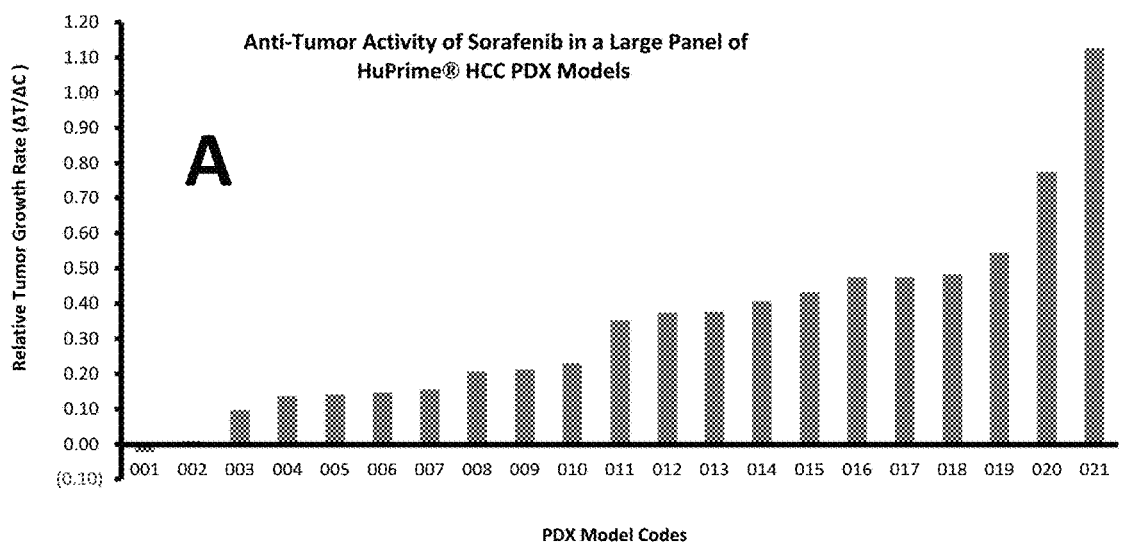
FIGS. 1A-1E show evaluation of efficacy of Sorafenib in a large panel of HuPrime HCC PDXs.
Figure 1B:
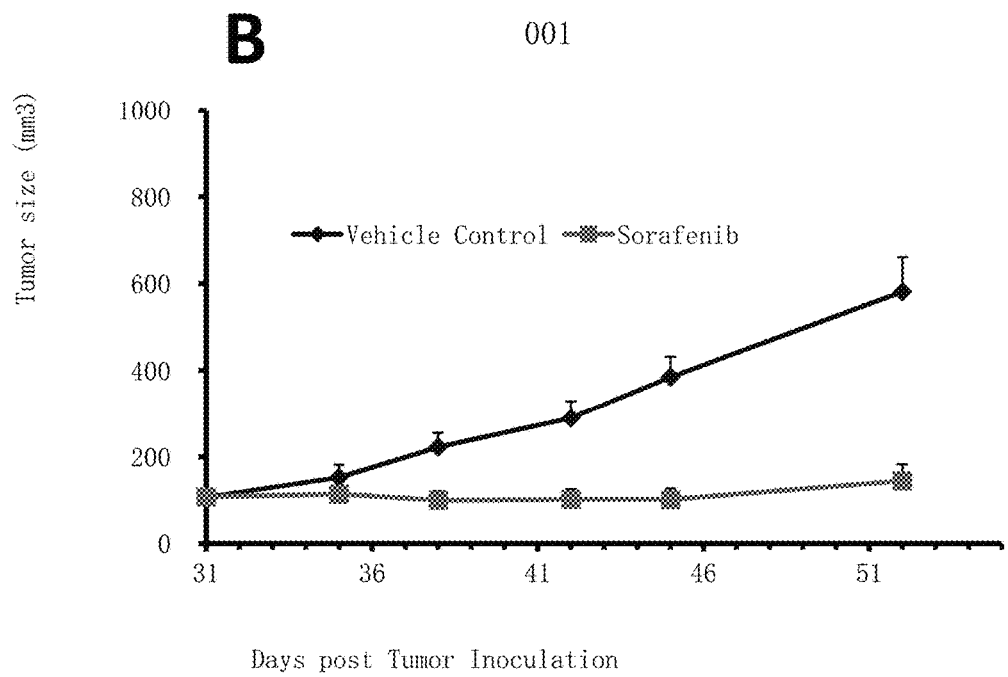
Figure 1C:
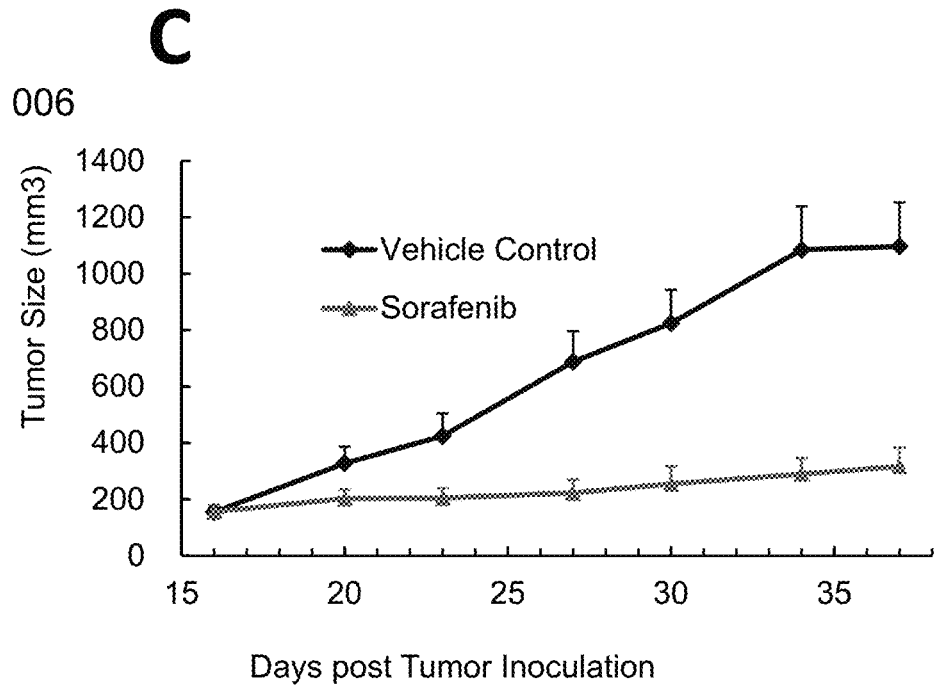
Figure 1D:
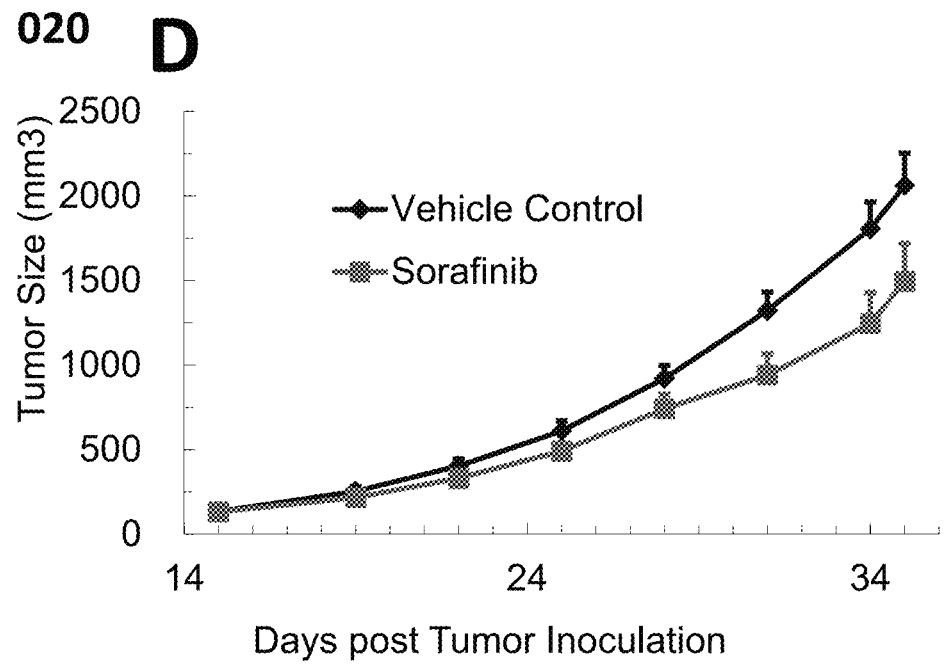
Figure 1E:
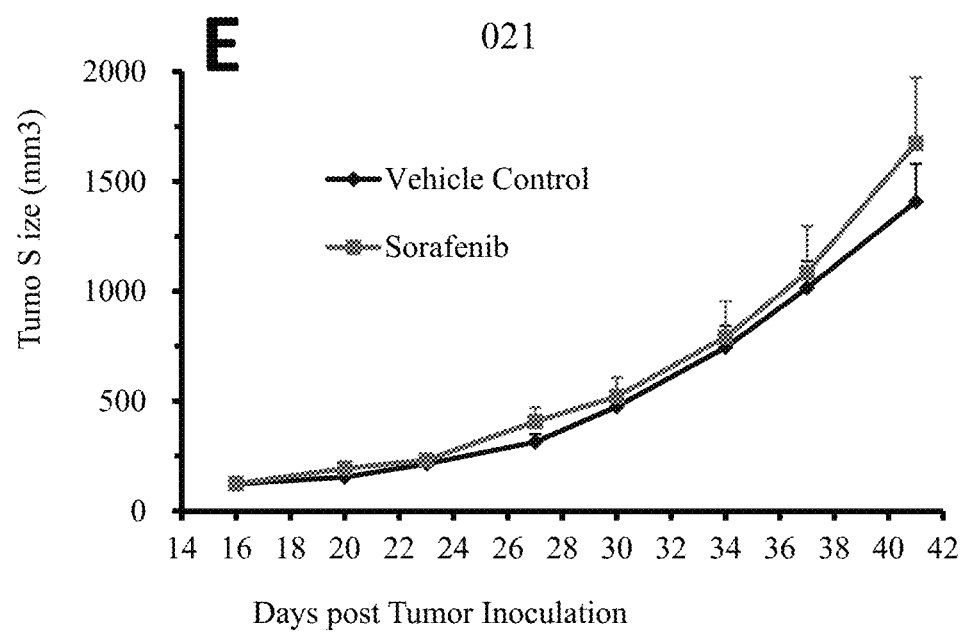
Figure 2:
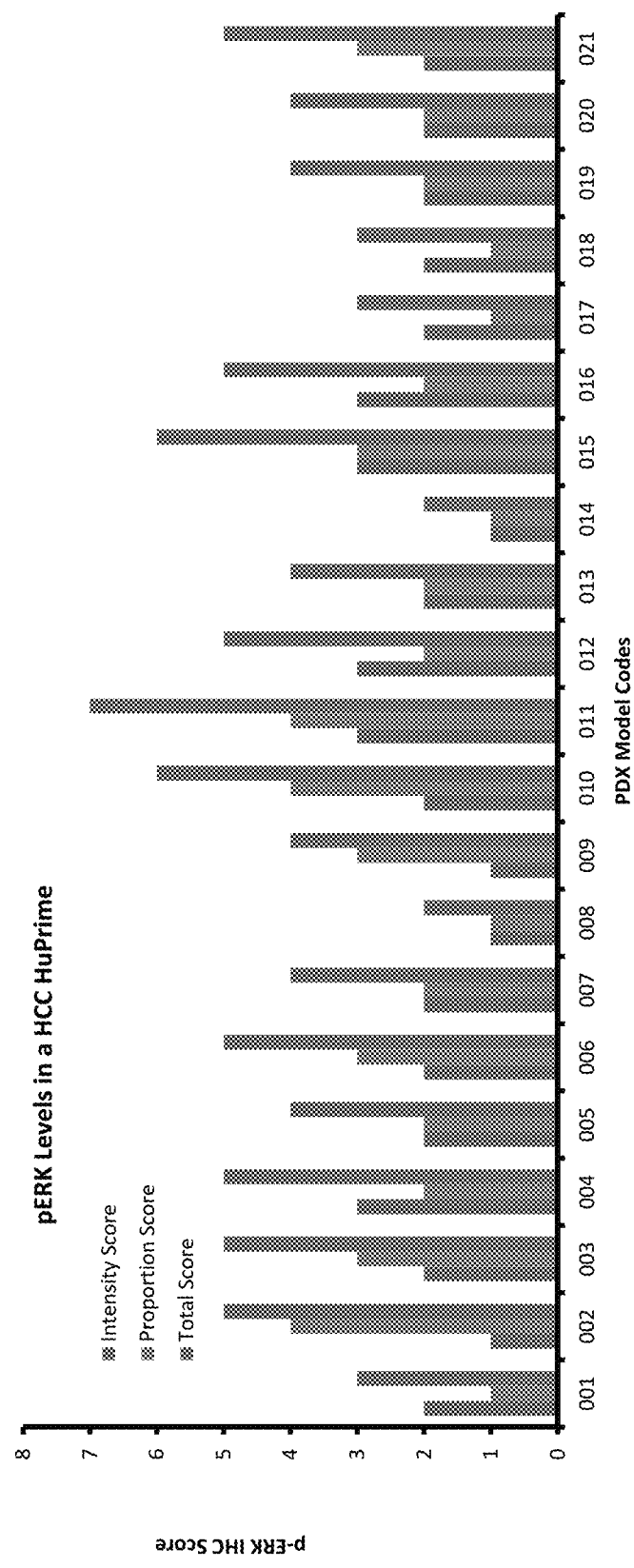
FIG. 2 shows baseline pERK level detected by IHC is not associated with the model response to Sorafenib.
Figure 3:
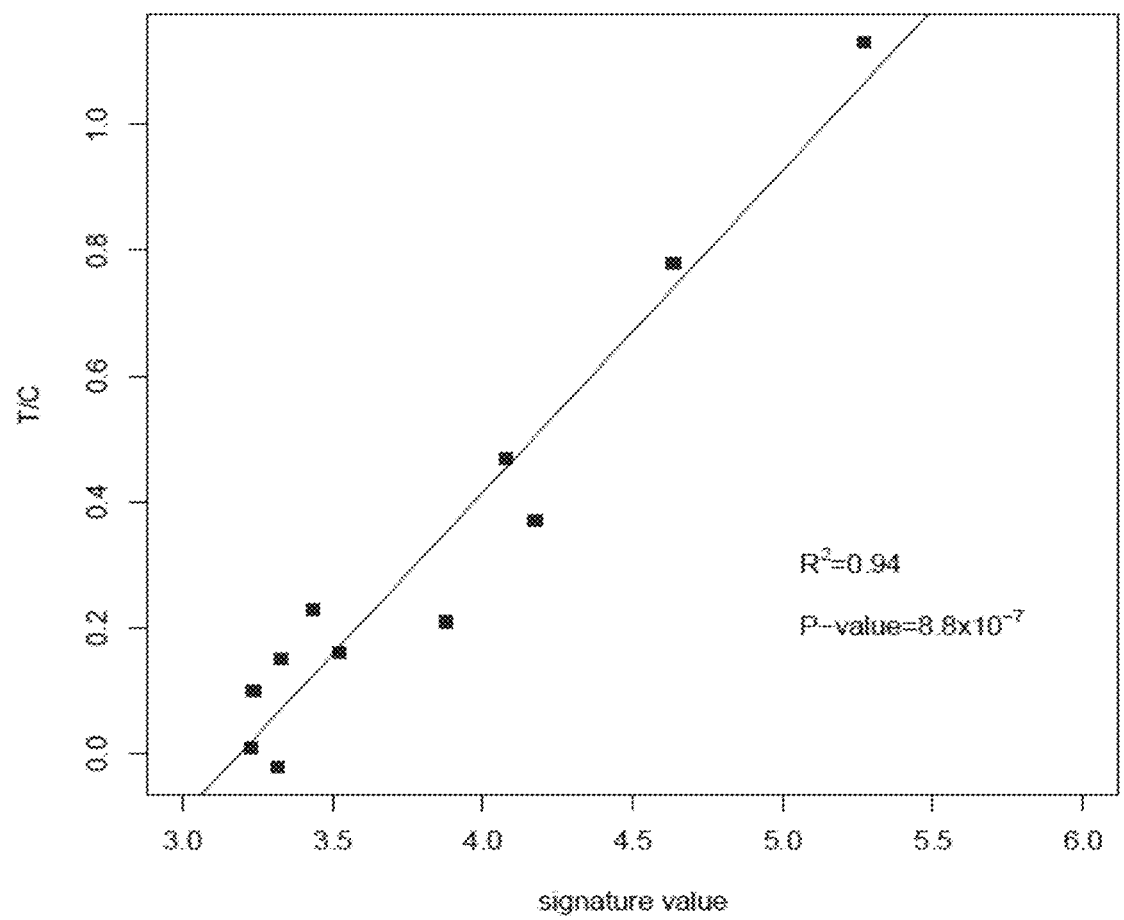
FIG. 3 shows Expression of signature genes is predictive of Sorafenib treatment effect to HCC in PDX models. The average mRNA expression intensity, in log 2-scale, of the marker genes, is designated as the signature score.

As used herein, the following terms shall have the following meanings:

The verb "comprise" as is used in this description and in the claims and its conjugations are used in its non-limiting sense to mean that items following the word are included, but items not specifically mentioned are not excluded.

The term "a" or "an" refers to one or more of that entity; for example, "a gene" refers to one or more genes or at least one gene. As such, the terms "a" (or "an"), "one or more" and "at least one" are used interchangeably herein. In addition, reference to "an element" by the indefinite article "a" or "an" does not exclude the possibility that more than one of the elements are present, unless the context clearly requires that there is one and only one of the elements.

The invention provides isolated, chimeric, recombinant or synthetic polynucleotide sequences. As used herein, the terms "polynucleotide", "polynucleotide sequence", "nucleic acid sequence", "nucleic acid fragment", and "isolated nucleic acid fragment" are used interchangeably herein and encompass DNA, RNA, cDNA, whether single stranded or double stranded, as well as chemical modifications thereof. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide. In some embodiments, the isolated, chimeric, recombinant or synthetic polynucleotide sequences are derived from gene markers of the present invention.

Single letter amino acid abbreviations used herein have their standard meaning in the art, and all peptide sequences described herein are written according to convention, with the N-terminal end to the left and the C-terminal end to the right.

The invention provides expression gene signatures that can be used to predict patient response to a drug. As used herein, the term "gene" refers to any segment of DNA associated with a biological function. Thus, genes include, but are not limited to, coding sequences and/or the regulatory sequences required for their expression. Genes can also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

The invention provides homologous and orthologous polynucleotides and polypeptides. As used herein, the term "homologous" or "homologue" or "ortholog" is known in the art and refers to related sequences that share a common ancestor or family member and are determined based on the degree of sequence identity. The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences. These terms describe the relationship between a gene found in one species, subspecies, variety, cultivar or strain and the corresponding or equivalent gene in another species, subspecies, variety, cultivar or strain. For purposes of this invention homologous sequences are compared. "Homologous sequences" or "homologues" or "orthologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. The degree of sequence identity may vary, but in some embodiments, is at least 50% (when using standard sequence alignment programs known in the art), at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%. Homology can be determined using software programs readily available in the art, such as those discussed in Current Protocols in Molecular Biology (F. M. Ausubel et al., eds., 1987) Supplement 30, section 7.718, Table 7.71. Some alignment programs are MacVector (Oxford Molecular Ltd, Oxford, U.K.), ALIGN Plus (Scientific and Educational Software, Pennsylvania) and AlignX (Vector NTI, Invitrogen, Carlsbad, Calif.). Another alignment program is Sequencher (Gene Codes, Ann Arbor, Mich.), using default parameters.

The invention provides probes and primers that are derived from the nucleic acid sequences of the signature genes. The term "probe" as used herein refers to an oligonucleotide which is capable of specific annealing to the amplification target. The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (NT vs. G/C content) of primer. A pair of bi-directional primers consists of one forward and one reverse primer as commonly used in the art of DNA amplification such as in PCR amplification. In some embodiments, the primers or probes hybridize with any of SEQ ID NOs. 1, 3, 5, 7, 9, 11, 13, 15, 17, 19, 21, 23, 25, 27, and 29. In some embodiments, the primers or probes hybridize with any of SEQ ID NOs. 1, 3, 5, 7, 9, 11, 13, 15, 17, 19, 21, 23, 25, 27, and 29 under stringent hybridization conditions. As used herein, stringent hybridization conditions can be 6×SSC (0.9 M NaCl, 0.09 M sodium citrate, pH 7.4) at 65° C.

The terms "array" or "matrix" refer to an arrangement of addressable locations or "addresses" on a device. The locations can be arranged in two-dimensional arrays, three-dimensional arrays, or other matrix formats. The number of locations may range from several to at least hundreds of thousands. Most importantly, each location represents a totally independent reaction site. A "nucleic acid array" refers to an array containing nucleic acid probes, such as oligonucleotides or larger portions of genes. The nucleic acid on the array is preferably single-stranded. Arrays wherein the probes are oligonucleotides are referred to as "oligonucleotide arrays" or "oligonucleotide chips." A "microarray," also referred to herein as a "biochip" or "biological chip," is an array of regions having a density of discrete regions of at least about $100/cm^2$, and preferably at least about $1000/cm^2$. The regions in a microarray have typical dimensions, for example, diameters, in the range of between about 10-250 μm, and are separated from other regions in the array by about the same distance. None limiting examples of compositions and methods for making and using arrays are described in U.S. Pat. Nos. 5,202,231, 5,695,940, 5,525,464, 5,445,934, 5,744,305, 5,677,195, 5,800,992, 5,871,928, 5,795,716, 5,700,637, 6,054,270, 5,807,522, and 6,110,426, each of which is incorporated by reference herein in its entirety for all purposes.

The term "sample" or "biological sample" as used herein, refers to a sample obtained from an organism or from components (e.g., cells) of an organism. The sample may be of any biological tissue or fluid. The sample may be a sample which is derived from a patient. Such samples include, but are not limited to, sputum, blood, blood cells (e.g., white blood cells), tissue or biopsy samples (e.g., tumor biopsy), urine, peritoneal fluid, and pleural fluid, patient derived xenografts (PDXs), or cells therefrom. Biological samples may also include sections of tissues such as frozen sections taken for histological purposes.

The term "marker" encompasses a broad range of intra- and extra-cellular events as well as whole-organism physiological changes. A marker may be represent essentially any aspect of cell function, for example, but not limited to, levels or rate of production of signaling molecules, transcription factors, metabolites, gene transcripts as well as post-translational modifications of proteins. Marker may include partial and/or whole genome analysis of transcript levels, rates, and/or stability, and partial and/or whole proteome analysis of protein levels, activity and/or modifications. A signature may also refer to a gene or gene product which is up- or down-regulated in a compound-treated subject having the disease compared to an untreated diseased cell. That is, the gene or gene product is sufficiently specific to the treated cell that it may be used, optionally with other genes or gene products, to identify, predict, or detect efficacy of a small molecule. Thus, in some embodiments, a signature is a gene or gene product that is characteristic of efficacy of a compound in a diseased cell or the response of that diseased cell to treatment by the compound.

The term "baseline level" refers to a standard control for "normal" levels (i.e., patients without disease, patients responding to a drug, or patients not responding to a drug, etc.), but can also be comparative, e.g., where low baseline levels is compared to the levels of other subjects having the disease.

The term "multi-kinase inhibitor" refers to a composition that can reduce or block the action of more than one protein kinases. The inhibitor can reduce or block the action of a serine kinase, a tyrosine kinase, a threonine kinase and/or other types of kinases. The inhibitor can target to vascular endothelial growth factor (VEGF)-mediated angiogenesis and block the RAF/extracellular signal regulated kinase (ERK) kinase (MEK)/ERK cascade. Examples of multi-kinase inhibitors include, but are not limited to composition comprising one or more drugs such as Sorafenib (e.g., Nexavar®), vemurafenib (e.g., Zelboraf®), sunitinib (e.g., Sutent®), axitinib (e.g., Inlyta®), vandetanib (e.g., Caprelsa®), cabozantinib (e.g., Cometriq®), ponatinib (e.g., Iclusig®), ruxolitinib (e.g., Jakafi®), regorafenib (e.g., Stivarga®), crizotinib (e.g., Xalkori®), a salt, a solvate, or a physiologically functional derivative thereof, or a mixture thereof.

The term "Sorafenib" refers to salt of 4-{4-[({[4-Chloro-3-(trifluoromethyl)phenyl]amino}carbonyhamino]phenoxy}-N-methylpyridine-2-carboxamide. The synthesis and use of 4-{4-[({[4-Chloro-3-trifluoromethyl)phenyl]amino}carbonyhamino]phenoxy}-N-methylpyridine-2-carboxamide and many other ureas, as well as pharmaceutically acceptable salts thereof such as salts, formulations, physiologically functional derivatives, such as those described in a number of applications including, but not limited to, international applications WO 00/42012, WO 00/41698, WO 02/062763, WO 03/354950, WO 02/085859, WO 03/047579, WO 04/15653, WO 07/053573, WO 08/008733, WO 09/106825, WO 09/054004, WO 09/111061, WO/2013/000909, U.S. Pat. Nos. 7,235,576, 7,351,834, 7,897,623, 8,445,687, and U.S. Patent Application Publication No. 2013/0012550, each of which is incorporated herein by reference in its entirety.

The term "Sunitinib" (as known as SU11248, or Sutent) refers to N-(2-diethylaminoethyl)-5-[(Z)-(5-fluoro-2-oxo-1H-indol-3-ylidene)methyl]-2,4-dimethyl-1H-pyrrole-3-carboxamide, as well as pharmaceutically acceptable salts thereof such as salts, formulations, physiologically functional derivatives, such as those described in a number of applications including, but not limited to, international applications WO/2011/004200A1, WO/2010/011834A2, WO/2011/128699A2, WO/2011/104555A2, WO/2009/067686A2, WO/2009/067674A2, WO/2010/039798A2, WO/2011/100325A2, WO/2012/088522A1, WO/2009/124037A1, WO/2010/049449A2, WO/2009/157011A1, U.S. Pat. Nos. 6,573,293, 7,125,905, 7,211,600, and U.S. Patent Application Publication Nos. US20110263671, US20100256392, US20110034703, US20130190512, US20090247767, US20100160646, US20090062368, US20110275690, US20110092717, US20110112164, each of which is incorporated herein by reference in its entirety.

The term "Axitinib" (as known as AG013736 or Inlyta) refers to N-Methyl-2-[[3-[(E)-2-pyridin-2-ylethenyl]-1H-indazol-6-yl]sulfanyl]benzamide, as well as pharmaceutically acceptable salts thereof such as salts, formulations, physiologically functional derivatives, such as those described in a number of applications including, but not limited to, international applications WO/2013/046133A1 and WO/2011/038467A1, U.S. Pat. Nos. 6,534,524, 7,141,581, and U.S. Patent Application Publication Nos. US20090062347 and US20120244116, each of which is incorporated herein by reference in its entirety.

The term "Vandetanib" (as known as INN or Caprelsa) refers to N-(4-bromo-2-fluorophenyl)-6-methoxy-7-[(1-methylpiperidin-4-yl)methoxy]quinazolin-4-amine, as well as pharmaceutically acceptable salts thereof such as salts, formulations, physiologically functional derivatives, such as those described in a number of applications including, but not limited to, U.S. Pat. Nos. 7,173,038, 8,067,427, and RE42353, each of which is incorporated herein by reference in its entirety.

The term "Pazopanib" (as known as Votrient) refers to 5-[[4-[(2,3-Dimethyl-2H-indazol-6-yl)methylamino]-2-pyrimidinyl]amino]-2-methylbenzolsulfonamide, as well as pharmaceutically acceptable salts thereof such as salts, formulations, physiologically functional derivatives, such as those described in a number of applications including, but not limited to, international applications WO/2010/036796A1, WO/2012/073254A1, WO/2011/050159A1, WO/2011/009016A1, WO/2011/085007A1, WO/2012/103060A1, WO/2011/039648A1, WO/2011/140343A1, WO/2013/043529A1, and WO/2011/146458A1; U.S. Pat. Nos. 7,105,530, 7,262,203, and 8,114,885; and U.S. Patent Nos. US20110301113, US20120197019, US20120165354, US20110281901, US20130012531, US20120028918, and US20120232102, each of which is incorporated herein by reference in its entirety.

The term "Cabozantinib" (as known as Cometriq or XL184) refers to N-(4-((6,7-Dimethoxyquinolin-4-yl)oxy)phenyl)-N-(4-fluorophenyl)cyclopropane-1,1-dicarboxamide, as well as pharmaceutically acceptable salts thereof such as salts, formulations, physiologically functional derivatives, such as those described in a number of applications including, but not limited to, U.S. Pat. No. 7,579,473, which is incorporated herein by reference in its entirety.

The terms "treating" and "treatment" as used herein refer to an approach for obtaining beneficial or desired results including clinical results. For purposes of this invention, beneficial or desired clinical results include, but are not limited to, one or more of the following: decreasing the severity and/or frequency one or more symptoms resulting from the disease, diminishing the extent of the disease, stabilizing the disease (e.g., preventing or delaying the worsening of the disease), delay or slowing the progression of the disease, ameliorating the disease state, decreasing the dose of one or more other medications required to treat the disease, and/or increasing the quality of life. "Treating" a patient with a formulation described herein includes management of an individual to inhibit or cause regression of a disease or condition.

The term "effective amount" refers to the amount of one or more compounds that renders a desired treatment outcome. An effective amount may be comprised within one or more doses, i.e., a single dose or multiple doses may be required to achieve the desired treatment endpoint.

A "therapeutically effective amount" refers to an amount of one or more compounds sufficient to produce a desired therapeutic outcome (e.g., reduction of severity of a disease or condition). In one embodiment, the therapeutically effective amount refers to a therapeutically effective plasma concentration of a multi-kinase inhibitor. A "prophylactically effective amount" refers to an amount of a pharmaceutical formulation including one or more compounds sufficient to prevent or reduce severity of a future disease or condition when administered to an individual who is susceptible and/or who may develop a disease or condition.

By "pharmaceutically acceptable" is meant a material that is not biologically or otherwise undesirable, i.e., the material may be incorporated into a pharmaceutical composition administered to a patient without causing any significant undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration.

The term "disorder" or "disease" used interchangeably herein, refers to any alteration in the state of the body or one of its organs and/or tissues, interrupting or disturbing the performance of organ function and/or tissue function (e.g., causes organ dysfunction) and/or causing a symptom such as discomfort, dysfunction, distress, or even death to a subject afflicted with the disease.

The term "subject", "individual" or "patient" refers to an animal, for example, a mammal and includes, but is not limited to, human, bovine, horse, feline, canine, rodent, or primate. In some embodiments, the individual is a human.

The term "derivative" as used herein includes derivatives, analogs, prodrugs, and unnatural precursors.

The term "pharmaceutically acceptable salt" refers to a salt which retains the biological effectiveness of the compound and which is not biologically or otherwise undesirable.

Additional terms shall be defined, as required, in the detailed description that follows.

Cancer

The present invention provides a method for determining a subject's responsiveness or resistance to one or more drug, such as a multi-kinase inhibitor. In some embodiments, the drug is used to treat cancer.

In some embodiments, the cancer is selected from the group consisting of cancers of the tongue, mouth, pharynx, and oral cavity, esophageal cancer, stomach cancer, gastrointestinal stromal tumor, cancer of the small intestine, anal cancer, cancer of the anal canal, anorectal cancer, liver cancer, intrahepatic bile duct cancer, gallbladder cancer, biliary cancer, cancer of other digestive organs, cancer of the larynx, bone and joint cancer, uterine cancer, cervical cancer, uterine corpus cancer, cancer of the vulva, vaginal cancer, testicular cancer, penile cancer, urinary bladder cancer, kidney cancer, renal cancer, cancer of the ureter and other urinary organs, ocular cancer, brain and nervous system cancer, CNS cancers, and thyroid cancer, comprising administering to a subject in need thereof a therapeutically effective amount of β-lapachone, or a pharmaceutically acceptable salt thereof, in combination with a pharmaceutically acceptable carrier, wherein said β-lapachone, or a pharmaceutically acceptable salt thereof, treats said cancer selected from the group consisting of cancers of the tongue, mouth, pharynx, and oral cavity, esophageal cancer, stomach cancer, gastrointestinal stromal tumor, cancer of the small intestine, anal cancer, cancer of the anal canal, anorectal cancer, liver cancer, intrahepatic bile duct cancer, gallbladder cancer, biliary cancer, cancer of other digestive organs, cancer of the larynx, bone and joint cancer, uterine cancer, cervical cancer, uterine corpus cancer, cancer of the vulva, vaginal cancer, testicular cancer, penile cancer, urinary bladder cancer, kidney cancer, renal cancer, cancer of the ureter and other urinary organs, ocular cancer, brain and nervous system cancer, CNS cancers, and thyroid cancer.

In some embodiments, the cancer is a liver cancer. In some embodiments, the cancer is hepatocellular carcinoma (HCC), mesenchymal tissue, sarcoma, hepatoblastoma, cholangiocarcinoma, angiosarcoma, hemangiosarcoma, lymphoma, or mixture thereof.

Gene Markers

The present invention provides a panel of gene markers. In some embodiments, one or more members of the panel of gene markers can be used to determine a subject's responsiveness or resistance to a drug, such as a multi-kinase inhibitor.

Figure 4:
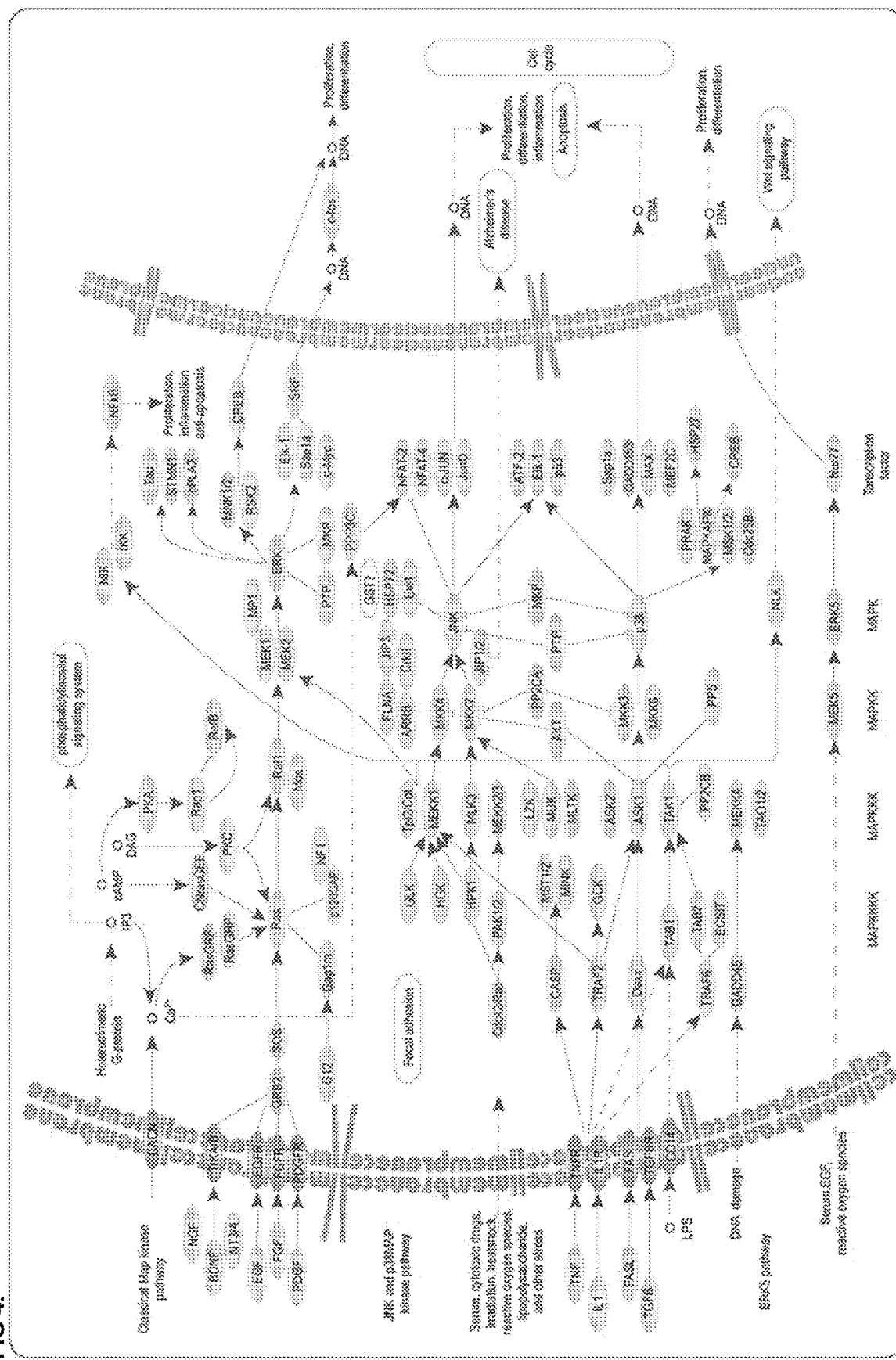
FIG. 4 shows RAF/extracellular signal regulated kinase (ERK) kinase (MEK)/ERK cascade.

In some embodiments, In some embodiments, the multi-kinase inhibitor targets to vascular endothelial growth factor (VEGF)-mediated angiogenesis and reduces the activity of or blocks the RAF/extracellular signal regulated kinase (ERK) kinase (MEK)/ERK cascade (see FIG. 4), including, but not limited to, Sorafenib (e.g., Nexavar®), vemurafenib (e.g., Zelboraf®), sunitinib (e.g., Sutent®), axitinib (e.g., Inlyta®), vandetanib (e.g., Caprelsa®), cabozantinib (e.g., Cometriq®), ponatinib (e.g., Iclusig®), ruxolitinib (e.g., Jakafi®), regorafenib (e.g., Stivarga®), crizotinib (e.g., Xalkori®), a salt, a solvate, or a physiologically functional derivative thereof, or a mixture thereof.

In some embodiments, the panel of gene markers include at least one, two, three, four, five, six, sever, or eight of the following genes:

SEC14L2: a.k.a. SEC14-Like2, Squalene Transfer Protein, TAP, Supernatant Protein Factor, C22orf6, SPF, KIAA1186, KIAA1658, Tocopherol-Associated Protein, Alpha-Tocopherol-Associated Protein, or HTAP, e.g., having the nucleotide sequence of GenBank ID AL096881, and polypeptide sequence of UniProtKB:O76054, or functional variants, fragments, or orthologs thereof. In some embodiments, the SEC14L2 marker comprises transcript variant 1 (SEQ ID NO: 1) or SEC14L2 isoform 1 (SEQ ID NO: 2), functional variants, fragments, or orthologs thereof. In some embodiments, the SEC14L2 marker comprises transcript variant 2 (SEQ ID NO: 3) or SEC14L2 isoform 2 (SEQ ID NO: 4), functional variants, fragments, or orthologs thereof. In some embodiments, the SEC14L2 marker comprises transcript variant 3 (SEQ ID NO: 5) or SEC14L2 isoform 3 (SEQ ID NO: 6), functional variants, fragments, or orthologs thereof. In some embodiments, an activity of SEC14L2 within a predetermined activity level indicates that the subject is responsive to the treatment of a multi-kinase inhibitor. In some embodiments, an activity of SEC14L2 in a subject similar to, or lower than a predetermined activity level indicates that the subject is responsive to the treatment of a multi-kinase inhibitor. In some embodiments, an activity of SEC14L2 in a subject higher than a predetermined activity level indicates that the subject is not responsive to the treatment of a multi-kinase inhibitor. As used herein, the term "similar" refers to that there is no significant statistical difference between the activity of a gene marker in a subject and a predetermined activity level. As used herein, the term "lower" or "higher" refers to that there is a statistical difference between the activity of a gene marker in a subject and a predetermined activity level to determine there the activity of a gene marker in a subject is less or more when compared to a predetermined activity level.

H6PD: a.k.a. hexose-6-phosphate dehydrogenase (glucose 1-dehydrogenase), GDH/6PGL Endoplasmic Bifunctional Protein, GDH, Glucose 1-Dehydrogenase, Glucose Dehyrogenase, Glucose Dehydrogenase, G6PDH, Salivary Dehydrogenase, 6-Phosphogluconolactonase, CORTRD1, G6PD, H Form, EC 1.1.1.49, EC 2.7.4.3, or EC 3.1.1.31, e.g., having the nucleotide sequence of GenBank ID CAA10071.1, and the polypeptide sequence of UniProtKB: O95479, or functional variants, fragments, or orthologs thereof. In some embodiments, the H6PD marker comprises transcript variant 1 (SEQ ID NO: 7) or H6PD isoform 1 (SEQ ID NO: 8), functional variants, fragments, or orthologs thereof. In some embodiments, the H6PD marker comprises transcript variant 2 (SEQ ID NO: 9) or H6PD isoform 2 (SEQ ID NO: 10), functional variants, fragments, or orthologs thereof. In some embodiments, an activity of H6PD within a predetermined activity level indicates that the subject is responsive to the treatment of a multi-kinase inhibitor. In some embodiments, an activity of H6PD in a subject similar to, or lower than a predetermined activity level indicates that the subject is responsive to the treatment of a multi-kinase inhibitor. In some embodiments, an activity of H6PD in a subject higher than a predetermined activity level indicates that the subject is not responsive to the treatment of a multi-kinase inhibitor.

TMEM140: a.k.a. transmembrane protein 140, e.g., having the nucleotide sequence of GenBank ID NM_018295.3, and the polypeptide sequence of UniProtKB: Q9NV12, or functional variants, fragments, or orthologs thereof. In some embodiments, the TMEM140 marker comprises TMEM140 transcript SEQ ID NO: 11 or TMEM140 polypeptide SEQ ID NO: 12, functional variants, fragments, or orthologs thereof. In some embodiments, an activity of TMEM140 within a predetermined activity level indicates that the subject is responsive to the treatment of a multi-kinase inhibitor. In some embodiments, an activity of TMEM140 in a subject similar to, or lower than a predetermined activity level indicates that the subject is responsive to the treatment of a multi-kinase inhibitor. In some embodiments, an activity of TMEM140 in a subject higher than a predetermined activity level indicates that the subject is not responsive to the treatment of a multi-kinase inhibitor.

SLC2A5: a.k.a., solute carrier family 2 (facilitated glucose/fructose transporter), member 5, Glucose Transporter-Like Protein 5, GLUT51, Solute Carrier Family 2, Facilitated Glucose Transporter Member 5, Glucose Transporter Type 5, Small Intestine, Fructose Transporter, GLUT-5, e.g., having the nucleotide sequence of GenBank ID NM_001135585 or NM_003039, and the polypeptide sequence of UniProtKB: P22732, or functional variants, fragments, or orthologs thereof. In some embodiments, the SLC2A5 marker comprises transcript variant 1 (SEQ ID NO: 13) or SLC2A5 isoform 1 (SEQ ID NO: 14), functional variants, fragments, or orthologs thereof. In some embodiments, the SLC2A5 marker comprises transcript variant 2 (SEQ ID NO: 15) or SLC2A5 isoform 2 (SEQ ID NO: 16), functional variants, fragments, or orthologs thereof. In some embodiments, an activity of SLC2A5 within a predetermined activity level indicates that the subject is responsive to the treatment of a multi-kinase inhibitor. In some embodiments, an activity of SLC2A5 in a subject similar to, or lower than a predetermined activity level indicates that the subject is responsive to the treatment of a multi-kinase inhibitor. In some embodiments, an activity of SLC2A5 in a subject higher than a predetermined activity level indicates that the subject is not responsive to the treatment of a multi-kinase inhibitor.

ACTA1, a.k.a., actin, alpha 1, skeletal muscle, CFTDM, ACTA, MPFD, NEM3, NEM2, ASMA, Actin, Alpha Skeletal Muscle, CFTD1, Nemaline Myopathy Type 3, NEM1, Alpha-Actin-1, or CFTD, e.g., having the nucleotide sequence of GenBank ID NM_001100.3, and the polypeptide sequence of UniProtKB: P68133, or functional variants, fragments, or orthologs thereof. In some embodiments, the ACTA1 marker comprises ACTA1 transcript SEQ ID NO: 17 or ACTA1 polypeptide SEQ ID NO: 18, functional variants, fragments, or orthologs thereof. In some embodiments, an activity of ACTA1 within a predetermined activity level indicates that the subject is responsive to the treatment of a multi-kinase inhibitor. In some embodiments, an activity of ACTA1 in a subject similar to, or lower than a predetermined activity level indicates that the subject is responsive to the treatment of a multi-kinase inhibitor. In some embodiments, an activity of ACTA1 in a subject higher than a predetermined activity level indicates that the subject is not responsive to the treatment of a multi-kinase inhibitor.

IRF8: a.k.a., interferon regulatory factor 8, Interferon Consensus Sequence Binding Protein 1, ICSBP, H-ICSBP, ICSBP1, Interferon Consensus Sequence-Binding Protein, or IRF-8, e.g., having the nucleotide sequence of GenBank ID NM_002163.2, NM_001252275.1 or NM_006798.3, and the polypeptide sequence of UniProtKB: Q02556, or functional variants, fragments, or orthologs thereof. In some embodiments, the IRF8 marker comprises IRF8 transcript SEQ ID NO: 19 or IRF8 polypeptide SEQ ID NO: 20, functional variants, fragments, or orthologs thereof. In some embodiments, an activity of IRF-8 within a predetermined activity level indicates that the subject is responsive to the treatment of a multi-kinase inhibitor. In some embodiments, an activity of IRF8 in a subject similar to, or lower than a predetermined activity level indicates that the subject is responsive to the treatment of a multi-kinase inhibitor. In some embodiments, an activity of IRF8 in a subject higher than a predetermined activity level indicates that the subject is not responsive to the treatment of a multi-kinase inhibitor.

STAT2: a.k.a., signal transducer and activator of transcription 2, P113, STAT113, Interferon Alpha Induced Transcriptional Activator, Signal Transducer And Activator Of Transcription 2, Signal Transducer And Activator Of Transcription 2, ISGF-32, e.g., having the nucleotide sequence of GenBank ID NM_005419.3 or NM_198332.1, and the polypeptide sequence of UniProtKB: P52630, or functional variants, fragments, or orthologs thereof. In some embodiments, the STAT2 marker comprises transcript variant 1 (SEQ ID NO: 21) or STAT2 isoform 1 (SEQ ID NO: 22), functional variants, fragments, or orthologs thereof. In some embodiments, the STAT2 marker comprises transcript variant 2 (SEQ ID NO: 23) or STAT2 isoform 2 (SEQ ID NO: 24), functional variants, fragments, or orthologs thereof. In some embodiments, an activity of STAT2 within a predetermined activity level indicates that the subject is responsive to the treatment of a multi-kinase inhibitor. In some embodiments, an activity of STAT2 in a subject similar to, or lower than a predetermined activity level indicates that the subject is responsive to the treatment of a multi-kinase inhibitor. In some embodiments, an activity of STAT2 in a subject higher than a predetermined activity level indicates that the subject is not responsive to the treatment of a multi-kinase inhibitor.

UGT2A1: a.k.a., UGT2A2, UDP glucuronosyltransferase 2 family, polypeptide A1, complex locus; UDP Glucuronosyltransferase 2 Family, Polypeptide A1; UDP Glycosyltransferase 2 Family, Polypeptide A1; UDP-Glucuronosyltransferase 2A1; UDPGT 2A1; UGT2A2; or EC 2.4.1.17, e.g., having the nucleotide sequence of GenBank ID NM_001252274.1 NM_001252275.1 or NM_006798.3, and the polypeptide sequence of UniProtKB: Q9Y4X1, or functional variants, fragments, or orthologs thereof. In some embodiments, the UGT2A1 marker comprises transcript variant 1 (SEQ ID NO: 25) or UGT2A1 isoform 1 (SEQ ID NO: 26), functional variants, fragments, or orthologs thereof. In some embodiments, the UGT2A1 marker comprises transcript variant 2 (SEQ ID NO: 27) or UGT2A1 isoform 2 (SEQ ID NO: 28), functional variants, fragments, or orthologs thereof. In some embodiments, the UGT2A1 marker comprises transcript variant 2 (SEQ ID NO: 29) or UGT2A1 isoform 2 (SEQ ID NO: 30), functional variants, fragments, or orthologs thereof. In some embodiments, an activity of UGT2A1 within a predetermined activity level indicates that the subject is responsive to the treatment of a multi-kinase inhibitor. In some embodiments, an activity of UGT2A1 in a subject similar to, or lower than a predetermined activity level indicates that the subject is responsive to the treatment of a multi-kinase inhibitor. In some embodiments, an activity of UGT2A1 in a subject higher than a predetermined activity level indicates that the subject is not responsive to the treatment of a multi-kinase inhibitor.

The present invention also provides activity profiles of a panel of gene markers comprising at least one, two, three, four, five, six, seven, eight or more gene markers. In some embodiments, the gene markers are selected from the group consisting of SEC14L2, H6PD, TMEM140, SLC2A5, ACTA1, IRF8, STAT2, and UGT2A1, or functional variants, fragments, or orthologs thereof.

In some embodiments, while more than one gene markers of the present application are used, a determination of responsiveness can be made based on activities of one or more gene markers. Under such situations, a conclusion can be made that the subject is most likely responsive or most likely not responsive to the treatment. In some embodiments, while more than one gene markers of the present application are used, the activity of each gene marker carries the same "weight" or determination factor with respect to determining whether the subject is responsive to the treatment of a multi-kinase inhibitor. In some embodiments, while more than one gene markers of the present application are used, the activity of each gene marker carries different "weight" or determination factor with respect to determining whether the subject is non-responsive to the treatment of a multi-kinase inhibitor. In some embodiments, the weight can be determined by a predictive power of the marker, which can be quantified by the coefficient of determination (r2) and the associated p-value. In some embodiments, higher values of r2 and/or lower values of p-value indicate better predictive power.

In some embodiments, while more than one gene markers of the present application are used and some gene markers indicate the subject is responsive to the treatment of a multi-kinase inhibitor, while some gene markers indicate that the subject may not be responsive to the treatment of a multi-kinase inhibitor, or the result is inconclusive based on the activity of all gene markers used, a conclusion can be made based on overall activities of the gene markers used or a particular subset of gene markers used, e.g., that the subject is most likely responsive or most likely not responsive to the treatment based on the numbers of gene marker indicating the responsiveness. For example, when a total of n gene markers are tested (n=2, 3, 4, or more etc.), if m gene markers indicate that the subject is responsive to the treatment, while m is not smaller than n-m, then a conclusion can be made that the subject is likely responsive to the treatment. If m is smaller than n-m, then a conclusion can be made that the subject is likely not responsive to the treatment.

As used herein, the term "activity profile" refers to a set of data representing distinctive features or characteristics of one or more gene markers. Such features or characteristics include, but are not limited to, transcript abundance, transcript stability, transcription rate, translation rate, post-translation modification, protein abundance, protein stability, and/or protein enzymatic activity, etc. In some embodiments, the activity profile comprises data related to gene expression level of each gene marker.

In some embodiments, a collection of activity profiles of a panel of gene markers is provided. In some embodiments, the collection comprises activity profiles is obtained from a specific population of subjects. In some embodiments, the specific population of subjects consists of subjects that are responsive to a multi-kinase inhibitor. In some embodiments, the specific population of subjects consists of subjects that are not responsive to a multi-kinase inhibitor.

In some embodiments, the collection comprises activity profiles that are statistically homogeneous in one or more aspects, e.g., statistically homogeneous in one or more quantitative or semi-quantitative parameters describing the features and characteristics of the activity profiles. In some embodiments, the quantitative parameters include, but are not limited to, transcript abundance, transcript stability, transcription rate, translation rate, post-translation modification, protein abundance, protein stability, and/or protein enzymatic activity, etc. Whether a group of activity profiles are statistically homogeneous or not in one or more aspects can be determined by any suitable statistic test and/or algorithm known to one skilled in the art.

In some embodiments, one or more of the gene markers increase its activity in response to the multi-kinase inhibitor. In some embodiments, one or more of the gene markers decrease its activity in response to the multi-kinase inhibitor. In some embodiments, one or more of the gene markers remains its activity in response to the multi-kinase inhibitor. As used herein, the term "gene activity" refers to gene expression level, RNA activity level, or protein activity level. As used herein, the term "RNA activity level refers to mRNA abundance, synthesis rate, and/or stability, etc. As used herein, the term "protein activity level" refers to protein abundance, synthesis rate, stability, enzymatic activity, phosphorylation rate, etc.

In some embodiments, the collection of activity profiles of one or more gene markers of the present invention is obtained from one or more tests. The test can be performed by the subject himself/herself, by a doctor, by a nurse, by a test lab, by a healthcare provider, or any other parties capable of doing the test. The test results containing the collection of activity profiles can be then analyzed by the same party or by a second party, such as the subject himself/herself, a doctor, a nurse, test lab, a healthcare provider, a physician, a clinical trial personnel, a hospital, a lab, a research institute, or any other parties capable of analyzing the test to determine if the subject is responsive to the drug.

Despite how the activity of the gene markers of the present invention changes after the treatment of the multi-kinase inhibitor, for all gene markers described herein, their expression level is lower before the treatment when compared to the average expression level of randomly selected patients, or patients not responding to the treatment. Therefore, the expression level of patients responding to the treatment can be used as a reference. When the expression level of one or more of the presently described gene markers is within the expression level of patients responding to the treatment, it indicates the responsiveness of the subject. In other words, before the multi-kinase inhibitor treatment, the expression of these gene markers of a given subject in comparison to a predetermined expression level of a population of subjects responding to the treatment can be used to predict the probability of response to multi-kinase inhibitor treatment. Alternatively, the expression level of patients not responding to the treatment can also be used. For example, before the multi-kinase inhibitor treatment, when the expression level of one or more of the presently described gene markers of a given subject is within the expression level of patients not responding to the treatment, it indicates the non-responsiveness of the subject.

Methods

Also provided are methods of using the panel of gene markers of the present invention.

In some embodiments, methods for determining a subject's responsiveness or resistance to a drug are provided. In some embodiments, the multi-kinase inhibitor targets to vascular endothelial growth factor (VEGF)-mediated angiogenesis and reduces the activity of or blocks the RAF/extracellular signal regulated kinase (ERK) kinase (MEK)/ERK cascade (see FIG. 4).

In some embodiments, the drug comprises one or more multi-kinase inhibitors, such as an inhibitor that can target to vascular endothelial growth factor (VEGF)-mediated angiogenesis and block the RAF/extracellular signal regulated kinase (ERK) kinase (MEK)/ERK cascade, including but not limited to, Sorafenib (e.g., Nexavar®), vemurafenib (e.g., Zelboraf®), sunitinib (e.g., Sutent®), axitinib (e.g., Inlyta®), vandetanib (e.g., Caprelsa®), cabozantinib (e.g., Cometriq®), ponatinib (e.g., Iclusig®), ruxolitinib (e.g., Jakafi®), regorafenib (e.g., Stivarga®), crizotinib (e.g., Xalkori®), a salt, a solvate, or a physiologically functional derivative thereof, or a mixture thereof. In some embodiments, the drug is Sorafenib, Axitinib, Vandetanib, Pazopanib, Cabozantinib, a salt, a solvate, or a physiologically functional derivative thereof, or a mixture thereof.

In some embodiments, the drug is used to treat a disease associated with cancer. In some embodiments, the cancer is a liver cancer or a kidney cancer. In some embodiments, the liver cancer is hepatocellular carcinoma.

In some embodiments, the methods comprise measuring activity profile of a panel of gene markers in a sample collected from the subject comprising at least one or more markers selected from the group of SEC14L2, H6PD, TMEM140, SLC2A5, ACTA1, IRF8, STAT2, and UGT2A1.

In some embodiments, the methods further comprise comparing the activity profile of the panel to a predetermined activity profile derived from a population of subjects responding to a multi-kinase inhibitor, wherein the subject is determined to be responsive to the multi-kinase inhibitor if the activity profile of the panel is within the predetermined activity profile.

In some embodiments, the methods further comprise comparing the activity profile of the panel to activity profile derived from a population of subjects not responding to a multi-kinase inhibitor, wherein the subject is determined to be not responsive to the multi-kinase inhibitor if the activity profile of the panel is within the activity profile.

As used herein, the term "predetermined level", "predetermined activity profile" or a "reference activity profile" refers to a standardized data or data set representing the average, representative features or characteristics of one or more gene markers in the population of subjects responsive to a multi-kinase inhibitor treatment. Such features or characteristics include, but are not limited to, transcript abundance, transcript stability, transcription rate, translation rate, post-translation modification, protein abundance, protein stability, and/or protein enzymatic activity, etc. In some embodiments, the specific population of subjects are consisting of about 5, about 10, about 20, about 50, about 100, about 200, about 300, about 400, about 500, about 1000, about 5000, about 10K, or more individual subjects. The predetermined activity profile can be a standardized data or data set collected before, during, or after the specific population of subjects has been all exposed to a multi-kinase inhibitor. In some embodiments, the predetermined activity profile is a standardized data or data set collected before the specific population of subjects has been all exposed to a multi-kinase inhibitor. (or from sample from cell, tumor cells, In some embodiments, the predetermined activity profile is a predetermined bar or threshold level. A higher than predetermined bar or threshold activity of a given gene marker of the present invention in a subject indicates that the subject is not responsive to the treatment, while a similar or lower activity than predetermined bar or threshold activity of a given gene marker of the present invention in a subject indicates that the subject is responsive to the treatment.

In some embodiments, the predetermined activity profile is a predetermined range. An activity of a given gene marker of the present invention in a subject higher or outside the range indicates that the subject is not responsive to the treatment, while an activity of a given gene marker of the present invention in a subject within or lower than the range indicates that the subject is responsive to the treatment.

It is understood that instead of obtaining the predetermined activity profile from a group of subjects known to be responsive to the treatment, a "negative predetermined activity profile" can be obtained from subjects known to be not responsive to the treatment. In some embodiments, an activity of a given gene marker of the present invention in a subject similar to, or higher than a negative predetermined activity level indicates that the subject is not responsive to the treatment of a multi-kinase inhibitor. In some embodiments, an activity of a given gene marker of the present invention in a subject lower than a negative predetermined activity level indicates that the subject is responsive to the treatment of a multi-kinase inhibitor.

As used herein, a subject is "responsive" to a multi-kinase inhibitor when the vascular endothelial growth factor (VEGF)-mediated angiogenesis in the subject is reduced or blocked by the multi-kinase inhibitor, and the activity of the RAF/extracellular signal regulated kinase (ERK) kinase (MEK)/ERK cascade in the subject is reduced or blocked, which can be tested by any suitable methods known to one skilled in the art. In some embodiments, the responsiveness can be reflected by antitumor activity of a multi-kinase inhibitor. In some embodiments, the antitumor activity of a multi-kinase inhibitor can be measured by % $\Delta T/\Delta C$, wherein ΔT=tumor volume change in the treatment group and ΔC=tumor volume change in control group. In some embodiments, the antitumor activity of a multi-kinase inhibitor can be measured in any suitable sample collected from a subject, part of a subject, or PDX derived from a subject. In some embodiments, a subject is considered responsive to a multi-kinase inhibitor when a predicted % ΔT/ΔC is less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, or even less depending on the types of the multi-kinase inhibitor and the types of the tumor. In some embodiments, the subject is predicted to be responsive to a multi-kinase inhibitor when a predicted % ΔT/ΔC corresponding to the activity profiles of one or more gene markers is less than about 40%.

As used herein, the sentence "the activity profile of the panel is within the predetermined activity profile" refers to that the activity profile been analyzed is similar to the predetermined activity profile, for example, the parameters describing the activity profile are close to the parameters describing the predetermined activity profile, or within the variation range of a predetermined activity profile, e.g., the parameters are within the variation range based on a confidence interval of 90% constructed from the parameters describing the predetermined activity profile.

The activity profile of the panel can be described by any suitable parameters. In some embodiments, the activity profile of the panel is described by signature values associated with one or more gene markers expressed in the subject to be evaluated. Accordingly, the predetermined activity profile is described by the signature value associated with the gene markers expressed in the reference group.

In some embodiments, when the activity profile of the panel of gene markers in a sample collected from a subject been analyzed is within a predetermined activity profile based on a population of subjects responsive to a multi-kinase inhibitor treatment, the subject been analyzed is determined to be responsive to the multi-kinase inhibitor.

Alternatively, when the activity profile of the panel of gene markers in a sample collected from a subject been analyzed is within a standardized data or data set representing the average, representative features or characteristics of one or more gene markers in the population of subjects not responsive to a multi-kinase inhibitor treatment, the subject been analyzed is determined to be not responsive to the multi-kinase inhibitor.

Methods for administering a multi-kinase inhibitor to a subject are provided. In some embodiments, the methods comprise testing the subject for activity profile of a panel of gene markers comprising at least one or more gene markers. In some embodiments, the gene markers are selected from the group consisting of SEC14L2, H6PD, TMEM140, SLC2A5, ACTA1, IRF8, STAT2, and UGT2A1.

In some embodiments, the methods further comprises comparing the activity profile of the panel to a predetermined activity, wherein the multi-kinase inhibitor is administered to the subject if the activity profile of the panel is within the predetermined activity profile. In some embodiments, the multi-kinase inhibitor targets to vascular endothelial growth factor (VEGF)-mediated angiogenesis and reduces the activity of or blocks the RAF/extracellular signal regulated kinase (ERK) kinase (MEK)/ERK cascade (see FIG. 4).

The activity profile of a panel of gene markers can be determined by any suitable methods known to one skilled in the art. In some embodiments, a biological sample is taken from a subject and analyzed. The gene activity can be gene copy number, gene amplification number, or promoter activity, etc. RNA activity can be mRNA abundance, synthesis rate, and/or stability, etc. Protein activity can be protein abundance, synthesis rate, stability, enzymatic activity, phosphorylation rate, modifications, binding activity, etc. In some embodiments, the biological sample is then typically assayed from the presence of one or more gene expression products such as RNA, mRNA, cDNA, cRNA, protein, etc.

In some embodiments, mRNA from a biological sample is directly used in determining the levels of expression of one or more genes by hybridization. In some particular embodiments, RNA is obtained from a biological sample. The RNA is then transformed into cDNA (complementary DNA) copy using methods known in the art. In some particular embodiments, the cDNA is labeled with a fluorescent label or other detectable label. The cDNA is then hybridized to a substrate containing a plurality of probes of interest. A probe of interest typically hybridizes under stringent hybridization conditions to at least one DNA sequence of a gene signature. In certain embodiments, the plurality of probes are capable of hybridizing to the sequences derived from the gene markers selected from SEC14L2, H6PD, TMEM140, SLC2A5, ACTA1, IRF8, STAT2, and UGT2A1 under the hybridization conditions. In some embodiments, the conditions comprise using 6×SSC (0.9 M NaCl, 0.09 M sodium citrate, pH 7.4) at 65° C. The probes may comprise nucleic acids. The term "nucleic acid" encompasses known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, peptide-nucleic acids (PNAs).

In certain cases, the probes will be from about 15 to about 50 base pairs or more in length. The amount of cDNA hybridization can be measured by assaying for the presence of the detectable label, such as a fluorophore. The quantification of the hybridization signal can be used to generate a score for a particular sequence or set of sequences in the gene signature for a particular patient or plurality of patients.

Included within the scope of the invention are DNA arrays or microarrays containing a plurality of sequences that hybridize under stringent hybridization conditions to one or more of the gene sequences of the markers. An example of a substrate containing one or more probes of interest is a plurality of DNA probes that are affixed to a substrate. In certain embodiments, the substrate may comprise one or more materials such as gel, nitrocellulose, nylon, quartz, glass, metal, silica based materials, silica, resins, polymers, etc., or combinations thereof. Typically, the DNA probes comprise about 10-50 bp of contiguous DNA. In certain embodiments, the DNA probes are from about 20 to about 50 bp of contiguous DNA. In certain embodiments, the present invention relates to kits which comprising a microarray directions for its use. The kit may comprise a container which comprises one or more microarrays and directions for their use.

The biological sample may also be analyzed for gene expression of one or more gene markers using methods that can detect nucleic acids including, but not limited to, PCR (polymerase chain reaction); RT-PCT (reverse transcriptase-polymerase chain reaction); quantitative or semi-quantitative PCR, etc.

In certain embodiments, the levels of gene expression are measured by detecting the protein expression products of the genes or DNA sequences. The levels of protein products may be measured using methods known in the art including the use of antibodies which specifically bind to a particular protein. These antibodies, including polyclonal or monoclonal antibodies, may be produced using methods that are known in the art. These antibodies may also be coupled to a solid substrate to form an antibody chip or antibody microarray. Antibody or protein microarrays may be made using methods that are known in the art.

Once the levels of gene expression have been measured then a signature value/score is calculated. Examples of how to calculate a signature value/score are described herein. In some embodiments, the average mRNA expression intensity, in log 2-scale, of the marker gene is designated as the signature score. The signature value/score is then compared to the signature value associated with the predetermined activity profile to predict the subject's response to multi-kinase inhibitor treatment. In some embodiments, the predicted subject's response is measured by a predicted % $\Delta T/\Delta C$, wherein $\Delta T$=tumor volume change in the treatment group and $\Delta C$=tumor volume change in control group.

The signature value can be calculated by any suitable method. In some embodiments, the signature value is calculated by a pre-determined algorism. In some embodiments, a value is assigned to each gene marker based on its expression level. Non-limiting examples of methods for calculating signature value are described in Chang et al. (SIGNATURE: A workbench for gene expression signature analysis, BMC Bioinformatics 2011, 12:443), Kawaguchi et al. (Gene expression signature-based prognostic risk score in patients with glioblastoma, Cancer Sci. 2013 Jun. 7. [Epub ahead of print]), Cuzick et al. (Prognostic value of an RNA expression signature derived from cell cycle proliferation genes in patients with prostate cancer: a retrospective study, Lancet Oncol. 2011 March; 12(3):245-55. doi: 10.1016/S1470-2045(10)70295-3), Sanchez-Navarro (An 8-gene qRT-PCR-based gene expression score that has prognostic value in early breast cancer., BMC Cancer. 2010 Jun. 28; 10:336. doi: 10.1186/1471-2407-10-336), Shi et al. (A Network-Based Gene Expression Signature Informs Prognosis and Treatment for Colorectal Cancer Patients, PLoS ONE, 2012, 7(7):e412), Matsui et al. (Developing and Validating Continuous Genomic Signatures in Randomized Clinical Trials for Predictive Medicine, Clinical Cancer Research, 2012, 2012; doi: 10.1158/1078-0432.CCR-12-1206), Lyng et al. (Gene Expression Signatures That Predict Outcome of Tamoxifen-Treated Estrogen Receptor-Positive, High-Risk, Primary Breast Cancer Patients: A DBCG Study, PLoS ONE, 2013, 8(1):e54078), and Zhao et al. (Combining Gene Signatures Improves Prediction of Breast Cancer Survival, PLoS ONE, 2011, 6(3):e17845), each of which is incorporated herein by reference in its entirety.

Although there is no absolute threshold expression level required in order to determine if a subject is responding to a treatment, one skilled in the art would be able to determine a suitable standard threshold based on the types of the multi-kinase inhibitor and the diseased to be treated. For example, in some embodiments, to be convenient, when the predicted % $\Delta T/\Delta C$ associated with the signature value of gene markers is less than about 40% (or other preferred value), the subject can be determined to be responding to a given multi-kinase inhibitor.

In some embodiments, the methods of the present invention can be applied on a dosage basis. For example, for each pre-determined dosage of the same multi-kinase inhibitor, a set of gene markers can be identified, and these gene markers can be used to determine if a specific subject is responding to a specific multi-kinase at the pre-determined dosage. None limiting examples of dosage to be administered include, about 0.1 µg/kg, about 1 µg/kg, about 10 µg/kg, about 100 µg/kg, about 1 mg/kg, about 10 mg/kg, about 50 mg/kg, about 100 mg/kg, or more.

In some embodiments, the methods of the present invention can be applied on an administration method basis. For example, for each pre-determined drug administration method of the same multi-kinase inhibitor, a set of gene markers can be identified, and these gene markers can be used to determine if a specific subject is responding to the multi-kinase inhibitor by using the pre-determined drug administration method. None limiting examples of a route for administration include, mucosal, enteral, parental, transdermal/transmucosal, and inhalation. In one embodiment, the mucosal route is via the nasal, oropharyngeal, ocular, or genitourinary mucosa. In another embodiment, the enteral route is oral, rectal or sublingual. Still in another embodiment, the parenteral route is any one of intraarterial, intradermal, intramuscular, intraperitoneal, intravenous, subcutaneous, and submucosal injection or infusion. Still in another embodiment, the transdermal/transmucosal route is topical. Still in another embodiment, the inhalation route is intranasal, oropharyngeal, intratracheal, intrapulmonary or transpulmonary.

In some embodiments, the methods of the present invention can be applied on a drug combination basis. For example, for each pre-determined drug combination of a multi-kinase inhibitor and a non-multi-kinase inhibitor, or a combination of two or more multi-kinase inhibitors, a set of gene markers can be identified, and these gene markers can be used to determine if a specific subject is responding to the drug combination comprising a multi-kinase inhibitor.

In some embodiments, the methods of the present invention can be applied on a formulation basis. For example, for each pre-determined drug formulation of a given multi-kinase inhibitor, a set of gene markers can be identified, and these gene markers can be used to determine if a specific subject is responding to the multi-kinase inhibitor by using the pre-determined drug formulation.

The gene markers and associated methods of the present invention can be used for all suitable purposes. In some embodiments, they are used in prospective clinical trial. In some embodiments, they are used in clinical treatment/prevention practice.

Also provided are methods to discover predictive gene markers. In some embodiments, the methods comprise a "phase II clinical trial-like" study. In some embodiments, the methods comprise applying one or more drugs to cells derived from a subject and measuring the expressing profile of one or more genes in the cells. In some embodiments, the study comprises using PDX models. In some embodiments, the study comprises using bioinformatic and statistic analysis. In some embodiments, the bioinformatic and statistic analysis are used to identify a panel of specific gene markers which have a high correlation with drug response or drug resistance. The potential applications include, but are not limited to: a) discovery of biomarkers for early stage clinical drug candidate; b) indication selection and expansion; c) life cycle management for marketed drugs; d) novel indication discovery for "me-too" drugs.

In some embodiments, the efficacy of Sorafenib, Sunitinib, Axitinib, Vandetanib, Pazopanib, Cabozantinib or other multi-kinase inhibitors is measured on a panel of PDX models. In some embodiments, each panel has multiple mice, at least 3, 4, 5, 6, 7, 8, 9, 10 or more. In some embodiments, a control group and a treatment group is included. The control group receives vehicle only. The treatment group receives Sorafenib, Sunitinib, Axitinib, Vandetanib, Pazopanib, Cabozantinib or other multi-kinase inhibitors.

In some embodiments, for each PDX panel, drug efficacy is quantified by % $\Delta T/\Delta C$, wherein $\Delta T$ is the tumor volume change in the treatment group and $\Delta C$ is the tumor volume change in control group. In some embodiments, mRNA expression levels of 1, 2, 3, 4, 5, 6, 7, 8 or more tested marker genes are profiled by microarray, RNAseq, and/or RT-PCR. In some embodiments, the protein levels of the markers are profiled by immunoassay. In some embodiments, a signature score is calculated based on the expressions or the protein levels of the marker genes, and its predictive power is quantified by the coefficient of determination ($r2$) and the associated p-value. In some embodiments, a higher values of $r2$ and/or lower values of p-value indicate better predictive power. In some embodiments, a p-value at least smaller than 0.05 is used for considering the signature have any predictive power.

This invention is further illustrated by the following examples which should not be construed as limiting. The contents of all references, patents and published patent applications cited throughout this application, as well as the Figures and the Sequence Listing, are incorporated herein by reference.

EXAMPLES

Example 1. Significant Numbers of HCC HuPrime® Models are Sensitive or Partially Sensitive to Sorafenib Experimental models capturing human HCC oncogenic mechanisms are critical to evaluate HCC treatments and discover biomarkers predictive of patient response. Patient derived xenograft (PDX) models mirror patients' histopathological and genetic profiles (2-7). We have recently established a large collection of HCC-PDX models (named as HCC-HuPrime®, or patient avatars) by engrafting the treatment naïve patient tumor tissue fragments into immunocompromised mice. We tested Sorafenib on a randomized cohort of the HCC-HuPrime in clinical trial-like study. The study led to identification of "responders and non-responders". We next expression-profiled these models using microarray GeneChip technology. By applying statistic analysis, we have identified a specific molecular signature that are associated with the response, or called HuSignature®. The gene expression signature, consist of only a few genes, can be predictive of the response of HCC patients to Sorafenib and also amendable for developing the companion diagnostics to used for patient stratification in the clinic. This signature can be used as guide to treat the HCC patient likely to be responders, while avoid treating those unlikely responders, thus maximizing treatment benefit while minimizing an individualized.

We have established a large of panel of HCC PDX models by transplanting surgically removed tumor tissues from treatment naïve Asian HCC patients via subcutaneous engraftment in Balb/c nude mice. The take-rate for HCC engraftment is at ~20%, moderate as compared to high take-rate for colorectal (CRC) (8), and similar to those for NSCLC (9, 10). We were interested in identifying models that would respond or not respond to Sorafenib. To this end, we tested a cohort of randomly selected 21 HCC HuPrime by treating them with Sorafenib. The results demonstrated that majority of HCC models treated by daily oral administration of Sorafenib at the doses of 50 mg/kg showed varying degree of responses to the treatment as measured by % $\Delta T/\Delta C$ (FIG. 1) (Table 1). 13 out of 21 PDXs (62%) achieved effective tumor growth inhibition with % $\Delta T/\Delta C<40\%$ ($p<0.05$). On the other hand, there are also models that are quite or partially resistant to Sorafenib, non- or poor responders, including models L10334 and L10050 as shown in FIG. 1.

TABLE 1

| Model # | Sorafenib | $\Delta T/\Delta C$ (day14-day15) | P value |
|---|---|---|---|
| 001 | LIM348 | 50 mg/kg p.o. qd × 14 | (0.02) | 0.001 |
| 002 | LIM1025 | 50 mg/kg p.o. qd × 14 | 0.01 | <0.001 |
| 003 | LIM752 | 50 mg/kg p.o. qd × 14 | 0.10 | <0.001 |
| 004 | LIM1081 | 50 mg/kg p.o. qd × 13 | 0.14 | 0.015 |
| 005 | LIM1098 | 50 mg/kg qd × 14 p.o. | 0.14 | 0.008 |
| 006 | LIM612 | 50 mg/kg p.o. Qd × 22 | 0.15 | 0.001 |
| 007 | LIM1035 | 50 mg/kg p.o. qd × 14 | 0.16 | 0.005 |
| 008 | LIM1005 | 50 mg/kg p.o. qd × 14 | 0.21 | 0.015 |
| 009 | LIM574 | 50 mg/kg p.o. qd × 14 | 0.21 | 0.002 |
| 010 | LIM941 | 50 mg/kg p.o. 5 days on/ 2 days off | 0.23 | <0.001 |
| 011 | LIM1074 | 50 mg/kg p.o. qd × 13 | 0.35 | 0.032 |
| 012 | LIM801 | 50 mg/kg p.o. 5 days on/ 2 days off | 0.37 | 0.001 |
| 013 | LIM1054 | 50 mg/kg p.o. qd × 14 | 0.38 | 0.045 |
| 014 | LIM1097 | 50 mg/kg p.o. qd × 14 | 0.41 | 0.046 |
| 015 | LIM1057 | p.o. 50 mg/kg, qd × 14 | 0.43 | 0.003 |
| 016 | LIM1068 | 50 mg/kg p.o. qd × 13 | 0.47 | 0.024 |
| 017 | LIF1069 | 50 mg/kg p.o. qd × 14 | 0.47 | 0.024 |
| 018 | LIM1078 | 50 mg/kg p.o. qd × 13 | 0.48 | 0.055 |
| 019 | LIM1088 | 50 mg/kg p.o. qd × 13 | 0.54 | 0.182 |
| 020 | LIMsh050 | 50 mg/kg p.o. qd × 14 | 0.78 | 0.134 |
| 021 | LIM334 | 50 mg/kg p.o. 5 days on/ 2 days off | 1.13 | 0.659 |

Example 2. HCC-PDX can be Classified into Three Major Categories Per Global Gene Expression Profiling HCC is a disease of diverse types. Global gene expression profiling of patient tumor samples have revealed that HCC can be classified into three major subtypes. Recently, transcriptome analysis has classified HCC into three major categories with distinct clinical parameters as well as cellular differentiation[1]. They are S1 (stem-like group with activation of the WNT pathway and TGF-β), S2 (activation of MYC and AKT), and S3 (hepatocyte differentiation). HCC-PDXs) are believed to be predictive experimental models by maintaining the original patients' histopathological and genetic profiles[2,3]. This present study attempted to test this hypothesis by demonstrating whether HCC-avatar have similar genomic profiles as the patient tumors in classification and biological properties.

First, all described HCC-PDXs were used in avatar trial were profiled for global gene expression as previously described (9, 10). We assessed the resemblance of our "HCC-Avatars" to patient tumors using the same algorithm that was used to classify clinical patient samples[1]. Twenty-two HCC-PDX models can be classified into 3 groups, among which S1 and S2 are more closely related (see, Table 2). Using the 572 genes generated from the algorithm, the same classifications were obtained by hierarchical clustering and principal component analysis (PCA), except for two outliers. The results demonstrate that our cohort of HCC-PDXs can be divided into the same three subclasses as those from patient samples[1].

Using miRNA expression-criterion developed by Luk et al., our collection of HCC PDXs were classified into two classes, 14q32.2-hi and 14q32.2-lo. When compared to the S1, S2, S3 subclasses determined by mRNA profiling described above, S1 belongs to 14q32.2-lo, and S2/3 belong to 14q32.2-hi (except LI1025, LI1078) (see, Table 2).

TABLE 2

Classification of HCC HuPrime ® by mRNA and miRNA profiling

| PDX model | by mRNA | by 14q32.2 miRNA cluster |
|---|---|---|
| LI0612 | class 1 | low expression |
| LI0941 | class 1 | low expression |
| LI0348 | class 1 | NA |
| LI1646 | class 1 | low expression |
| LI1074 | class 1 | Low expression |
| LI1639 | class 1 | low expression |
| LI0801 | class 1 | low expression |
| LI1055 | class 1 | Low expression |
| LI1098 | class 1 | low expression |
| LI1057 | class 1 | low expression |
| LI1058 | class 1 | low expression |
| LI1054 | class 1 | low expression |
| LI0050 | class 2 | high expression |
| LI0752 | class 2 | high expression |
| LI1025 | class 2 | |
| LI0574 | class 2 | |
| LI1035 | low expression | high expression |
| LI1068 | NA | high expression |
| LI1069 | class 3 | high expression |
| LI1078 | class 3 | low expression |
| LI1081 | class 3 | NA |
| LI1088 | class 3 | high expression |

Serum AFP and tumor AFP-mRNA levels were found to be strongly and positively correlated, and also associated with S2/3[1] and 14q32.2-hi[4], consistent with previous reports[1]. Six stem-like markers were found not to be associated with S1[1], nor with 14q32.2-hi[4], thus different from the report by Luk et al[4]. Activation of c-MET, as defined by response to c-MET inhibitor, seems only observed in S1, consistent with one of previous observations[5], but not the other[4]. When all these models were treated with Sorafenib, a multi-kinase inhibitor, there seemed to be no correlation in the tumor responses between the subclasses (data not shown). We are currently investigating the relevant drug response to the classification in order to investigate the utility of this classification. Nevertheless, our data suggested that HCC-HuPrime® are good representative of patient tumors, and thus are thus likely predictive experimental models.

Example 3. Identification of HCC Gene Expression Signature Predictive of Response to Sorafenib A statistical method based on linear regression was used to identify predictive biomarker (i.e., gene signature) using global gene expression levels and the measured Sorafenib treatment effect on HCC-PDX as by % $\Delta T/\Delta C$ as described above. By pre-set statistic criteria including p-value<0.0001, range of gene expression across tested HCC-PDX>4 folds, no outlier in the linear regression analysis, we can derive a signature consisting of 8 genes that demonstrated good predictivity (e.g., FIG. 1, and Table 3). It is worth noting that a signature with more genes will create better relevance and smaller p-value, while have less practical values in the clinical application. The stringency of the preset criteria will determine the number of signature genes.

Although these signature genes are identified purely by statistical analysis and no biological knowledge was used to do any filtration before and after the analysis, these signature genes may be used to predict a subject's response to a multi-kinase inhibitor. Several genes are related to glucose and fructose metabolism. Two genes are in the Interferon (IFN) mediated pathways (note: a Phase I clinical trial is ongoing for using Peginterferon Alfa-2b with Sorafenib in patients with unresectable or metastatic clear cell renal carcinoma, see ClinicalTrials.gov Identifier No.: NCT00589550, which is incorporated herein by reference in its entirety).

TABLE 3

Exemplary Signature genes

| Gene ID | Gene name | Gene annotation | Reference |
|---|---|---|---|
| SEC14L2 | SEC14-like 2 (*S. cerevisiae*), a.k.a., SEC14 (*S. Cerevisiae*)-Like, SEC14-Like Protein, C22orf6, Tocopherol-Associated Protein, TAP, TAP1, hTAP. Alpha-Tocopherol-Associated Protein, Squalene Transfer Protein, SPF, KIAA1186, or KIAA1658 | This gene encodes a cytosolic protein which belongs to a family of lipid-binding proteins including Sec14p, alpha-tocopherol transfer protein, and cellular retinol-binding protein. The encoded protein stimulates squalene monooxygenase which is a downstream enzyme in the cholesterol biosynthetic pathway. Alternatively spliced transcript variants encoding different isoforms have been identified for this gene. (provided by RefSeq) | genecards.org SEQ ID NO: 1 SEC14L2 transcript variant 1 SEQ ID NO: 2 SEC14L2 isoform 1 SEQ ID NO: 3 SEC14L2 transcript variant 2 SEQ ID NO: 4 SEC14L2 isoform 2 SEQ ID NO: 5 SEC14L2 transcript variant 3 SEQ ID NO: 6 SEC14L2 isoform 3 |
| H6PD | hexose-6-phosphate dehydrogenase (glucose 1-dehydrogenase), a.k.a., GDH, Glucose Dehyrogenase, CORTRD1, G6PDH, 6-phophogluconolactonase, G6PD, H form, GDH/6PGL Endoplasmic, Bifuntional Protein, Glucose-1-Dehydrogenase, Glocose Dehyrogenase, Glucose-6-Phosphate, Dehydrogenase, Salivary, EC 1.1.1.49, EC 2.7.4.3, or EC 3.1.1.31 | Oxidizes glucose-6-phosphate and glucose, as well as other hexose-6-phosphates | genecards.org SEQ ID NO: 7 H6PD transcript variant 1 SEQ ID NO: 8 H6PD isoform 1 SEQ ID NO: 9 H6PD transcript variant 2 SEQ ID NO: 10 H6PD isoform 2 |

TABLE 3-continued

Exemplary Signature genes

| Gene ID | Gene name | Gene annotation | Reference |
|---|---|---|---|
| TMEM140 | transmembrane protein 140 | NA | genecards.org<br>SEQ ID NO: 11<br>TMEM140 transcript<br>SEQ ID NO: 12<br>TMEM140 protein |
| SLC2A5 | solute carrier family 2 (facilitated glucose/fructose transporter), member 5, a.k.a., GLUT5, Glucose Transporter Type 5, Small intestine, GLUT-5, Glucose Transporter-Like Protein 5, or Fructose Transporter | Cytochalasin B-sensitive carrier. Seems to function primarily as a fructose transporter | genecards.org<br>SEQ ID NO: 13<br>SLC2A5 transcript variant 1<br>SEQ ID NO: 14<br>SLC2A5 isoform 1<br>SEQ ID NO: 15<br>SLC2A5 transcript variant 2<br>SEQ ID NO: 16<br>SLC2A5 isoform 2 |
| ACTA1 | actin, alpha 1, skeletal muscle, a.k.a., ACTA, Nemaline Myopathy Type 3, ASMA, CFTD1, NEM3, CFTD, CFTDM, MPFD, NEM1, NEM2, Actin, Alpha Skeletal Muscle, or Alpha-actin-1 | Actins are highly conserved proteins that are involved in various types of cell motility and are ubiquitously expressed in all eukaryotic cells | genecards.org<br>SEQ ID NO: 17<br>ACTA1 transcript<br>SEQ ID NO: 18<br>ACTA1 protein |
| IRF8 | interferon regulatory factor 8, a.k.a., ICSBP1, Interferon Consensus Sequence Binding Protein 1, Interferon Consensus Binding Protein, H-ICSBP, UCSBP, or IRF-8, | Specifically binds to the upstream regulatory region of type I IFN and IFN-inducible MHC class I genes (the interferon consensus sequence (ICS)). Plays a negative regulatory role in cells of the immune system | genecards.org<br>SEQ ID NO: 19<br>IRF8 transcript<br>SEQ ID NO: 20<br>IRF8 protein |
| STAT2 | signal transducer and activator of transcription 2, 113 kDa, a.k.a., ISGF-3, P113, STAT113, Interferon alpha Induced, Transcriptional Activator, Signal Transducer And Activator of Transcription 2, p113 | Signal transducer and activator of transcription that mediates signaling by type I IFNs (IFN-alpha and IFN-beta). Following type I IFN binding to cell surface receptors, Jak kinases (TYK2 and JAK1) are activated, leading to tyrosine phosphorylation of STAT1 and STAT2. The phosphorylated STATs dimerize, associate with ISGF3G/IRF-9 to form a complex termed ISGF3 transcription factor, that enters the nucleus. ISGF3 binds to the IFN stimulated response element (ISRE) to activate the transcription of interferon stimulated genes, which drive the cell in an antiviral state | genecards.org<br>SEQ ID NO: 21<br>STAT2 transcript variant 1<br>SEQ ID NO: 22<br>STAT2 isoform 1<br>SEQ ID NO: 23<br>STAT2 transcript variant 2<br>SEQ ID NO: 24<br>STAT2 isoform 2 |
| UGT2A1/<br>UGT2A2 | UDP glucuronosyltransferase 2 family, polypeptide A1, complex locus, a.k.a., UDP-Glucuronosyltransferase 2A1, UDPGT 2A, UDP Glycosyltransferase 2 Family, Polypeptide A1, UGT2A2, or EC 2.4.1.17 | UDP-glucuronosyltransferases catalyze phase II biotransformation reactions in which lipophilic substrates are conjugated with glucuronic acid to increase water solubility and enhance excretion. They are of major importance in the conjugation and subsequent elimination of potentially toxic xenobiotics and endogenous compounds. Active on odorants and seems to be involved in olfaction; it could help clear lipophilic odorant molecules from the sensory epithelium | genecards.org<br>SEQ ID NO: 25<br>UGT2A1 transcript variant 1<br>SEQ ID NO: 26<br>UGT2A1 isoform 1<br>SEQ ID NO: 27<br>UGT2A1 transcript variant 2<br>SEQ ID NO: 28<br>UGT2A1 isoform 2<br>SEQ ID NO: 29<br>UGT2A1 transcript variant 3<br>SEQ ID NO: 30<br>UGT2A1 isoform 3 |

Materials and Methods

Patient tumor samples and engraftment in immunocompromised mice. Freshly and surgically removed tumor tissues were obtained from the patients diagnosed as HCC through collaboration with the Beijing Keluoen Translational Medicine Institute and Hebei Medical University Fourth Hospital with approval by the Institutional Review Boards of Hebei Medical University Fourth Hospital and the informed consents from patients. The engraftments of patient tumor fragments into immunocompromised mice subcutaneously have been broadly described by others. Briefly, the tumors were sliced into 3×3×3 mm3 fragments and inoculated subcutaneously on the flank of mice (Balb/c nude, 6-8 wks old, female, Beijing HFK Bioscience Co. Ltd., Beijing, China). The tumor growth was monitored twice weekly by using a caliper. The established tumor models from these patient samples, called passage 0 or P0, were serially re-engrafted to maintain tumors, these subsequent passages were called P1, 2, 3 . . . (<10). When tumors sizes reach 500-700 mm3 (1/2 length×width$^2$), they were harvested for the next round of engraftment to passage the tumors and to conduct studies of pharmacology, histopathology, immunohistology, cellular and molecular analysis. All procedures were performed under sterile conditions at Crown Bioscience SPF facility. All studies involving experimental animals were carried out in strict accordance with the recommendations of the Guide for the Care and Use of Laboratory Animals of the National Institutes of Health. The protocol was approved by the Committee on the Ethics of Animal Experiments of Crown Bioscience, Inc. (Crown Bioscience IACUC Committee).

Evaluation of antitumor activity. When tumor volume reaches 100-150 mm3, the mice were randomly grouped into two groups of 5 mice with similar average tumor volume. The control group was treated immediately after grouping with vehicle control (PBS, weekly IP injection for two weeks); the treatment groups were treated with one of the followings: cetuximab (weekly IP injection for two weeks, 1 mg/mouse, Merck KGaA), erlotinib (daily oral, mg/kg, Nanjing Angel Pharmaceutical Co.), crizotinib (daily oral, 50 mg/kg, Selleckchem.com). The tumor growth was monitored twice weekly, and % ΔT/ΔC value were calculated for assessing tumor response to the treatment (ΔT=tumor volume change in the treatment group and ΔC=tumor volume change in control group).

IHC analysis of HuPrime® tumors. Standard immunohistochemistry was used to analyze tumor tissues from the HuPrime models. Briefly, the tissues were fixed in 10% neutral buffered formalin and embedded in paraffin per standard histological procedures. After deparaffinization and rehydratation, 3-μm thick tissue sections were pretreated at 95° C. in 0.01M sodium citrate, pH6.0 solution for 30 min, followed by staining with rabbit anti-human monoclonal pERK or pEGFR antibody (Cell Signaling, Boston, USA). Positive staining was detected using Ultra Vision LP large Volume Detection System HRP Polymer (Ready-To-Use) Kit (Lab Vision, Fremont, Calif.). DAB was used as the chromogenic substrate, and sections were counterstained with Gill's Hematoxylin (Fisher Scientific, Fair Lawn, USA). The test specimens were then scored independently by three investigators in a blinded fashion per following criteria: 0, no staining; 1+, minimal staining; 2+, moderate staining; 3+, strong staining. Areas of most intensity were identified by scanning tumor sections at low power (×100), and then images were photographed at high magnification (×400) using Olympus BX51 microscopy system with DP71 digital camera (Olympus, Melville, N.Y.).

Expression profiling of HCC-PDX and gene copy number analysis. Fresh HCC HuPrime™ tumor tissues were collected from the tumor-bearing mice, snap-frozen, and stored at −80° C. before being used for genetic and genomic analysis. For gene profiling analysis, the total RNA was isolated from the frozen tissues using Trizol (Invitrogen, Carlsbad, Calif.) per the manufacturer's instructions, and purified using RNeasy mini columns (Qiagen). RNA quality was assessed on a Bioanalyzer (Agilent). Only RNA samples with high quality (RIN>8) were used for expression profiling assays on Affymetrix HG-U219 array plates following standard protocol (GeneChip® 3'IVT Expression Kit, User Manual, Affymetrix, P/N 702646 Rev. 8). Raw CEL data sets of all samples were normalized by RMA algorithm. Probe set intensity was expressed as Log (2) transformed values. For SNP/CNV assay using Affymetrix® SNP6.0 chips, genomic DNA was isolated and purified using Genomic DNA Tissue and Blood Isolation Kit (Qiagen) following manufacturer's instruction. DNA processing and chip hybridization were performed following standard Affymetrix protocol (Affymetrix® Genome-Wde Human SNP Nsp/Sty 6.0 User Guide, P/N 702504, Rev. 4). Raw CEL data was QC-ed and filtered to remove low call-rate samples, and gene copy number analysis were performed by PICNIC and/or PennCNV methods. For some of the samples, the relative gene copy numbers were determined by qPCR. Briefly, the same genomic DNAs were subjected to amplification using MET specific primers (SEQ ID NO: 31, MET-F: GCTGGTGGTCCTACCATACATG; SEQ ID NO: 32, MET-R: CTGGCTTACAGCTAGTTTGCCA) by SYBR Green based quantitative PCR. The mammalian LINE-1 retrotransposon gene was used as a reference. The q-PCR data was analyzed on the chromo4 system using Opticon Monitor 3 software to generate the raw data. The raw data was then processed using the delta CT relative quantification method. ΔCT=(CT value of target gene)−(CT value of reference gene). Delta CT values were then converted into intensity value (POWER(ΔCT,-2)). All data was normalized to that of a sample with known MET copy number to obtain relative MET copy number.

Discussion

Hepatocellular carcinoma (HCC) is a heterogeneous. The only approved target therapy is Sorafenib, either as monotherapy or in combination with chemotherapy. However, the treatment so far has shown limited overall benefit. However, as a multi-kinase inhibitor, this is largely due to high toxicity and also low overall efficacy, since there is lack of patient stratification that can identify the likely responders who can actually benefit from the treatment and the likely non-responders who can avoid the unnecessary toxicity. Therefore, developing such an individualized treatment plan would improve the overall treatment benefits. Unfortunately, so far clinical practice of Sorafenib has yet to reveal effective biomarkers to support such individualized treatments.

HCC-PDXs capture the original patient disease physiology as well as the underlying genetic diversity for each patient (2). These experimental models can be used as "patient surrogates or xenopatients (12)" to test drug candidates prior to the inception of clinical development. A large collection of established HCC-PDXs, or a library of HCC-PDX, can represent heterogeneity and diversity of the diseases. With their availability, they can be used to run a randomized phase II clinical trial-like study on any given drug. Such trials not only reveal the overall benefit of treatment by demonstrating % of responders, but also to potentially reveal valuable biomarkers (or molecular signatures) to be associated with these responders, if the models have been comprehensively profiled, as the ones described in this report. These biomarkers, once validated in the clinic, can potentially be used for patient stratification.

This report described a clinical trial-like study under well controlled experimental parameters and using a panel of randomized HuPrime® HCC models of full genetic annotations. The statistic analysis of our trial data indeed revealed a specific gene expression signature, HCC-Sorafenib-HuSignature™). This signature can be used to identify patients with higher probability to respond, or not respond to, Sorafenib, in a prospective clinical trial and also in clinical treatment practice.

In general, our HuTrial/HuSignature™ platform exemplified in this report is designed to discover predictive signatures by conducting a "phase II clinical trial-like" study by employing large collection of genome-defined HuPrime® PDX models and by using bioinformatic and statistic analysis. The basis of process is that the outcome can enable bioinformatician and biostatistician to identify specific genetic signature which has a high correlation with drug response or drug resistance. The resulting signature ("training set") can be further confirmed by either running more studies with additional HuPrime® models, or in a prospective clinical trial study ("test set"). The potential applications of this platform include: a) discovery of biomarkers for early stage clinical drug candidate; b) indication selection and expansion; c) life cycle management for marketed drugs; d) novel indication discovery for "me-too" drugs The most important cost driver for drug development is the high failure rate in late stage clinical development (13). The need to reduce drug attrition is especially acute in the field of oncology, where drugs often fail not because of toxicity but rather lack of efficacy. The successful development of drugs like trastuzumab, imatinib, and gefitinib has demonstrated the critical need to identify biomarkers in order to select patients which are most likely to benefit from the drug treatment. Our HuTrial/HuSignature™ platform could be a very powerful tool to be used to minimize the attrition during drug clinical development.

Patient derived xenografts (PDXs) are considered experimental models mimicking patient tumors, or "patient avatars". We performed a clinical-like trial (phase II-like) using a cohort of 21 hepatocellular carcinoma (HCC) patient derived xenografts (PDXs), also called patient avatar trial, for testing their response to multi-kinase inhibitor Sorafenib. 13 out of 21 PDXs (62%) achieved effective tumor growth inhibition with $\Delta T/\Delta C<40\%$ ($p<0.05$) by the treatment of Sorafenib at the doses of 50 mg/kg. Gene expression profiles of these PDXs were analyzed to reveal the mRNA expression signatures that may be predictive of the response to Sorafenib. This signature can be potentially used to develop companion diagnostics to stratify patent treatment, or individualized treatment.

Example 4. Identifying and Using Gene Markers

The efficacy of Sorafenib, Sunitinib, Axitinib, Vandetanib, Pazopanib, and Cabozantinib is measured on a panel of HCC PDXs each of which has multiple mice, at least 3, in both the control group that receives vehicle. The treatment group receives Sorafenib, Sunitinib, Axitinib, Vandetanib, Pazopanib, or Cabozantinib.

For each PDX, drug efficacy is quantified by % $\Delta T/\Delta C$ wherein $\Delta T$ is the tumor volume change in the treatment group and $\Delta C$ is the tumor volume change in control group. The mRNA expression levels or the protein levels of 2, 3, 4, 5, 6, 7, 8 or more marker genes are profiled by microarray, RNAseq, and/or RT-PCR. In some embodiments, the markers include SEC14L2, H6PD, TMEM140, SLC2A5, ACTA1, IRF8, STAT2, and/or UGT2A1. In some embodiments, other markers can be included.

A signature score is calculated based on the expressions or the protein levels of the marker genes, and its predictive power is quantified by the coefficient of determination (r2) and the associated p-value. Higher values of r2 and/or lower values of p-value indicate better predictive power. A p-value at least smaller than 0.05 is needed for considering the signature have any predictive power. In some embodiments, one or more particular marker is especially useful for predicting the responsiveness of a subject to a particular multi-kinase inhibitor.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions.

Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

REFERENCES

1. Llovet J M, Ricci S, Mazzaferro V, Hilgard P, Gane E, Blanc J F, et al. Sorafenib in advanced hepatocellular carcinoma. N Engl J Med. 2008; 359:378-90.
2. Ding L, Ellis M J, Li S, Larson D E, Chen K, Wallis J W, et al. Genome remodelling in a basal-like breast cancer metastasis and xenograft. Nature. 2010; 464:999-1005.
3. Marangoni E, Vincent-Salomon A, Auger N, Degeorges A, Assayag F, de Cremoux P, et al. A new model of patient tumor-derived breast cancer xenografts for preclinical assays. Clin Cancer Res. 2007; 13:3989-98.
4. Nemati F, Sastre-Garau X, Laurent C, Couturier J, Mariani P, Desjardins L, et al. Establishment and characterization of a panel of human uveal melanoma xenografts derived from primary and/or metastatic tumors. Clin Cancer Res. 2010; 16:2352-62.
5. Nemati F, Daniel C, Arvelo F, Legrier M E, Froget B, Livartowski A, et al. Clinical relevance of human cancer xenografts as a tool for preclinical assessment: example of in-vivo evaluation of topotecan-based chemotherapy in a panel of human small-cell lung cancer xenografts. Anticancer Drugs. 2010; 21:25-32.
6. Fichtner I, Rolff J, Soong R, Hoffmann J, Hammer S, Sommer A, et al. Establishment of patient-derived non-small cell lung cancer xenografts as models for the identification of predictive biomarkers. Clin Cancer Res. 2008; 14:6456-68.
7. Hennessey P T, Ochs M F, Mydlarz W W, Hsueh W, Cope L, Yu W, et al. Promoter methylation in head and neck squamous cell carcinoma cell lines is significantly different than methylation in primary tumors and xenografts. PLoS One. 2011; 6:e20584.
8. Chen D, Sheng Guo, Jie Cai, Xiaoming Song, Mengmeng Yang, Jianyun Deng, Taiping Chen1, Jean-Pierre Weryl, Yiyou Chen1 and Qixiang Li. Cetuximab response in CRC patient-derived xenografts is predicted by RAS pathway activation rather than KRAS mutation status. in preparation; in submission.
9. Yang M, Baoen Shan, Qiaoxia Li, Xiaoming Song, Jianyun Deng, Jie Cai, Likun Zhang1, Junjie Lu, Zhenjian Du, Taiping Chen, Jean-Pierre Wery, Yiyou Chen and Qixiang Li. Overcoming erlotinib resistance with tailored treatment regimen in patient derived xenografts from naïve Asian NSCLC patients. Int J Cancer. 2012; September 5. doi: 10.1002/ijc.27813. [Epub ahead of print].
10. Yang M, Jie Cai, Sheng Guo, Xuesong Huang, Jie Yang, Dawei Chen, Jiahua Jiang, Likun Zhang, Xiaoming Song, Taiping Chen, Jean Pierre Wery, Yiyou Chen and Qixiang Li. Squamous non-small cell lung cancer (NSCLC-SCC) patient-derived xenografts (PDX) from Asian patients have high response rate (RR) to cetuximab than those from non-SCC patients. submitted.
11. Loboda A, Nebozhyn M, Klinghoffer R, Frazier J, Chastain M, Arthur W, et al. A gene expression signature of RAS pathway dependence predicts response to PI3K and RAS pathway inhibitors and expands the population of RAS pathway activated tumors. BMC Med Genomics. 2010; 3:26.
12. Andrea Bertotti G M, Francesco Galimi, et al. A Molecularly Annotated Platform of Patient-Derived Xenografts ("Xenopatients") Identifies HER2 as an Effective Therapeutic Target in Cetuximab-Resistant Colorectal Cancer. Cancer Discovery. 2011; 1:508-23.
13. Paul. How to improve R&D Productivity: The Pharmaceutical Industry Grand Challenge. Nature Reviews Drug Discovery 2010; 9:203-14.

Each of references mentioned above is herein incorporated by reference in its entirety for all purposes.

The invention claimed is:

1. A method for treating cancer in a human patient, comprising administering a multi-kinase inhibitor to the human patient,
   wherein before being treated, the activity level of a gene marker in tumor tissue obtained from the human patient is determined, and wherein the marker is solute carrier family 2, member 5 (SLC2A5),
   wherein the administration of the multi-kinase inhibitor to the human patient is based on the activity level of SLC2A5 such that the multi-kinase inhibitor is administered to the human patient if the gene marker in the human patient has an activity lower than that in a randomly selected human patient population having the cancer or in a human patient population having the cancer and not responsive to the treatment, wherein the activity is gene expression, gene amplification, and/or protein level, and
   wherein the multi-kinase inhibitor targets to vascular endothelial growth factor (VEGF)-mediated angiogenesis and blocks the RAF/extracellular signal regulated kinase (ERK) kinase (MEK)/ERK cascade.

2. The method of claim 1, wherein the activity of the gene marker is protein level.

3. The method of claim 1, wherein the activity of the gene marker is gene expression level.

4. The method of claim 1, wherein the multi-kinase inhibitor is Sorafenib, Sunitinib, Axitinib, Vandetanib, Pazopanib, Cabozantinib, or mixture thereof.

5. The method of claim 1, wherein the human patient is a human with hepatocellular carcinoma.

6. The method of claim 1, wherein the method further comprises determining the activity level of one or more additional gene makers selected from the group consisting of hexose-6-phosphate dehydrogenase (H6PD), transmembrane protein 140 (TMEM140), actin alpha 1 (ACTA1), interferon regulatory factor 8 (IRF8), signal transducer and activator of transcription 2 (STAT2), and UDP glucuronosyltransferase 2 family, polypeptide A1 (UGT2A1).

* * * * *